(12) United States Patent
Yousef et al.

(10) Patent No.: US 7,507,403 B2
(45) Date of Patent: Mar. 24, 2009

(54) KALLIKREIN GENE

(75) Inventors: George M. Yousef, Toronto (CA); Eleftherios P. Diamandis, Toronto (CA)

(73) Assignee: Mount Sinai Hospital, Toronto (CA)

( * ) Notice: Subject to any disclaimer, the term of this patent is extended or adjusted under 35 U.S.C. 154(b) by 0 days.

(21) Appl. No.: 11/729,560

(22) Filed: Mar. 29, 2007

(65) Prior Publication Data

US 2007/0178114 A1  Aug. 2, 2007

Related U.S. Application Data

(62) Division of application No. 10/344,394, filed as application No. PCT/CA01/01141 on Aug. 10, 2001, now Pat. No. 7,199,229.

(60) Provisional application No. 60/224,853, filed on Aug. 11, 2000.

(51) Int. Cl.
*C12N 9/64* (2006.01)
*C12N 15/75* (2006.01)
*C12N 15/74* (2006.01)
*C12N 15/79* (2006.01)
*A61K 39/00* (2006.01)

(52) U.S. Cl. ............... 424/94.64; 435/69.1; 435/252.3; 435/320.1; 435/226; 424/184.1

(58) Field of Classification Search .................. None
See application file for complete search history.

(56) References Cited

U.S. PATENT DOCUMENTS

| | | | |
|---|---|---|---|
| 6,962,793 B2 | 11/2005 | Diamandis | |
| 7,022,497 B1 | 4/2006 | Yousef et al. | |
| 7,199,229 B2 | 4/2007 | Diamandis et al. | |
| 2002/0064856 A1 | 5/2002 | Plowman et al. | |
| 2003/0232349 A1 | 12/2003 | Delegeane et al. | |
| 2004/0096915 A1 | 5/2004 | Diamandis et al. | |
| 2004/0115745 A1 | 6/2004 | Diamandis et al. | |
| 2004/0203012 A1 | 10/2004 | Diamandis et al. | |
| 2005/0106586 A1 | 5/2005 | Diamandis | |
| 2005/0176002 A1 | 8/2005 | Diamandis et al. | |
| 2005/0287528 A1 | 12/2005 | Diamandis et al. | |
| 2006/0073525 A1 | 4/2006 | Yousef et al. | |
| 2006/0134114 A1 | 6/2006 | Yousef et al. | |
| 2006/0134120 A1 | 6/2006 | Diamandis | |
| 2006/0141471 A1 | 6/2006 | Diamandis et al. | |
| 2006/0159616 A1 | 7/2006 | Yousef et al. | |
| 2006/0223059 A1 | 10/2006 | Yousef et al. | |

(Continued)

FOREIGN PATENT DOCUMENTS

WO    WI 02/08396 A2    1/2002

(Continued)

OTHER PUBLICATIONS

Altschul, "Gapped BLAST and PSI-BLAST: a new generation of protein database search programs", Nucleic Acids Research, 25(17):3389-3402 (Sep. 1, 1997).

(Continued)

*Primary Examiner*—Rebecca E Prouty
*Assistant Examiner*—William W Moore
(74) *Attorney, Agent, or Firm*—Howson & Howson LLP

(57) ABSTRACT

The invention relates to a kallikrein protein, compositions comprising the protein, and the use thereof.

4 Claims, 11 Drawing Sheets

U.S. PATENT DOCUMENTS

2006/0269971 A1  11/2006  Diamandis

FOREIGN PATENT DOCUMENTS

WO    WO 02/00860 A2    1/2002
WO    WO 02/14485 A3    2/2002

OTHER PUBLICATIONS

Anisowicz, "A Novel Protease Homolog Differentially Expressed in Breast and Ovarian Cancer", Molecular Biology, 2(5):624-636 (Sep. 1996).

Ashley, "Tissue-Specific Expression of Kallikrein-Related Genes in the Rat", Biochemistry, 24(17):4520-4527 (Aug. 13, 1985).

Bhoola, "Bioregulation of Kinins: Kallikreins, Kininogens, and Kininases", Pharmacological Reviews, 44(1):1-80 (Mar. 1992).

Black, "Development of an Ultrasensitive Immunoassay for Human Glandular Kallikrein with no cross-Reactivity from Prostate-specific Antigen", Clinical Chemistry, 45(6):790-799 (Jun. 1999).

Chen, "Molecular Cloning And Characterization Of A Novel Kallikrein Transcript In Colon And Its Distribution In Human Tissues", Brazilian Journal of Medical and Biological Research, 27(8):1829-1838 (Aug. 1994).

Clements, "The Molecular Biology of the Kallikreins and their Roles in Inflammation", The Kinin System (Farmer, S., ed.), Academic Press, 5:71-97 (1997).

Cumming, "Expression Of Tissue Kallikreins In Human Kidney", Clinical Science, 87(1):5-11 (Jul. 1994).

Dihanich, "A Novel Serine Proteinase-Like Sequence From Human Brain" Biochim Biophys Acta, 1218(2):225-228 (Jun. 21, 1994).

Diamandis, "Prostate-specific Antigen: Its Usefulness in Clinical Medicine", Trends in Endocrinology and Metabolism, 9(8):310-316 (Oct. 1, 1998).

Diamandis, "The New Human Kallikrein Gene Family: Implications in Carcinogenesis", Trends in Endocrinology and Metabolism, 11(2):54-60 (Mar. 2000).

Diamandis, "Detection of Prostate Specific Antigen Immunoreactivity in Breast Tumors", Breast Cancer Research and Treatment, 32(3):301-310 (1994).

Diamandis, "New Biological Functions Of Prostate-Specific Antigen?", Journal of Clinical Endocrinol Metabolism, 80(5):1515-1517 (May 1995).

Diamandis, "Prostate Cancer. Will we win the battle in the next century?", Clinical Laboratory News, Oct. 14-16, 1999.

Diamandis, "Human Tissue Kallikrein Gene Family: A Rich Source of Novel Disease Biomarkers", Expert Reviews Molecular Diagnosis., 1:182-190 (Jul. 2001).

Diamandis, "New Nomenclature For The Human Tissue Kallikrein Gene Family", Clinical Chemistry, 46:1855-1858 (Nov. 2000).

Diamandis, "Immunofluorometric Assay of Human Kallikrein 6 (Zyme/Protease M/Neurosin) and Preliminary Clinical Applicaitons", Clinical Biochemistry, 33(5):369-375 (Jul. 2000).

Diamandis, "Human Kallikrein 6 (Zyme/Protease M/Neurosin): A New Serum Biomarker of Ovarian Carcinoma", Clinical Biochemistry, 33(7):579-583 (Oct. 2000).

Diamandis, "Human Kallikrein 6 As A Biomarker Of Alzheimer's Disease", Clinical Biochemistry, 33(8):663-667 (Nov. 2000).

Diamandis, "Prostate-Specific Antigen: A Cancer Fighter And A Valuable Messenger?", Clinical Chemistry, 46(7):896-900 (Jul. 2000).

Ekholm, "Stratum Corneum Chymotryptic Enzyme In Psoriasis", Archives of Dermatological Research, 291(4):195-200 (Apr. 1999).

Evans, "Mouse Glandular Kallikrein Genes. Structure and Partial Sequence Analysis Of The Kallikrein Gene Locus", The Journal of Biological Chemistry, 262(17):8027-8034 (Jun. 15, 1987).

Gan, "Sequencing and Expression Analysis Of The Serine Protease Gene Cluster Located In Chromosome 19q13 region", Gene, 257(1):119-130 (Oct. 17, 2000).

Goyal, "The Role for NESI Serine Protease as a Novel Tumor Suppressor", Cancer Research, 58(21):4782-4786 (Nov. 1, 1998).

Hansson, "Cloning, Expression, and Characterization of Stratum Corneum Chymotryptic Enzyme. A Skin-Specific Human Serine Proteinase", The Journal of Biological Chemistry, 269(30):19420-19426 (Jul. 29, 1994).

Heuzé, "Molecular Cloning and Expression of an Alternative hKLK3 Transcript Coding for a Variant Protein of Prostate-specific Antigen", Cancer Research, 59(12):2820-2824 (Jun. 15, 1999).

Hillier, Accession No. W73168 (Oct. 16, 1998).

Hillier, Accession No. N80762 (Mar. 29,, 1996).

IIDA, "Quantification Analysis of 5'-Splice Signal Sequences in mRNA Presursors. Mutations in 5'-Splice Signal Sequence of Human β-Globin Gene and β-Thalassemia", Journal of Theoretical Biology, 145(4):523-533 (Aug. 23, 1990).

Jaffa, "Effects of Diabetes and Insulin On Expression Of Kallikrein And Renin Genes In The Kidney", Kidney International, 41(4):789-795 (Apr. 1992).

Kishi, "Crystal Structure of Neuropsin, a Hippocampal Protease Involved in Kindling Epileptogenesis", The Journal of Biological Chemistry, 274(7):4220-4224 (Feb. 12, 1999).

Kozak, "An Analysis Of 5'-Noncoding Sequences From 699 Vertebrate Messenger RNAs", Nucleic Acids Research, 15(20):8125-8148 (Oct. 26, 1987).

Kozak, "An Analysis of Vertebrate mRNA Sequences: Intimations of Translational Control", The Journal of Cell Biology, 115(4):887-903 (Nov. 1991).

Lennon, "The I.M.A.G.E. Consortium: An Integrated Molecular Analysis of Genomes and Their Expression", Genomics, 33(1):151-152 (Apr. 1, 1996).

Little, "Zyme, a Novel and Potentially Amyloidogenic Enzyme cDNA Isolated from Alzheimer's Disease Brain", The Journal of Biological Chemistry, 272(40):25135-25142 (Oct. 3, 1997).

Liu, "Identificaiton of a Novel Serine Protease-like Gene, the Expression of Which is Down-Regulated during Breast Cancer Progression", Cancer Research, 56(14):3371-3379 (Jul. 15, 1996).

Luo, "Structural Characterization and Mapping of the Normal Epithelial Cell-Specific 1 Gene", Biochemical and Biophysical Research Communications, 247(3):580-586 (Jun. 29, 1998).

Margolius, "Urinary Kallikrein Excretion in Hypersensitive Man. Relationships to Sodium Intake and Sodium-Retaining Steroids", Circulation Research, 35(6):820-825 (Dec. 1974).

Meyer, "Factors Influencing the Ratio of Free to Total Prostate-Specific Antigen in Serum", International Journal of Cancer, 74(6):630-636 (Dec. 19, 1997).

Mitsui, "A Novel Form Of Human Neuropsin, A Brain-Related Serine Protease, Is Generated By Alternative Splicing And Is Expressed Preferentially In Human Adult Brain", European Journal of Biochemistry, 260(3):627-634 (Mar. 1999).

Miyata, "Two Types of Amino Acid Substitutions in Protein Evolution", Journal of Molecular Evolution, 12(3):219-236 (Mar. 15, 1979).

Momota, "Blockade Of Neuropsin, A Serine Protease , Ameliorates Kindling Epilepsy", European Journal of Neuroscience, 10(2):760-764 (Feb. 1998).

Nelson, "Molecular Cloning And Characterization Of Protase, An Androgen-Regulated Serine Protease WIth Prostate-Restricted Expression", Proceedings of the National Academy of Sciences, 96(6):3114-3119 (Mar. 16, 1999).

Partin, "Use of Human Glandular Kallikrein 2 for the Detection of Prostate Cancer: Preliminary Analysis", Urology, 54(5):839-845 (Nov. 1999).

Proudfoot, "3' Non-Coding Region Sequences In Eukaryotic Messenger RNA", Nature, 263(5574):211-214 (Sep. 16, 1976).

Riegman, "Molecular Cloning and Characterization of Novel Prostate Antigen cDNA's", Biochemical and Biophysical Research Communications, 155(1):181-188 (Aug. 1, 1988).

Riegman, "Characterization of the Prostate-Specific Antigen Gene: A Novel Human Kallikrein-like Gene", Biochemical and Biophysical Research Communications, 159(1):95-102 (Feb. 28, 1989).

Riegman, "Identification And Androgen-Regulated Expression Of Two Major Human Glandular Kallikrein-1 (hGK-1) mRNA Species", Molecular and Cellular Endocrinology, 76(1-3):181-190 (Apr. 1991).

Riegman, "Characterization of the Human Kallikrein Locus", Genomics, 14(1):6-11 (Sep. 1992).

Sheets, "Point Mutations in AAUAAA And The Poly (A) Addition Site: Effects On The Accuracy And Efficiency Of Cleavage And Polyadenylation In Vivo", Nucleic Acids Research, 18(19):5799-5805 (Oct. 11, 1990).

Sondell, "Association Between Expression of Stratum Corneum Chymotryptic Enzyme and Pathological Keratinization in Human Oral Mucosa", Acta Dermato-Venerelologica, 76(3):177-181 (May 1996).

Stenman, "New Ultrasensitive Assays Facilitate Studies on the Role of Human Glandular Kallikrein (hK2) as a Marker for Prostatic Disease", Clinical Chemistry, 45(6):753-754 (Jun. 1999).

Stephenson, "Localization of a New Prostate-specific Antigen-related Serine Protease Gene, KLK4, Is Evidence for an Expanded Human Kallikrein Gene Family Cluster on Chromosome 19q13.3-13.4" The Journal of Biological Chemsitry, 274(33):23210-23214 (Aug. 13, 1999).

Takayama, "Activation of Prostate-Specific Antigen Precursor (pro-PSA) by Prostin, A Novel Human Prostatic Serine Protease Identified By Degenerate PCR" Biochemistry, 40(6)1679-1687 (Feb. 13, 2001).

Tanimoto, "The Stratum Corneum Chymotryptic Enzyme that Mediates Shedding and Desquamation of Skin Cells is Highly Overexpressed in Ovarian Tumor Cells", Cancer, 86(10):2074-2082 (Nov. 15, 1999).

Underwood, "Cloning of Tumor-associated Differentially Expressed Gene-14, a Novel Serine Protease Overexpressed by Ovarian Carcinoma", Cancer Research, 59(17):4435-4439 (Sep. 1, 1999).

Yoshida, "Sequence Analysis And Expression Of Human Neuropsin cDNA and Gene", Gene, 213(1-2):9-16 (Jun. 15, 1998).

Yousef, "The New Kallikrein-like Gene, KLK-L2. Molecular Characterization, Mapping, Tissue Expression, and Hormonal Regulation", The Journal of Biological Chemistry, 274(53):37511-37516 (Dec. 31, 1999).

Yousef, "Identification of Novel Human Kallikrein-Like Genes on Chromosomes 19q13.3-q13.4" Anticancer Research, 19(4B):2843-2852 (Jul.-Aug. 1999).

Yousef, "Protase/KLK-LI Is a New Member of the Human Kallikrein Gene Family, Is Expressed in Prostate and Breast Tissues, and Is Hormonally Regulated", Cancer Research, 59(17):4252-4256 (Sep. 1, 1999).

Yousef, "Identification and Characterization of KLK-L4, a New Kallikrein-like Gene That Appears to be Down-regulated in Breast Cancer Tissues", The Journal of Biological Chemistry, 275(16):11891-11898 (Apr. 21, 2000).

Yousef, "Quantitative Expression of the Human Kallikrein Gene 9 (KLK9) in Ovarian Cancer: A New Independent and Favorable Prognostic Marker", Cancer Research, 61:7811-7818 (Nov. 1, 2001).

Yousef, "The New Human Tissue Kallikrein Gene Family: Structure, Function, and Association to Disease", Endocrine Reviews, 22(2):184-204 (Apr. 2001).

Yousef, "Cloning of a New Member of the Human Kallikrein Gene Family, KLK14, Which is Down-Regulated in Different Malignancies", Cancer Res., 61:3425-3431 (Apr. 15, 2001).

Yousef, "Genomic Organization of the Human Kallikrein Gene Family on Chromosome 19q13.3-q13.4", Biochem Biophys. Res. Commun., 276(1):125-133 (Sep. 16, 2000).

Yousef, "Genomic organization, Mapping, Tissue Expression, And Hormonal Regulation Of Trypsin-Like Serine Protease (TLSP PRSS20), A New Member Of The Human Kallikrein Gene Family", Genomics 63: 88-96 (Jan. 1, 2000).

Yousef, "The Expanded Human Kallikrein Gene Family: Locus Characterization and Molecular Cloning of a New Member, KLK-L3 (KLK9)", Genomics, 65(2):184-194 (Apr. 15, 2000).

Yousef, "Molecular Cloning Of The Human Kallikrein 15 gene (KLK15). Up-regulation in prostate cancer." The Journal of Biological Chemistry, 276(1):53-61 (Jan. 5, 2001).

Yousef, "Molecular Characterization Of Zyme/Protease M/Neurosin (PRSS9), a Hormonally Regulated Kallikrein-Like Serine Protease", Genomics, 62(2):251-259 (Dec. 1, 1999).

Yousef, "KLK12 is a Novel Serine Protease And A New Member Of The Human Kallikrein Gene Family-Differential Expression In Breast Cancer", Genomics, 69(3):331-341 (Nov. 1, 2000).

Yousef, "The KLK7 (PRSS6) Gene, Encoding For The Stratum Corneum Chymotryptic Enzyme Is A New Member Of The Human Kallikrein Gene Family—Genomic Characterization, Mapping, Tissue Expression And Hormonal Regulation", Gene, 254(1-2):119-128 (Aug. 22, 2000).

NCI-CGAP, Genbank Accession No. AW274270 (Jan. 6, 2000).

Birren, Genbank Accession No. AC027602 (Apr. 3, 2000).

Figure 1

```
TGGATTCTCTCACTCCCTCCCCAGACTGCAGCCGAACCCTGGTCCCTCCTCCACA
(ATG) TGG CTT CTC CTC ACT CTC TCC TTC CTG CTG GCA TCC ACA
  M   W   L   L   L   T   L   S   F   L   L   A   S   T
G gtgaggtggccccaggaggggggccaggtctgtgggagcaggtg...........
...Intron1..........................gcatcctctaccccttctcttag CA GCC CAG
                                                             A   A   Q
GAT GGT GAC AAG TTG CTG GAA GGT GAC GAG TGT GCA CCC CAC
 D   G   D   K   L   L   E   G   D   E   C   A   P   H
TCC CAG CCA TGG CAA GTG GCT CTC TAC GAG CGT GGA CGC TTT
 S   Q   P   W   Q   V   A   L   Y   E   R   G   R   F
AAC TGT GGC GCT TCC CTC ATC TCC CCA CAC TGG GTG CTG TCT
 N   C   G   A   S   L   I   S   P   H   W   V   L   S
GCG GCC CAC TGC CAA AGC CG gtatgaaggcaggggctcagggtcctga
 A   A  [H]  C   Q   S   R
ggga...........Intron 2................cgcactccactggcgggaaa
accactcgcccgcacag C TTC ATG AGA GTG CGC CTG GGA GAG CAC
                    F   M   R   V   R   L   G   E   H
AAC CTG CGC AAG CGC GAT GGC CCA GAG CAA CTA CGG ACC ACG
 N   L   R   K   R   D   G   P   E   Q   L   R   T   T
TCT CGG GTC ATT CCA CAC CCG CGC TAC GAA GCG CGC AGC CAC
 S   R   V   I   P   H   P   R   Y   E   A   R   S   H
CGC AAC GAC ATC ATG TTG CTG CGC CTA GTC CAG CCC GCA CGC
 R   N  [D]  I   M   L   L   R   L   V   Q   P   A   R
CTG AAC CCC CAG GTG CGC CCC GCG GTG CTA CCC ACG CGT TGC
 L   N   P   Q   V   R   P   A   V   L   P   T   R   C
CCC CAC CCG GGG GAG GCC TGT GTG GTG TCT GGC TGG GGC CTG
 P   H   P   G   E   A   C   V   V   S   G   W   G   L
GTG TCC CAC AAC GAG CCT GGG ACC GCT GGG AGC CCC CGG TCA
 V   S   H   N   E   P   G   T   A   G   S   P   R   S
CAA G gtgcgtgaaaggatggagctggat.............Intron 3............
 Q
ctccaagtccactgtcttccccag TG AGT CTC CCA GAT ACG TTG CAT
                            V   S   L   P   D   T   L   H
TGT GCC AAC ATC AGC ATT ATC TCG GAC ACA TCT TGT GAC AAG
 C   A   N   I   S   I   I   S   D   T   S   C   D   K
AGC TAC CCA GGG CGC CTG ACA AAC ACC ATG GTG TGT GCA GGC
 S   Y   P   G   R   L   T   N   T   M   V   C   A   G
GCG GAG GGC AGA GGC GCA GAA TCC TGT GAG gtcagagcctagagg
 A   E   G   R   G   A   E   S   C   E
ggccatcaggcggaagaagaggg........................Intron 4............cct
gagaccccctcttttccccacag GGT GAC TCT GGG GGA CCC CTG GTC
                         G   D  [S]  G   G   P   L   V
TGT GGG GGC ATC CTG CAG GGC ATT GTG TCC TGG GGT GAC GTC
 C   G   G   I   L   Q   G   I   V   S   W   G   D   V
CCT TGT GAC AAC ACC ACC AAG CCT GGT GTC TAT ACC AAA GTC
 P   C   D   N   T   T   K   P   G   V   Y   T   K   V
TGC CAC TAC TTG GAG TGG ATC AGG GAA ACC ATG AAG AGG AAC
 C   H   Y   L   E   W   I   R   E   T   M   K   R   N
(TGA)CTATTCTAGCCTATCTCCTGTGCCCCTGACTGAGCAGAAGCCCCCACAGCTGGCCAGCAGCCC
```

Figure 1 Cont'd

```
CGCCTGACATGGAACAGAACGGAGCCATCCCCCAAGACCCTGTCCAAGGCCCAGATGTTAGCCAAGG
ACTTGTCCCACCTGAGGACAAAGCTGGCGCTCAAGGTCACCTGTTTAATGCCAAGATAACAAAGCGC
TGATCCAAGTTGCTCTGTAGGAATTTCTGTGACTTTTTTCTGGGGTCAAAGAGAAACCCCGAGACAC
TGTACACTGTTCCTTTTCACCCACCACCCCGATCCCTAGGTGAGGAGAAGCGGCTTGAAGCAGGGCT
CCATTCATTCAACACACATGACCACCCGTGTGATCTTGAACAAGAGGCCCAATCTCACTTCGCCTTG
GTTTCCTTATCTGTAAAATGAGACCATCTTATTGCTGACTTCAAAGGGCTGTTGTGAGGATTAAATG
AGATGATTCGTCTGAACTGATTAAAATCGTGTCTGGCACTGA
```

```
zyme      187 KYGKDSCQGDSGGPLVCGDHLRGLVSWG-NIPCGSKEKPGVYTNVCRYTNWIQKTIQAK------------
KLK-L4    208 EGGKDSCEGDSGGPLVCNRTLYGIVSWG-DFPCGQEDRPGVYTRVSRYVLWIRETIRKYETQQQKWLKGPQ
KLK-L6    194 QGGKDSCQGDSGGPLVCRGQLQGLVSWG-MERCALEGYPGVYTNLCKYRSWIEEIMRDK------------
TLSP      225 EGGKDSCQGDSGGPLVCNQSLQGIISWG-QDPCAITRKPGVYTKVCKYVDWIQEIMKNN-----------
KLK-L3    194 EGGRGSCQGDSGGPLVCNGTLAGVVSCG-AEPCSRERRPAVYTSVCHYLDWIQEIMEN------------
KLK15     199 GRCAESCEGDSGGPLVCGGILQGIVSWG-DVPCDNTTKPGVYTKVCHYLEWIREIMKRN-----------
NES1      219 DRGQDPCQSDSGGPLVCDETLQGILSWG-VYPCGSAQHPAVYTQICKYMSWINKVERSN-----------
KLK-L5    190 VPGQDACQGDSGGPLVCGGVLQGLVSWGSVGPCGQDGIPGVYTYICKYVDWIRMIMRNN-----------
neuropsin 202 SKGADTCQGDSGGPLVCDCALQGITSWG-SDPCGRSDKPGVYTNICRYLDWIKKIEGSKG----------
PSA       203 TGGKSTCSGDSGGPLVCNGVLQGITSWG-SEPCALPERPSLYTKVVHYRKWIKDTIVANP----------
hK2       203 TGGKDTCGGDSGGPLVCNGVLQGVTSWG-PEPCALBEKPAVYTKVVHYRKWIKDTIAARP----------
hK1       204 EGGKDTCVGDSGGPLMCDGVLQGVTSWG-YVPCGTENKPSVAVRVLSYVKWIEDTIAENS----------
KLK-L2    235 KAGRDSCQGDSGGPMVCNGSLQGLVSWG-DYPCARENRPGVYTNLCKFTKWIQETIQANS----------
prostase  197 HDQKDSCNGDSGGPLICNGYLQGLVSFG-KAPCGQVGVPGVYTNLCKFTEWIEKTVQAS-----------
HSCCE     195 DSKNNACNGDSGGPLVCRGTLQGLVSWG-TFPCGQPNDPGVYTQVCKFTKWINDIMKKHR----------
                *  ......         .  .           .
```

Molecular weight marker
Salivary gland
Fetal brain
Stomach
Uterus
Lung
Heart
Thymus
Prostate
Fetal liver
Brain
Mammary gland
Adrenal gland
Colon
Thyroid
Spleen
Placenta
Skeletal muscle
Trachea
Cerebellum
Testis
Liver
Prancreas
Small intestine
Spinal cord
Kidney
Bone marrow
Negative control

KALLIKREIN GENE

CROSS-REFERENCE TO RELATED APPLICATIONS

This application is a divisional of U.S. patent application Ser. No. 10/344,394, filed Aug. 1, 2003, which issued as U.S. Pat. No. 7,199,229 on Apr. 3, 2007, which is a national stage of International Patent Application No. PCT/CA01/01141, filed Aug. 10, 2001, which claims the benefit of the priority of U.S. Provisional Patent Application No. 60/224,853, filed Aug. 11, 2000, now abandoned.

BACKGROUND OF THE INVENTION

The invention relates to nucleic acid molecules, proteins encoded by such nucleic acid molecules; and use of the proteins and nucleic acid molecules.

Kallikreins are a group of serine proteases that are found in diverse tissues and biological fluids. The term "kallikrein" was first introduced by Werle and colleagues who found high levels of their original isolates in the pancreas (in Greek, the "kallikreas") (1,2). Kallikreins are divided into two main groups; the plasma kallikrein, which is a single gene (3), and the tissue kallikreins, which are encoded by a large multigene family in rodents (4,5). Until recently, the human kallikrein gene family was thought to consist of only three members (6). However, 11 new members of the kallikrein gene family have been identified (7-18). The progress in this area of investigation has recently been reviewed (7).

Prostate specific antigen (PSA), currently the most useful tumor marker for prostate cancer diagnosis and monitoring, is a member of the human kallikrein gene family of serine proteases (19,20). In addition to PSA, human glandular kallikrein 2 (hK2, encoded by the KLK2 gene) has been proposed as an adjuvant diagnostic marker for prostate cancer (21,22). Moreover, accumulating evidence indicates that other members of the expanded kallikrein gene family may be associated with malignancy (7). The normal epithelial cell-specific 1 gene (NES1) (KLK10, according to the approved human tissue kallikrein gene nomenclature) was found to be a novel tumor suppressor, which is down-regulated during breast cancer progression (23). Other gene family members, including zyme (KLK6), neuropsin (KLK8), and human stratum corneum chymotyrptic enzyme (HSCCE; KLK7) were also found to be differentially expressed in certain types of malignancies (24-26).

SUMMARY OF THE INVENTION

The present inventors identified a nucleic acid molecule encoding a novel kallikrein. The nucleic acid molecule maps to chromosome 19q13.3-q13.4 and is located between the klk1 and klk3 genes. The novel nucleic acid molecule designated "klk15" has three alternatively spliced forms and is primarily expressed in the thyroid gland, and to a lower extent in the prostate, salivary and adrenal glands, colon, testis, and kidney. The expression of the nucleic acid is up-regulated in prostate cancer and it is under steroid hormone regulation in the LNCaP prostate cancer cell line. Higher expression of klk15 is associated with more aggressive (higher stage and higher grade) prostate tumors.

The novel kallikrein protein described herein is referred to as "Kallikrein 15", "KLK15", or "KLK15 Protein". The gene encoding the protein is referred to as "klk15".

Broadly stated the present invention relates to an isolated nucleic acid molecule of at least 30 nucleotides which hybridizes to one or more of SEQ. ID. NO. 1 through 5, or 10 through 24, or the complement of one or more of SEQ ID NO. 1 through 5, or 10 through 24 under stringent hybridization conditions.

The invention also contemplates a nucleic acid molecule comprising a sequence encoding a truncation of a KLK15 Protein, an analog, or a homolog of a KLK15 Protein or a truncation thereof. (KLK15 Protein and truncations, analogs and homologs of KLK15 Protein are also collectively referred to herein as "KLK15 Related Proteins").

The nucleic acid molecules of the invention may be inserted into an appropriate expression vector, i.e. a vector that contains the necessary elements for the transcription and translation of the inserted coding sequence. Accordingly, recombinant expression vectors adapted for transformation of a host cell may be constructed which comprise a nucleic acid molecule of the invention and one or more transcription and translation elements linked to the nucleic acid molecule.

The recombinant expression vector can be used to prepare transformed host cells expressing KLK15 Related Proteins. Therefore, the invention further provides host cells containing a recombinant molecule of the invention. The invention also contemplates transgenic non-human mammals whose germ cells and somatic cells contain a recombinant molecule comprising a nucleic acid molecule of the invention, in particular one which encodes an analog of the KLK15 Protein, or a truncation of the KLK15 Protein.

The invention further provides a method for preparing KLK15 Related Proteins utilizing the purified and isolated nucleic acid molecules of the invention. In an embodiment a method for preparing a KLK15 Related Protein is provided comprising (a) transferring a recombinant expression vector of the invention into a host cell; (b) selecting transformed host cells from untransformed host cells; (c) culturing a selected transformed host cell under conditions which allow expression of the KLK15 Related Protein; and (d) isolating the KLK15 Related Protein.

The invention further broadly contemplates an isolated KLK15 Protein comprising an amino acid sequence of SEQ.ID.NO. 6, 7, 8, or 9.

The KLK15 Related Proteins of the invention may be conjugated with other molecules, such as proteins, to prepare fusion proteins. This may be accomplished, for example, by the synthesis of N-terminal or C-terminal fusion proteins.

The invention further contemplates antibodies having specificity against an epitope of a KLK15 Related Protein of the invention. Antibodies may be labeled with a detectable substance and used to detect proteins of the invention in tissues and cells. Antibodies may have particular use in therapeutic applications, for example to react with tumor cells, and in conjugates and immunotoxins as target selective carriers of various agents which have antitumor effects including chemotherapeutic drugs, toxins, immunological response modifiers, enzymes, and radioisotopes.

The invention also permits the construction of nucleotide probes that are unique to the nucleic acid molecules of the invention and/or to proteins of the invention. Therefore, the invention also relates to a probe comprising a nucleic acid sequence of the invention, or a nucleic acid sequence encoding a protein of the invention, or a part thereof. The probe may be labeled, for example, with a detectable substance and it may be used to select from a mixture of nucleotide sequences a nucleic acid molecule of the invention including nucleic acid molecules coding for a protein which displays one or more of the properties of a protein of the invention. A probe may be used to mark tumors.

The invention also provides antisense nucleic acid molecules e.g. by production of a mRNA or DNA strand in the reverse orientation to a sense molecule. An antisense nucleic acid molecule may be used to suppress the growth of a KLK15 expressing (e.g. cancerous) cell.

The invention still further provides a method for identifying a substance that binds to a protein of the invention comprising reacting the protein with at least one substance which potentially can bind with the protein, under conditions which permit the formation of complexes between the substance and protein and detecting binding. Binding may be detected by assaying for complexes, for free substance, or for non-complexed protein. The invention also contemplates methods for identifying substances that bind to other intracellular proteins that interact with a KLK15 Related Protein. Methods can also be utilized which identify compounds which bind to KLK15 gene regulatory sequences (e.g. promoter sequences).

Still further the invention provides a method for evaluating a compound for its ability to modulate the biological activity of a KLK15 Related Protein of the invention. For example a substance which inhibits or enhances the interaction of the protein and a substance which binds to the protein may be evaluated. In an embodiment, the method comprises providing a known concentration of a KLK15 Related Protein, with a substance which binds to the protein and a test compound under conditions which permit the formation of complexes between the substance and protein, and removing and/or detecting complexes.

Compounds which modulate the biological activity of a protein of the invention may also be identified using the methods of the invention by comparing the pattern and level of expression of the protein of the invention in tissues and cells, in the presence, and in the absence of the compounds.

The proteins of the invention, antibodies, antisense nucleic acid molecules, and substances and compounds identified using the methods of the invention, and peptides of the invention may be used to modulate the biological activity of a KLK15 Related Protein of the invention, and they may be used in the treatment of conditions such as cancer (particularly prostate, colon, kidney, and testicular cancer) and thyroid disorders in a subject. Accordingly, the substances and compounds may be formulated into compositions for administration to individuals suffering from disorders such as cancer (particularly prostate, colon, kidney, and testicular cancer) and thyroid disorders in a subject. In particular, the antibodies, antisense nucleic acid molecules, substances and compounds may be used to treat patients who have a KLK15 Related Protein in, or on, their cancer cells.

Therefore, the present invention also relates to a composition comprising one or more of a protein of the invention, or a substance or compound identified using the methods of the invention, and a pharmaceutically acceptable carrier, excipient or diluent. A method for treating or preventing a disorder such as cancer (particularly prostate, thyroid, colon, kidney, and testicular cancer) and thyroid disorders in a subject is also provided comprising administering to a patient in need thereof, a KLK15 Related Protein of the invention, a substance or compound identified using the methods of the invention, or a composition of the invention.

Another aspect of the invention is the use of a KLK15 Related Protein, peptides derived therefrom, or chemically produced (synthetic) peptides, or any combination of these molecules, for use in the preparation of vaccines to prevent cancer and/or to treat cancer, in particular to prevent and/or treat cancer in patients who have a KLK15 Related Protein detected on their cells. These vaccine preparations may also be used to prevent patients from having tumors prior to their occurrence.

The invention broadly contemplates vaccines for stimulating or enhancing in a subject to whom the vaccine is administered production of antibodies directed against a KLK15 Related Protein.

The invention also provides a method for stimulating or enhancing in a subject production of antibodies directed against a KLK15 Related Protein. The method comprises administering to the subject a vaccine of the invention in a dose effective for stimulating or enhancing production of the antibodies.

The invention further provides methods for treating, preventing, or delaying recurrence of cancer. The methods comprise administering to the subject a vaccine of the invention in a dose effective for treating, preventing, or delaying recurrence of cancer.

In other embodiments, the invention provides a method for identifying inhibitors of a KLK15 Related Protein interaction, comprising
  (a) providing a reaction mixture including the KLK15 Related Protein and a substance that binds to the KLK15 Related Protein, or at least a portion of each which interact;
  (b) contacting the reaction mixture with one or more test compounds;
  (c) identifying compounds which inhibit the interaction of the KLK15 Related Protein and substance.

In certain preferred embodiments, the reaction mixture is a whole cell. In other embodiments, the reaction mixture is a cell lysate or purified protein composition. The subject method can be carried out using libraries of test compounds. Such agents can be proteins, peptides, nucleic acids, carbohydrates, small organic molecules, and natural product extract libraries, such as those isolated from animals, plants, fungus and/or microbes.

Still another aspect of the present invention provides a method of conducting a drug discovery business comprising:
  (a) providing one or more assay systems for identifying agents by their ability to inhibit or potentiate the interaction of a KLK15 Related Protein and a substance that binds to the protein;
  (b) conducting therapeutic profiling of agents identified in step (a), or further analogs thereof, for efficacy and toxicity in animals; and
  (c) formulating a pharmaceutical preparation including one or more agents identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 shows the genomic organization and partial genomic sequence of the KLK15 gene. Intronic sequences are not shown except for the splice junction areas. Introns are shown with lower case letters and exons with capital letters. The coding nucleotides are shown in bold and the 3' untranslated region follows the TGA stop codon (encircled). The translated amino acids of the coding region are shown underneath by a single letter abbreviation. The start and stop codons are encircled and the exon-intron junctions are underlined. The catalytic residues are boxed. The putative polyadenylation signal is underlined. The exact start of the first coding exon was not determined.

FIG. 2 shows an alignment of the deduced amino acid sequence of KLK15 with members of the kallikrein multigene family (SEQ ID NOs. 25-38). Dashes represent gaps to bring the sequences to better alignment. The residues of the catalytic triad (H, D, S) are shown in italics. Identical amino acids are highlighted in black and similar residues in grey. The 29 invariant serine protease residues are marked by (●) on the bottom, and the cysteine residues by (+) on top of each block. The predicted cleavage sites of the signal and activation peptides are indicated by arrows. The dotted area represents the kallikrein loop sequence. The trypsin-like cleavage pattern predicted by the presence of the "D" residue is indicated by (*). KLK15 has an "E" in this position. A unique 8 amino acid sequence, HNEPGTAG (SEQ ID NO. 10), is present at positions 148-155 of the KLK15 gene.

DETAILED DESCRIPTION OF THE INVENTION

Figure 3:
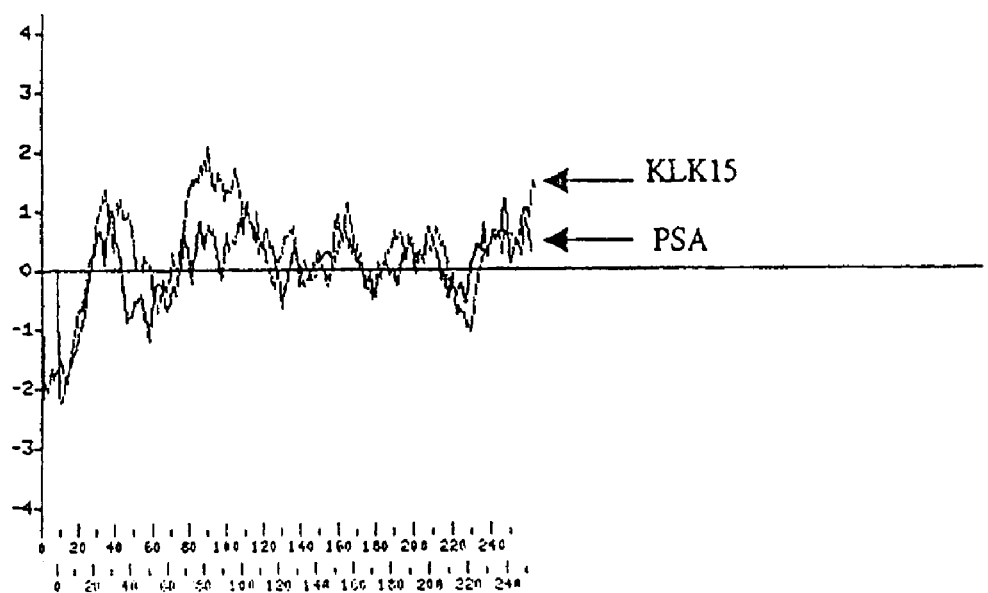
FIG. 3 is a plot of hydrophobicity and hydrophilicity of the KLK15 protein, as compared with the prostate specific antigen (PSA). Note the hydrophobic region at the amino terminus, suggesting presence of a signal peptide.

In accordance with the present invention there may be employed conventional molecular biology, microbiology, and recombinant DNA techniques within the skill of the art. Such techniques are explained fully in the literature. See for example, Sambrook, Fritsch, & Maniatis, Molecular Cloning: A Laboratory Manual, Second Edition (1989) Cold Spring Harbor Laboratory Press, Cold Spring Harbor, N.Y); DNA Cloning: A Practical Approach, Volumes I and II (D. N. Glover ed. 1985); Oligonucleotide Synthesis (M. J. Gait ed. 1984); Nucleic Acid Hybridization B. D. Hames & S. J. Higgins eds. (1985); Transcription and Translation B. D. Hames & S. J. Higgins eds (1984); Animal-Cell Culture R. I. Freshney, ed. (1986); Immobilized Cells and enzymes IRL Press, (1986); and B. Perbal, A Practical Guide to Molecular Cloning (1984).

1. Nucleic Acid Molecules of the Invention

As hereinbefore mentioned, the invention provides an isolated nucleic acid molecule having a sequence encoding a KLK15 Protein. The term "isolated" refers to a nucleic acid substantially free of cellular material or culture medium when produced by recombinant DNA techniques, or chemical reactants, or other chemicals when chemically synthesized. An "isolated" nucleic acid may also be free of sequences which naturally flank the nucleic acid (i.e., sequences located at the 5' and 3' ends of the nucleic acid molecule) from which the nucleic acid is derived. The term "nucleic acid" is intended to include DNA and RNA and can be either double stranded or single stranded. In an embodiment, a nucleic acid molecule of the invention encodes a protein comprising an amino acid sequence of SEQ.ID.NO. 6, 7, 8, or 9 preferably a nucleic acid molecule of the invention comprises a nucleic acid sequence of one or more of SEQ.ID.NO. 1 through 5, or 10 through 24.

In an embodiment, the invention provides an isolated nucleic acid molecule which comprises:

(i) a nucleic acid sequence encoding a protein having substantial sequence identity with an amino acid sequence of SEQ. ID. NO. 6, 7, 8, or 9;
(ii) a nucleic acid sequence encoding a protein comprising an amino acid sequence of SEQ. ID. NO. 6, 7, 8, or 9;
(iii) nucleic acid sequences complementary to (i) or (ii);
(iv) a degenerate form of a nucleic acid sequence of (i) or (ii);
(v) a nucleic acid sequence capable of hybridizing under stringent conditions to a nucleic acid sequence in (i), (ii) or (iii);
(vi) a nucleic acid sequence encoding a truncation, an analog, an allelic or species variation of a protein comprising an amino acid sequence of SEQ. ID. NO. 6, 7, 8, or 9; or
(vii) a fragment, or allelic or species variation of (i), (ii) or (iii).

Preferably, a purified and isolated nucleic acid molecule of the invention comprises:
(i) a nucleic acid sequence comprising the sequence of one or more of SEQ.ID.NO. 1 through 5 or 10 through 24, wherein T can also be U;
(ii) nucleic acid sequences complementary to (i), preferably complementary to the full nucleic acid sequence of one or more of SEQ.ID.NO. 1 through 5 or 10 through 24;
(iii) a nucleic acid capable of hybridizing under stringent conditions to a nucleic acid of (i) or (ii) and preferably having at least 18 nucleotides; or
(iv) a nucleic acid molecule differing from any of the nucleic acids of (i) to (iii) in codon sequences due to the degeneracy of the genetic code.

The invention includes nucleic acid sequences complementary to a nucleic acid encoding a protein comprising an amino acid sequence of SEQ.ID.NO. 6, 7, 8, or 9 preferably the nucleic acid sequences complementary to a full nucleic acid sequence of one or more of SEQ.ID.NO. 1 through 5 or 10 through 24.

The invention includes nucleic acid molecules having substantial sequence identity or homology to nucleic acid sequences of the invention or encoding proteins having substantial identity or similarity to the amino acid sequence of SEQ.ID.NO. 6, 7, 8, or 9. Preferably, the nucleic acids have substantial sequence identity for example at least 50%, 55%, 60%, 65%, 70%, 75%, 80%, or 85% nucleic acid identity; more preferably 90% nucleic acid identity; and most preferably at least 95%, 96%, 97%, 98%, or 99% sequence identity. "Identity" as known in the art and used herein, is a relationship between two or more amino acid sequences or two or more nucleic acid sequences, as determined by comparing the sequences. It also refers to the degree of sequence relatedness between amino acid or nucleic acid sequences, as the case may be, as determined by the match between strings of such sequences. Identity and similarity are well known terms to skilled artisans and they can be calculated by conventional methods (for example see Computational Molecular Biology, Lesk, A. M. ed., Oxford University Press, New York, 1988; Biocomputing: Informatics and Genome Projects, Smith, D. W. ed., Academic Press, New York, 1993; Computer Analysis of Sequence Data, Part I, Griffin, A. M. and Griffin, H. G. eds., Humana Press, New Jersey, 1994; Sequence Analysis in Molecular Biology, von Heinje, G. Academic Press, 1987; and Sequence Analysis Primer, Gribskov, M. and Devereux, J. eds. M. Stockton Press, New York, 1991, Carillo, H. and Lipman, D., SIAM J. Applied Math. 48:1073, 1988). Methods which are designed to give the largest match between the sequences are generally preferred. Methods to determine identity and similarity are codified in publicly available computer programs including the GCG program package (Devereux J. et al., Nucleic Acids Research 12(1): 387, 1984); BLASTP, BLASTN, and FASTA (Altschul, S. F. et al. J. Molec. Biol. 215: 403-410, 1990). The BLAST X program is publicly available from NCBI and other sources (BLAST Manual, Altschul, S. et al. NCBI NLM NIH Bethesda, Md. 20894; Altschul, S. et al. J. Mol. Biol. 215: 403-410, 1990).

Isolated nucleic acid molecules encoding a KLK15 Protein, and having a sequence which differs from a nucleic acid sequence of the invention due to degeneracy in the genetic code are also within the scope of the invention. Such nucleic acids encode functionally equivalent proteins (e.g. a KLK15 Protein) but differ in sequence from the sequence of a KLK15 Protein due to degeneracy in the genetic code. As one example, DNA sequence polymorphisms within the nucleotide sequence of a KLK15 Protein may result in silent mutations which do not affect the amino acid sequence. Variations in one or more nucleotides may exist among individuals within a population due to natural allelic variation. Any and all such nucleic acid variations are within the scope of the invention. DNA sequence polymorphisms may also occur which lead to changes in the amino acid sequence of a KLK15 Protein. These amino acid polymorphisms are also within the scope of the present invention.

Another aspect of the invention provides a nucleic acid molecule which hybridizes under stringent conditions, preferably high stringency conditions to a nucleic acid molecule which comprises a sequence which encodes a KLK15 Protein having an amino acid sequence shown in SEQ.ID.NO. 6, 7, 8, or 9. Appropriate stringency conditions which promote DNA hybridization are known to those skilled in the art, or can be found in Current Protocols in Molecular Biology, John Wiley & Sons, N.Y. (1989), 6.3.1-6.3.6. For example, 6.0× sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

It will be appreciated that the invention includes nucleic acid molecules encoding a KLK15 Related Protein including truncations of a KLK15 Protein, and analogs of a KLK15 Protein as described herein. The truncated nucleic acids or nucleic acid fragments may correspond to a sequence comprising or consisting of nucleotides 1581-1623, 1524-5258, 5259-5412, 5413-5912, 5913-6078, 6197-6316, 6079-6316, 6317-6453, 6454-7126, 6079-7126, 7127-7786, 5913-6196, 7127-7131, or 7127-7279 of SEQ ID NO. 1, or SEQ ID NO. 39, 47, 48, 49, or 50. It will further be appreciated that variant forms of the nucleic acid molecules of the invention which arise by alternative splicing of an mRNA corresponding to a cDNA of the invention are encompassed by the invention (See SEQ ID NO. 3, 4, and 5).

An isolated nucleic acid molecule of the invention which comprises DNA can be isolated by preparing a labelled nucleic acid probe based on all or part of a nucleic acid sequence of the invention. The labeled nucleic acid probe is used to screen an appropriate DNA library (e.g. a cDNA or genomic DNA library). For example, a cDNA library can be used to isolate a cDNA encoding a KLK15 Related Protein by screening the library with the labeled probe using standard techniques. Alternatively, a genomic DNA library can be similarly screened to isolate a genomic clone encompassing a gene encoding a KLK15 Related Protein. Nucleic acids isolated by screening of a cDNA or genomic DNA library can be sequenced by standard techniques.

An isolated nucleic acid molecule of the invention which is DNA can also be isolated by selectively amplifying a nucleic acid encoding a KLK15 Related Protein using the polymerase chain reaction (PCR) methods and cDNA or genomic DNA. It is possible to design synthetic oligonucleotide primers from the nucleotide sequence of the invention for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a KLK15 Related Protein into an appropriate vector which allows for transcription of the cDNA to produce an RNA molecule which encodes a KLK15 Related Protein. For example, a cDNA can be cloned downstream of a bacteriophage promoter, (e.g. a T7 promoter) in a vector, cDNA can be transcribed in vitro with T7 polymerase, and the resultant RNA can be isolated by conventional techniques.

Nucleic acid molecules of the invention may be chemically synthesized using standard techniques. Methods of chemically synthesizing polydeoxynucleotides are known, including but not limited to solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a KLK15 Related Protein can be accomplished by, expressing the cDNA in an appropriate host cell by standard techniques, and testing the expressed protein in the methods described herein. A cDNA encoding a KLK15 Related Protein can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of a KLK15 Related Protein may be determined using computer software designed for the purpose, such as PC/Gene (Intelli-Genetics Inc., Calif.). The intron-exon structure and the transcription regulatory sequences of a gene encoding a KLK15 Related Protein may be confirmed by using a nucleic acid molecule of the invention encoding a KLK15 Related Protein to probe a genomic DNA clone library. Regulatory elements can be identified using standard techniques. The function of the elements can be confirmed by using these elements to express a reporter gene such as the lacZ gene that is operatively linked to the elements. These constructs may be introduced into cultured cells using conventional procedures or into non-human transgenic animal models. In addition to identifying regulatory elements in DNA, such constructs may also be used to identify nuclear proteins interacting with the elements, using techniques known in the art. In an embodiment, regulatory sequences of a nucleic acid molecule of the invention comprise the sequence of SEQ ID NO.11.

In a particular embodiment of the invention, the nucleic acid molecules isolated using the methods described herein are mutant KLK15 gene alleles. The mutant alleles may be isolated from individuals either known or proposed to have a genotype which contributes to the symptoms of a disorder involving a KLK15 Related Protein. Mutant alleles and mutant allele products may be used in therapeutic and diagnostic methods described herein. For example, a cDNA of a mutant KLK15 gene may be isolated using PCR as described herein, and the DNA sequence of the mutant allele may be compared to the normal allele to ascertain the mutation(s) responsible for the loss or alteration of function of the mutant gene product. A genomic library can also be constructed using DNA from an individual suspected of or known to carry a mutant allele, or a cDNA library can be constructed using RNA from tissue known, or suspected to express the mutant allele. A nucleic acid encoding a normal KLK15 gene or any suitable fragment thereof, may then be labeled and used as a probe to identify the corresponding mutant allele in such libraries. Clones containing mutant sequences can be purified and subjected to sequence analysis. In addition, an expression library can be constructed using cDNA from RNA isolated from a tissue of an individual known or suspected to express a mutant KLK15 allele. Gene products made by the putatively mutant tissue may be expressed and screened, for example using antibodies specific for a KLK15 Related Protein as described herein. Library clones identified using the antibodies can be purified and subjected to sequence analysis.

The sequence of a nucleic acid molecule of the invention, or a fragment of the molecule, may be inverted relative to its normal presentation for transcription to produce an antisense nucleic acid molecule. An antisense nucleic acid molecule may be constructed using chemical synthesis and enzymatic ligation reactions using procedures known in the art.

2. Proteins of the Invention

An amino acid sequence of a KLK15 Protein comprises a sequence as shown in SEQ.ID.NO. 6, 7, 8, or 9. The protein is primarily expressed in the thyroid gland, and to a lower extent in the prostate, salivary and adrenal glands, colon, testis, and kidney.

In addition to proteins comprising an amino acid sequence as shown in SEQ.ID.NO. 6, 7, 8, or 9, the proteins of the present invention include truncations of a KLK15 Protein, analogs of a KLK15 Protein, and proteins having sequence identity or similarity to a KLK15 Protein, and truncations thereof as described herein (i.e. KLK15 Related Proteins).

Truncated proteins may comprise peptides of between 3 and 70 amino acid residues, ranging in size from a tripeptide to a 70 mer polypeptide. In a preferred embodiment the peptide is HNEPGTAG (SEQ ID NO 10). The truncated proteins may have an amino group (—NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated proteins may have a carboxyl group, an amido group, a T-butyloxycarbonyl group, or a macromolecule including but not limited to lipid-fatty acid conjugates, polyethylene glycol, or carbohydrates at the carboxy terminal end.

The proteins of the invention may also include analogs of a KLK15 Protein, and/or truncations thereof as described herein, which may include, but are not limited to a KLK15 protein, containing one or more amino acid substitutions, insertions, and/or deletions. Amino acid substitutions may be of a conserved or non-conserved nature. Conserved amino acid substitutions involve replacing one or more amino acids of a KLK15 Protein amino acid sequence with amino acids of similar charge, size, and/or hydrophobicity characteristics. When only conserved substitutions are made the resulting analog is preferably functionally equivalent to a KLK15 Protein. Non-conserved substitutions involve replacing one or more amino acids of the KLK15 Protein amino acid sequence with one or more amino acids that possess dissimilar charge, size, and/or hydrophobicity characteristics.

One or more amino acid insertions may be introduced into a KLK15 Protein. Amino acid insertions may consist of single amino acid residues or sequential amino acids ranging from 2 to 15 amino acids in length.

Deletions may consist of the removal of one or more amino acids, or discrete portions from a KLK15 Protein sequence. The deleted amino acids may or may not be contiguous. The lower limit length of the resulting analog with a deletion mutation is about 10 amino acids, preferably 20 to 40 amino acids.

The proteins of the invention include proteins with sequence identity or similarity to a KLK15 Protein and/or truncations thereof as described herein. Such KLK15 Proteins include proteins whose amino acid sequences are comprised of the amino acid sequences of KLK15 Protein regions from other species that hybridize under selected hybridization conditions (see discussion of stringent hybridization conditions herein) with a probe used to obtain a KLK15 Protein. These proteins will generally have the same regions which are characteristic of a KLK15 Protein. Preferably a protein will have substantial sequence identity for example, about 55%, 60%, 65%, 70%, 75%, 80%, or 85% identity, preferably 90% identity, more preferably at least 95%, 96%, 97%, 98%, or 99% identity, and most preferably 98% identity with an amino acid sequence of SEQ.ID.NO. 6, 7, 8, or 9. A percent amino acid sequence homology, similarity or identity is calculated as the percentage of aligned amino acids that match the reference sequence using known methods as described herein.

The invention also contemplates isoforms of the proteins of the invention. An isoform contains the same number and kinds of amino acids as a protein of the invention, but the isoform has a different molecular structure. Isoforms contemplated by the present invention preferably have the same properties as a protein of the invention as described herein.

The present invention also includes KLK15 Related Proteins conjugated with a selected protein, or a marker protein (see below) to produce fusion proteins. Additionally, immunogenic portions of a KLK15 Protein and a KLK15 Protein Related Protein are within the scope of the invention.

A KLK15 Related Protein of the invention may be prepared using recombinant DNA methods. Accordingly, the nucleic acid molecules of the present invention having a sequence which encodes a KLK15 Related Protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used.

The invention therefore contemplates a recombinant expression vector of the invention containing a nucleic acid molecule of the invention, and the necessary regulatory sequences for the transcription and translation of the inserted protein-sequence. Suitable regulatory sequences may be derived from a variety of sources, including bacterial, fungal, viral, mammalian, or insect genes [For example, see the regulatory sequences described in Goeddel, Gene Expression Technology: Methods in Enzymology 185, Academic Press, San Diego, Calif. (1990)]. Selection of appropriate regulatory sequences is dependent on the host cell chosen as discussed below, and may be readily accomplished by one of ordinary skill in the art. The necessary regulatory sequences may be supplied by the native KLK15 Protein and/or its flanking regions.

The invention further provides a recombinant expression vector comprising a DNA nucleic acid molecule of the invention cloned into the expression vector in an antisense orientation. That is, the DNA molecule is linked to a regulatory sequence in a manner which allows for expression, by transcription of the DNA molecule, of an RNA molecule which is antisense to the nucleic acid sequence of a protein of the invention or a fragment thereof. Regulatory sequences linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA.

The recombinant expression vectors of the invention may also contain a marker gene which facilitates the selection of host cells transformed or transfected with a recombinant molecule of the invention. Examples of marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin, preferably IgG. The markers can be introduced on a separate vector from the nucleic acid of interest.

The recombinant expression vectors may also contain genes that encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

The recombinant expression vectors may be introduced into host cells to produce a transformant host cell. "Transformant host cells" include host cells which have been transformed or transfected with a recombinant expression vector of the invention. The terms "transformed with", "transfected with", "transformation" and "transfection" encompass the introduction of a nucleic acid (e.g. a vector) into a cell by one of many standard techniques. Prokaryotic cells can be transformed with a nucleic acid by, for example, electroporation or calcium-chloride mediated transformation. A nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as E. coli, insect cells (using baculovirus), yeast cells, or mammalian cells. Other suitable host cells can be found in Goeddel, Gene Expression Technology: Methods in Enzymology 185, Academic Press, San Diego, Calif. (1991).

A host cell may also be chosen which modulates the expression of an inserted nucleic acid sequence, or modifies (e.g. glycosylation or phosphorylation) and processes (e.g. cleaves) the protein in a desired fashion. Host systems or cell lines may be selected which have specific and characteristic mechanisms for post-translational processing and modification of proteins. For example, eukaryotic host cells including CHO, VERO, BHK, HeLA, COS, MDCK, 293, 3T3, and W138 may be used. For long-term high-yield stable expression of the protein, cell lines and host systems which stably express the gene product may be engineered.

Host cells and in particular cell lines produced using the methods described herein may be particularly useful in screening and evaluating compounds that modulate the activity of a KLK15 Related Protein.

The proteins of the invention may also be expressed in non-human transgenic animals including but not limited to mice, rats, rabbits, guinea pigs, micro-pigs, goats, sheep, pigs, non-human primates (e.g. baboons, monkeys, and chimpanzees) [see Hammer et al. (Nature 315:680-683, 1985), Palmiter et al. (Science 222:809-814, 1983), Brinster et al. (Proc Natl. Acad. Sci USA 82:4438-4442,1985), Palmiter and Brinster (Cell. 41:343-345, 1985) and U.S. Pat. No. 4,736,866)]. Procedures known in the art may be used to introduce a nucleic acid molecule of the invention encoding a KLK15 Related Protein into animals to produce the founder lines of transgenic animals. Such procedures include pronuclear microinjection, retrovirus mediated gene transfer into germ lines, gene targeting in embryonic stem cells, electroporation of embryos, and sperm-mediated gene transfer.

The present invention contemplates a transgenic animal that carries the KLK15 gene in all their cells, and animals which carry the transgene in some but not all their cells. The transgene may be integrated as a single transgene or in concatamers. The transgene may be selectively introduced into and activated in specific cell types (See for example, Lasko et al, 1992 Proc. Natl. Acad. Sci. USA 89: 6236). The transgene may be integrated into the chromosomal site of the endogenous gene by gene targeting. The transgene may be selectively introduced into a particular cell type inactivating the endogenous gene in that cell type (See Gu et al Science 265: 103-106).

The expression of a recombinant KLK15 Related Protein in a transgenic animal may be assayed using standard techniques. Initial screening may be conducted by Southern Blot analysis, or PCR methods to analyze whether the transgene has been integrated. The level of mRNA expression in the tissues of transgenic animals may also be assessed using techniques including Northern blot analysis of tissue samples, in situ hybridization, and RT-PCR. Tissue may also be evaluated immunocytochemically using antibodies against KLK15 Protein.

Proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

N-terminal or C-terminal fusion proteins comprising a KLK15 Related Protein of the invention conjugated with other molecules, such as proteins, may be prepared by fusing, through recombinant techniques, the N-terminal or C-terminal of a KLK15 Related Protein, and the sequence of a selected protein or marker protein with a desired biological function. The resultant fusion proteins contain a KLK15 Protein fused to the selected protein or marker protein as described herein. Examples of proteins which may be used to prepare fusion proteins include immunoglobulins, glutathione-S-transferase (GST), hemagglutinin (HA), and truncated myc.

3. Antibodies

KLK15 Related Proteins of the invention can be used to prepare antibodies specific for the proteins. Antibodies can be prepared which bind a distinct epitope in an unconserved region of the protein. An unconserved region of the protein is one that does not have substantial sequence homology to other proteins. A region from a conserved region such as a well-characterized domain can also be used to prepare an antibody to a conserved region of a KLK15 Related Protein. Antibodies having specificity for a KLK15 Related Protein may also be raised from fusion proteins created by expressing fusion proteins in bacteria as described herein.

The invention can employ intact monoclonal or polyclonal antibodies, and immunologically active fragments (e.g. a Fab, (Fab)$_2$ fragment, or Fab expression library fragments and epitope-binding fragments thereof), an antibody heavy chain, and antibody light chain, a genetically engineered single chain Fv molecule (Ladner et al, U.S. Pat. No. 4,946,778), humanized antibody, or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

4. Applications of the Nucleic Acid Molecules, KLK15 Related Proteins, and Antibodies of the Invention The nucleic acid molecules, KLK15 Related Proteins, and antibodies of the invention may be used in the prognostic and diagnostic evaluation of disorders involving a KLK15 Related Protein (e.g. cancer or thyroid disorders), and the identification of subjects with a predisposition to such disorders (Section 4.1.1 and 4.1.2).

In an embodiment of the invention, a method is provided for detecting the expression of the cancer marker KLK15 in a patient comprising:
   (a) taking a sample derived from a patient; and
   (b) detecting in the sample a nucleic acid sequence encoding KLK15 or a protein product encoded by a KLK15 nucleic acid sequence.

In a particular embodiment of the invention, the nucleic acid molecules, KLK15 Related Proteins, and antibodies of the invention may be used in the diagnosis and staging of cancer, in particular prostate cancer. Increased levels of KLK15 Related Proteins are associated with more aggressive forms of prostate cancer and may be an indicator of poor prognosis.

Methods for detecting nucleic acid molecules and KLK15 Related Proteins of the invention can be used to monitor disorders involving a KLK15 Related Protein by detecting KLK15 Related Proteins and nucleic acid molecules encoding KLK15 Related Proteins. The applications of the present invention also include methods for the identification of compounds that modulate the biological activity of KLK15 Related Proteins (Section 4.2). The compounds, antibodies etc. may be used for the treatment of disorders involving a KLK15 Related Protein (Section 4.3). It would also be apparent to one skilled in the art that the methods described herein may be used to study the developmental expression of KLK15 Related Proteins and, accordingly, will provide further insight into the role of KLK15 Related Proteins.

4.1 Diagnostic Methods

A variety of methods can be employed for the diagnostic and prognostic evaluation of disorders involving a KLK15 Related Protein, and the identification of subjects with a predisposition to such disorders. Such methods may, for example, utilize nucleic acid molecules of the invention, and fragments thereof, and antibodies directed against KLK15 Related Proteins, including peptide fragments. In particular, the nucleic acids and antibodies may be used, for example, for: (1) the detection of the presence of KLK15 mutations, or the detection of either over- or under-expression of KLK15 mRNA relative to a non-disorder state or the qualitative or quantitative detection of alternatively spliced forms of KLK15 transcripts which may correlate with certain conditions or susceptibility toward such conditions; and (2) the detection of either an over- or an under-abundance of KLK15 Related Proteins relative to a non- disorder state or the presence of a modified (e.g., less than full length) KLK15 Protein which correlates with a disorder state, or a progression toward a disorder state.

The methods described herein may be used to evaluate the probability of the presence of malignant or pre-malignant cells, for example, in a group of cells freshly removed from a host. Such methods can be used to detect tumors, quantitate their growth, and help in the diagnosis and prognosis of disease. The methods can be used to detect the presence of cancer metastasis, as well as confirm the absence or removal of all tumor tissue following surgery, cancer chemotherapy, and/or radiation therapy. They can further be used to monitor cancer chemotherapy and tumor reappearance.

The methods described herein may be performed by utilizing pre-packaged diagnostic kits comprising at least one specific KLK15 nucleic acid or antibody described herein, which may be conveniently used, e.g., in clinical settings, to screen and diagnose patients and to screen and identify those individuals exhibiting a predisposition to developing a disorder.

Nucleic acid-based detection techniques are described, below, in Section 4.1.1. Peptide detection techniques are described, below, in Section 4.1.2. The samples that may be analyzed using the methods of the invention include those which are known or suspected to express KLK15 or contain KLK15 Related Proteins. The samples may be derived from a patient or a cell culture, and include but are not limited to biological fluids, tissue extracts, freshly harvested cells, and lysates of cells which have been incubated in cell cultures.

Oligonucleotides or longer fragments derived from any of the nucleic acid molecules of the invention may be used as targets in a microarray. The microarray can be used to simultaneously monitor the expression levels of large numbers of genes and to identify genetic variants, mutations, and polymorphisms. The information from the microarray may be used to determine gene function, to understand the genetic basis of a disorder, to diagnose a disorder, and to develop and monitor the activities of therapeutic agents.

The preparation, use, and analysis of microarrays are well known to a person skilled in the art. (See, for example, Brennan, T. M. et al. (1995) U.S. Pat. No. 5,474,796; Schena, et al. (1996) Proc. Natl. Acad. Sci. 93:10614-10619; Baldeschweiler et al. (1995), PCT Application WO95/251116; Shalon, D. et al. (1995) PCT application WO95/35505; Heller, R. A. et al. (1997) Proc. Natl. Acad. Sci. 94:2150-2155; and Heller, M. J. et al. (1997) U.S. Pat. No. 5,605,662.)

4.1.1 Methods for Detecting Nucleic Acid Molecules of the Invention

The nucleic acid molecules of the invention allow those skilled in the art to construct nucleotide probes for use in the detection of nucleic acid sequences of the invention in samples. Suitable probes include nucleic acid molecules based on nucleic acid sequences encoding at least 5 sequential amino acids from regions of the KLK15 Protein, preferably they comprise 15 to 30 nucleotides (see SEQ ID Nos. 47-50). A nucleotide probe may be labeled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, preferably in human cells, that encode KLK15 Related Proteins. The nucleotide probes may also be useful in the diagnosis of disorders involving a KLK15 Related Protein; in monitoring the progression of such disorders; or monitoring a therapeutic treatment.

The probe may be used in hybridization techniques to detect genes that encode KLK15 Related Proteins. The technique generally involves contacting and incubating nucleic acids (e.g. recombinant DNA molecules, cloned genes) obtained from a sample from a patient or other cellular source with a probe of the present invention under conditions favorable for the specific annealing of the probes to complementary sequences in the nucleic acids. After incubation, the non-annealed nucleic acids are removed, and the presence of nucleic acids that have hybridized to the probe if any are detected.

The detection of nucleic acid molecules of the invention may involve the amplification of specific gene sequences using an amplification method such as PCR, followed by the analysis of the amplified molecules using techniques known to those skilled in the art. Suitable primers can be routinely designed by one of skill in the art.

Genomic DNA may be used in hybridization or amplification assays of biological samples to detect abnormalities involving KLK15 structure, including point mutations, insertions, deletions, and chromosomal rearrangements. For example, direct sequencing, single stranded conformational polymorphism analyses, heteroduplex analysis, denaturing gradient gel electrophoresis, chemical mismatch cleavage, and oligonucleotide hybridization may be utilized.

Genotyping techniques known to one skilled in the art can be used to type polymorphisms that are in close proximity to the mutations in a klk15 gene. The polymorphisms may be used to identify individuals in families that are likely to carry mutations. If a polymorphism exhibits linkage disequalibrium with mutations in a KLK15 gene, it can also be used to screen for individuals in the general population likely to carry mutations. Polymorphisms which may be used include restriction fragment length polymorphisms (RFLPs), single-base polymorphisms, and simple sequence repeat polymorphisms (SSLPs).

A probe of the invention may be used to directly identify RFLPs. A probe or primer of the invention can additionally be used to isolate genomic clones such as YACs, BACs, PACs, cosmids, phage or plasmids. The DNA in the clones can be screened for SSLPs using hybridization or sequencing procedures.

Hybridization and amplification techniques described herein may be used to assay qualitative and quantitative aspects of klk15 expression. For example, RNA may be isolated from a cell type or tissue known to express klk15 and tested utilizing the hybridization (e.g. standard Northern analyses) or PCR techniques referred to herein. The techniques may be used to detect differences in transcript size which may be due to normal or abnormal alternative splicing. The techniques may be used to detect quantitative differences between levels of full length and/or alternatively splice transcripts detected in normal individuals relative to those individuals exhibiting symptoms of a disorder involving a KLK15 Related Protein.

The primers and probes may be used in the above described methods in situ i.e. directly on tissue sections (fixed and/or frozen) of patient tissue obtained from biopsies or resections.

4.1.2 Methods for Detecting KLK15 Related Proteins

Antibodies specifically reactive with a KLK15 Related Protein, or derivatives, such as enzyme conjugates or labeled derivatives, may be used to detect KLK15 Related Proteins in various samples (e.g. biological materials). They may be used as diagnostic or prognostic reagents and they may be used to detect abnormalities in the level of KLK15 Related Protein expression, or abnormalities in the structure, and/or temporal, tissue, cellular, or subcellular location of a KLK15 Related Protein. Antibodies may also be used to screen potentially therapeutic compounds in vitro to determine their effects on disorders involving a KLK15 Related Protein, and other conditions. In vitro immunoassays may also be used to assess or monitor the efficacy of particular therapies. The antibodies of the invention may also be used in vitro to determine the level of KLK15 expression in cells genetically engineered to produce a KLK15 Related Protein.

The antibodies may be used in any known immunoassays which rely on the binding interaction between an antigenic determinant of a KLK15 Related Protein and the antibodies. Examples of such assays are radioimmunoassays, enzyme immunoassays (e.g. ELISA), immunofluorescence, immunoprecipitation, latex agglutination, hemagglutination, and histochemical tests. The antibodies may be used to detect and quantify KLK15 Related Proteins in a sample in order to determine its role in particular cellular events or pathological states, and to diagnose and treat such pathological states.

In particular, the antibodies of the invention may be used in immuno-histochemical analyses, for example, at the cellular and sub-subcellular level, to detect a KLK15 Related Protein, to localize it to particular cells and tissues, and to specific subcellular locations, and to quantitate the level of expression.

Cytochemical techniques known in the art for localizing antigens using light and electron microscopy may be used to detect a KLK15 Related Protein. Generally, an antibody of the invention may be labeled with a detectable substance and a KLK15 Related Protein may be localised in tissues and cells based upon the presence of the detectable substance. Examples of detectable substances include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against KLK15 Related Protein. By way of example, if the antibody having specificity a KLK15 Related Protein is a rabbit IgG antibody, the second antibody may be goat anti-rabbit gamma-globulin labeled with a detectable substance as described herein.

Where a radioactive label is used as a detectable substance, a KLK15 Related Protein may be localized by radioautography. The results of radioautography may be quantitated by determining the density of particles in the radioautographs by various optical methods, or by counting the grains.

In an embodiment, the invention contemplates a method for monitoring the progression of cancer (e.g. prostate cancer) in an individual, comprising:
  (a) contacting an amount of an antibody which binds to a KLK15 Related Protein, with a sample from the individual so as to form a binary complex comprising the antibody and KLK15 Related Protein in the sample;
  (b) determining or detecting the presence or amount of complex formation in the sample;
  (c) repeating steps (a) and (b) at a point later in time; and
  (d) comparing the result of step (b) with the result of step (c), wherein a difference in the amount of complex formation is indicative of the progression of the cancer in said individual.

The amount of complexes may also be compared to a value representative of the amount of the complexes from an individual not at risk of, or afflicted with, cancer (e.g. prostate cancer).

4.2 Methods for Identifying or Evaluating Substances/Compounds

The methods described herein are designed to identify substances that modulate the biological activity of a KLK15 Related Protein including substances that bind to KLK15 Related Proteins, or bind to other proteins that interact with a KLK15 Related Protein, to compounds that interfere with, or enhance the interaction of a KLK15 Related Protein and substances that bind to the KLK15 Related Protein or other proteins that interact with a KLK15 Related Protein. Methods are also utilized that identify compounds that bind to KLK15 regulatory sequences.

The substances and compounds identified using the methods of the invention include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)2, and Fab expression library fragments, and epitope-binding fragments thereof)], and small organic or inorganic molecules. The substance or compound may be an endogenous physiological compound or it may be a natural or synthetic compound.

Substances which modulate a KLK15 Related Protein can be identified based on their ability to bind to a KLK15 Related Protein. Therefore, the invention also provides methods for identifying substances which bind to a KLK15 Related Protein. Substances identified using the methods of the invention may be isolated, cloned and sequenced using conventional techniques. A substance that associates with a polypeptide of the invention may be an agonist or antagonist of the biological or immunological activity of a polypeptide of the invention.

The term "agonist", refers to a molecule that increases the amount of, or prolongs the duration of, the activity of the protein. The term "antagonist" refers to a molecule which decreases the biological or immunological activity of the protein. Agonists and antagonists may include proteins, nucleic acids, carbohydrates, or any other molecules that associate with a protein of the invention.

Substances which can bind with a KLK15 Related Protein may be identified by reacting a KLK15 Related Protein with a test substance which potentially binds to a KLK15 Related Protein, under conditions which permit the formation of substance-KLK15 Related Protein complexes and removing and/or detecting the complexes. The complexes can be detected by assaying for substance-KLK15 Related Protein complexes, for free substance, or for non-complexed KLK15 Related Protein. Conditions which permit the formation of substance-KLK15 Related Protein complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against KLK15 Related Protein or the substance, or labeled KLK15 Related Protein, or a labeled substance may be utilized. The antibodies, proteins, or substances may be labeled with a detectable substance as described above.

A KLK15 Related Protein, or the substance used in the method of the invention may be insolubilized. For example, a KLK15 Related Protein, or substance may be bound to a suitable carrier such as agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized protein or substance may be prepared by reacting the material with a suitable insoluble carrier using known chemical or physical methods, for example, cyanogen bromide coupling.

The invention also contemplates a method for evaluating a compound for its ability to modulate the biological activity of a KLK15 Related Protein of the invention, by assaying for an agonist or antagonist (i.e. enhancer or inhibitor) of the binding of a KLK15 Related Protein with a substance which binds with a KLK15 Related Protein. The basic method for evaluating if a compound is an agonist or antagonist of the binding of a KLK15 Related Protein and a substance that binds to the protein, is to prepare a reaction mixture containing the KLK15 Related Protein and the substance under conditions which permit the formation of substance-KLK15 Related Protein complexes, in the presence of a test compound. The test compound may be initially added to the mixture, or may be added subsequent to the addition of the KLK15 Related Protein and substance. Control reaction mixtures without the test compound or with a placebo are also prepared. The formation of complexes is detected and the formation of complexes in the control reaction but not in the reaction mixture indicates that the test compound interferes with the interaction of the KLK15 Related Protein and substance. The reactions may be carried out in the liquid phase or the KLK15 Related Protein, substance, or test compound may be immobilized as described herein. The ability of a compound to modulate the biological activity of a KLK15 Related Protein of the invention may be tested by determining the biological effects on cells.

It will be understood that the agonists and antagonists i.e. inhibitors and enhancers that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of the interaction of KLK15 Related Protein with a substance which is capable of binding to the KLK15 Related Protein. Thus, the invention may be used to assay for a compound that competes for the same binding site of a KLK15 Related Protein.

The invention also contemplates methods for identifying compounds that bind to proteins that interact with a KLK15 Related Protein. Protein-protein interactions may be identified using conventional methods such as co-immunoprecipitation, crosslinking and co-purification through gradients or chromatographic columns. Methods may also be employed that result in the simultaneous identification of genes which encode proteins interacting with a KLK15 Related Protein. These methods include probing expression libraries with labeled KLK15 Related Protein.

Two-hybrid systems may also be used to detect protein interactions in vivo. Generally, plasmids are constructed that encode two hybrid proteins. A first hybrid protein consists of the DNA-binding domain of a transcription activator protein fused to a KLK15 Related Protein, and the second hybrid protein consists of the transcription activator protein's activator domain fused to an unknown protein encoded by a cDNA which has been recombined into the plasmid as part of a cDNA library. The plasmids are transformed into a strain of yeast (e.g. *S. cerevisiae*) that contains a reporter gene (e.g. lacZ, luciferase, alkaline phosphatase, horseradish peroxidase) whose regulatory region contains the transcription activator's binding site. The hybrid proteins alone cannot activate the transcription of the reporter gene. However, interaction of the two hybrid proteins reconstitutes the functional activator protein and results in expression of the reporter gene, which is detected by an assay for the reporter gene product.

It will be appreciated that fusion proteins may be used in the above-described methods. In particular, KLK15 Related Proteins fused to a glutathione-S-transferase may be used in the methods.

A modulator of a KLK15 Related Protein of the invention may also be identified based on its ability to inhibit or enhance catalytic activity of the protein.

The reagents suitable for applying the methods of the invention to evaluate compounds that modulate a KLK15 Related Protein may be packaged into convenient kits providing the necessary materials packaged into suitable containers. The kits may also include suitable supports useful in performing the methods of the invention.

4.3 Compositions and Treatments

The proteins of the invention, substances or compounds identified by the methods described herein, antibodies, and nucleic acid molecules of the invention may be used for modulating the biological activity of a KLK15 Related Protein, and they may be used in the treatment of conditions such as cancer (particularly thyroid, prostate, colon, kidney, testicular cancer) and thyroid disorders in a patient.

Accordingly, the substances, antibodies, peptides, and compounds may be formulated into pharmaceutical compositions for administration to subjects in a biologically compatible form suitable for administration in vivo. By "biologically compatible form suitable for administration in vivo" is meant a form of the active substance to be administered in which any toxic effects are outweighed by the therapeutic effects. The active substances may be administered to living organisms including humans and animals. Administration of a therapeutically active amount of a pharmaceutical composition of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the substance from the action of enzymes, acids and other natural conditions that may inactivate the substance.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the active substances in association with one or more pharmaceutically acceptable vehicles or diluents, and contained in buffered solutions with a suitable pH and iso-osmotic with the physiological fluids.

The compositions are indicated as therapeutic agents either alone or in conjunction with other therapeutic agents or other forms of treatment (e.g. chemotherapy or radiotherapy). For example, the compositions may be used in combination with anti-proliferative agents, antimicrobial agents, immunostimulatory agents, or anti-inflammatories. In particular, the compounds may be used in combination with anti-viral and/ or anti-proliferative agents. The compositions of the invention may be administered concurrently, separately, or sequentially with other therapeutic agents or therapies.

Vectors derived from retroviruses, adenovirus, herpes or vaccinia viruses, or from various bacterial plasmids, may be used to deliver nucleic acid molecules to a targeted organ, tissue, or cell population. Methods well known to those skilled in the art may be used to construct recombinant vectors which will express antisense nucleic acid molecules of the invention. (See, for example, the techniques described in Sambrook et al (supra) and Ausubel et al (supra)).

The nucleic acid molecules comprising full length cDNA sequences and/or their regulatory elements enable a skilled artisan to use sequences encoding a protein of the invention as an investigative tool in sense (Youssoufian H and H F Lodish 1993 Mol Cell Biol 13:98-104) or antisense (Eguchi et al (1991) Annu Rev Biochem 60:631-652) regulation of gene function. Such technology is well known in the art, and sense or antisense oligomers, or larger fragments, can be designed from various locations along the coding or control regions.

Genes encoding a protein of the invention can be turned off by transfecting a cell or tissue with vectors which express high levels of a desired KLK15-encoding fragment. Such constructs can inundate cells with untranslatable sense or antisense sequences. Even in the absence of integration into the DNA, such vectors may continue to transcribe RNA molecules until all copies are disabled by endogenous nucleases.

Modifications of gene expression can be obtained by designing antisense molecules, DNA, RNA or PNA, to the regulatory regions of a gene encoding a protein of the invention, i.e., the promoters, enhancers, and introns. Preferably, oligonucleotides are derived from the transcription initiation site, e.g., between −10 and +10 regions of the leader sequence. The antisense molecules may also be designed so that they block translation of mRNA by preventing the transcript from binding to ribosomes. Inhibition may also be achieved using "triple helix" base-pairing methodology. Triple helix pairing compromises the ability of the double helix to open sufficiently for the binding of polymerases, transcription factors, or regulatory molecules. Therapeutic advances using triplex DNA were reviewed by Gee J E et al (In: Huber B E and B I Carr (1994) Molecular and Immunologic Approaches, Futura Publishing Co, Mt Kisco N.Y.).

Ribozymes are enzymatic RNA molecules that catalyze the specific cleavage of RNA. Ribozymes act by sequence-specific hybridization of the ribozyme molecule to complementary target RNA, followed by endonucleolytic cleavage. The invention therefore contemplates engineered hammerhead motif ribozyme molecules that can specifically and efficiently catalyze endonucleolytic cleavage of sequences encoding a protein of the invention.

Specific ribozyme cleavage sites within any potential RNA target may initially be identified by scanning the target molecule for ribozyme cleavage sites which include the following sequences, GUA, GUU and GUC. Once the sites are identified, short RNA sequences of between 15 and 20 ribonucleotides corresponding to the region of the target gene containing the cleavage site may be evaluated for secondary structural features which may render the oligonucleotide inoperable. The suitability of candidate targets may also be determined by testing accessibility to hybridization with complementary oligonucleotides using ribonuclease protection assays.

Methods for introducing vectors into cells or tissues include those methods discussed herein and which are suitable for in vivo, in vitro and ex vivo therapy. For ex vivo therapy, vectors may be introduced into stem cells obtained from a patient and clonally propagated for autologous transplant into the same patient (See U.S. Pat. Nos. 5,399,493 and 5,437,994). Delivery by transfection and by liposome is well known in the art.

An antibody against a KLK15 Related Protein may be conjugated to chemotherapeutic drugs, toxins, immunological response modifiers, hematogenous agents, enzymes, and radioisotopes and used in the prevention and treatment of cancer (e.g. thyroid, prostate, colon, kidney, testicular cancer). For example, an antibody against a KLK15 Related Protein may be conjugated to toxic moieties including but not limited to ricin A, diphtheria toxin, abrin, modeccin, or bacterial toxins from *Pseudomonas* or *Shigella*. Toxins and their derivatives have been reported to form conjugates with antibodies specific to particular target tissues, such as cancer or tumor cells in order to obtain specifically targeted cellular toxicity (Moolten F. L. et al, Immun. Rev. 62:47-72, 1982, and Bernhard, M. I. Cancer Res. 43:4420, 1983).

Conjugates can be prepared by standard means known in the art. A number of bifunctional linking agents (e.g. heterobifunctional linkers such as N-succinimidyl-3-(2-pyridyldithio)propionate) are available commercially from Pierce Chemically Company, Rockford, Ill.

Administration of the antibodies or immunotoxins for therapeutic use may be by an intravenous route, although with proper formulation additional routes of administration such as intraperitoneal, oral, or transdermal administration may also be used.

A KLK15 Related Protein may be conjugated to chemotherapeutic drugs, toxins, immunological response modifiers, enzymes, and radioisotopes using methods known in the art.

The invention also provides immunotherapeutic approaches for preventing or reducing the severity of a cancer. The clinical signs or symptoms of the cancer in a subject are indicative of a beneficial effect to the patient due to the stimulation of the subject's immune response against the cancer. Stimulating an immune response refers to inducing an immune response or enhancing the activity of immunoeffector cells in response to administration of a vaccine preparation of the invention. The prevention of a cancer can be indicated by an increased time before the appearance of cancer in a patient that is predisposed to developing cancer due for example to a genetic disposition or exposure to a carcinogenic agent. The reduction in the severity of a cancer can be indicated by a decrease in size or growth rate of a tumor.

Vaccines can be derived from a KLK Related Protein, peptides derived therefrom, or chemically produced synthetic peptides, or any combination of these molecules, or fusion proteins or peptides thereof. The proteins, peptides, etc. can be synthesized or prepared recombinantly or otherwise biologically, to comprise one or more amino acid sequences corresponding to one or more epitopes of a tumor associated protein. Epitopes of a tumor associated protein will be understood to include the possibility that in some instances amino acid sequence variations of a naturally occurring protein or polypeptide may be antigenic and confer protective immunity against cancer or anti-tumorigenic effects. Sequence variations may include without limitation, amino acid substitutions, extensions, deletions, truncations, interpolations, and combinations thereof. Such variations fall within the scope of the invention provided the protein containing them is immunogenic and antibodies against such polypeptide cross-react with naturally occurring KLK15 Related Protein to a sufficient extent to provide protective immunity and/or anti-tumorigenic activity when administered as a vaccine.

The proteins, peptides etc, can be incorporated into vaccines capable of inducing an immune response using methods known in the art. Techniques for enhancing the antigenicity of the proteins, peptides, etc. are known in the art and include incorporation into a multimeric structure, binding to a highly immunogenic protein carrier, for example, keyhole limpet hemocyanin (KLH), or diptheria toxoid, and administration in combination with adjuvants or any other enhancer of immune response.

Vaccines may be combined with physiologically acceptable media, including immunologically acceptable diluents and carriers as well as commonly employed adjuvants such as Freund's Complete Adjuvant, saponin, alum, and the like.

It will be further appreciated that anti-idiotype antibodies to antibodies to KLK15 Related Proteins described herein are also useful as vaccines and can be similarly formulated.

The administration of a vaccine in accordance with the invention, is generally applicable to the prevention or treatment of cancers including thyroid, prostate, colon, kidney, and testicular cancer.

The administration to a patient of a vaccine in accordance with the invention for the prevention and/or treatment of cancer can take place before or after a surgical procedure to remove the cancer, before or after a chemotherapeutic procedure for the treatment of cancer, and before or after radiation therapy for the treatment of cancer and any combination thereof. The cancer immunotherapy in accordance with the invention would be a preferred treatment for the prevention and /or treatment of cancer, since the side effects involved are substantially minimal compared with the other available treatments e.g. surgery, chemotherapy, radiation therapy. The vaccines have the potential or capability to prevent cancer in subjects without cancer but who are at risk of developing cancer.

The activity of the proteins, substances, compounds, antibodies, nucleic acid molecules, agents, and compositions of the invention may be confirmed in animal experimental model systems. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred.

4.4 Other Applications

The nucleic acid molecules disclosed herein may also be used in molecular biology techniques that have not yet been developed, provided the new techniques rely on properties of nucleotide sequences that are currently known, including but not limited to such properties as the triplet genetic code and specific base pair interactions.

The invention also provides methods for studying the function of a polypeptide of the invention. Cells, tissues, and non-human animals lacking in expression or partially lacking in expression of a nucleic acid molecule or gene of the invention may be developed using recombinant expression vectors of the invention having specific deletion or insertion mutations in the gene. A recombinant expression vector may be used to inactivate or alter the endogenous gene by homologous recombination, and thereby create a deficient cell, tissue, or animal.

Null alleles may be generated in cells, such as embryonic stem cells by deletion mutation. A recombinant gene may also be engineered to contain an insertion mutation that inactivates the gene. Such a construct may then be introduced into a cell, such as an embryonic stem cell, by a technique such as transfection, electroporation, injection etc. Cells lacking an intact gene may then be identified, for example by Southern blotting, Northern Blotting, or by assaying for expression of the encoded polypeptide using the methods described herein. Such cells may then be fused to embryonic stem cells to generate transgenic non-human animals deficient in a polypeptide of the invention. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on gene expression.

The invention thus provides a transgenic non-human mammal all of whose germ cells and somatic cells contain a recombinant expression vector that inactivates or alters a gene encoding a KLK15 Related Protein. In an embodiment the invention provides a transgenic non-human mammal all of whose germ cells and somatic cells contain a recombinant expression vector that inactivates or alters a gene encoding a KLK15 Related Protein resulting in a KLK15 Related Protein associated pathology. Further, the invention provides a transgenic non-human mammal which does not express or has altered (e.g. reduced) expression of a KLK15 Related Protein of the invention. In an embodiment, the invention provides a transgenic non-human mammal which does not express or has reduced expression of a KLK15 Related Protein of the invention resulting in a KLK15 Related Protein associated pathology. A KLK15 Related Protein pathology refers to a phenotype observed for a KLK15 Related Protein homozygous or heterozygous mutant.

A transgenic non-human animal includes but is not limited to mouse, rat, rabbit, sheep, hamster, dog, cat, goat, and monkey, preferably mouse.

The invention also provides a transgenic non-human animal assay system which provides a model system for testing for an agent that reduces or inhibits a pathology associated with a KLK15 Related Protein, preferably a KLK15 Related Protein associated pathology, comprising:

(a) administering the agent to a transgenic non-human animal of the invention; and
(b) determining whether said agent reduces or inhibits the pathology (e.g. KLK15 Related Protein associated pathology) in the transgenic non-human animal relative to a transgenic non-human animal of step (a) which has not been administered the agent.

The agent may be useful in the treatment and prophylaxis of conditions such as cancer as discussed herein. The agents may also be incorporated in a pharmaceutical composition as described herein.

The following non-limiting example is illustrative of the present invention:

EXAMPLE

Materials and Methods

Identification of the New Gene

A contiguous map for the human kallikrein gene locus extending from the KLK1 gene (centromere) to the KLK14 gene (telomere) (7,8,11,12,27) was constructed. Overlapping bacterial artificial chromosome (BAC) clones spanning this area were identified by screening of a human BAC library using different radiolabeled gene-specific probes. An area of ~300 kb of genomic sequence was established using different techniques, as previously described (11,27). By performing an EcoR1 restriction analysis, the kallikrein locus was oriented along the EcoR1 restriction map of chromosome 19q13 available from the Lawrence Livermore National Laboratory (LLNL). A BAC clone that extends more centromerically (BC 781134) was then identified. Contigs of linear genomic sequences from this clone are available from the LLNL. Initially, these contig sequences were used to predict the presence of novel genes, using bioinformatic approaches, as previously described (8,12), and a putative new serine protease was identified. The sequence of the putative gene was then verified by different approaches including sequencing, EST database search, PCR screening of tissues, as described below.

Expressed Sequence Tag (EST) Searching

The predicted exons of the putative new gene were subjected to homology search using the BLASTN algorithm (28) on the National Center for Biotechnology Information web server against the human EST database (dbEST). Clones with >95% homology were obtained from the I.M.A.G.E. consortium (29) through Research Genetics Inc, Huntsville, Ala. The clones were propagated, purified as described elsewhere (30) and sequenced from both directions with an automated sequencer, using insert-flanking vector primers.

Prostate Cancer Cell Line and Hormonal Stimulation Experiments

The LNCaP prostate cancer cell line was purchased from the American Type Culture Collection (ATCC), Rockville, Md. Cells were cultured in RPMI media (Gibco BRL, Gaithersburg, Md.) supplemented with glutamine (200 mmol/L), bovine insulin (10 mg/L), fetal bovine serum (10%), antibiotics and antimycotics, in plastic flasks, to near confluency. The cells were then aliquoted into 24-well tissue culture plates and cultured to 50% confluency. 24 hours before the experiments, the culture media were changed into phenol red-free media containing 10% charcoal-stripped fetal bovine serum. For stimulation experiments, various steroid hormones dissolved in 100% ethanol were added into the culture media at a final concentration of $10^{-8}$ M. Cells stimulated with 100% ethanol were included as controls. The cells were cultured for 24 hours, then harvested for mRNA extraction.

Reverse Transcriptase Polymerase Chain Reaction (RT-PCR) for the KLK15 Gene

Total RNA was extracted from the LNCaP cell line or from prostate tissues using Trizol reagent (Gibco BRL) following the manufacturer's instructions. RNA concentration was determined spectrophotometrically. 2 μg of total RNA was reverse-transcribed into first strand cDNA using the Superscript™ preamplification system (Gibco BRL). The final volume was 20 μl. Based on the combined information obtained from the predicted genomic structure of the new gene and the EST sequences (see below), two gene-specific primers were designed (KLK15-F1—SEQ ID NO. 47 and KLK15-R1—SEQ ID NO. 48) (Table 1) and PCR was carried out in a reaction mixture containing 1 μl of cDNA, 10 mM Tris-HCl (pH 8.3), 50 mM KCl, 1.5 mM $MgCl_2$, 200 μM dNTPs (deoxynucleoside triphosphates), 150 ng of primers and 2.5 units of HotStar™ DNA polymerase (Qiagen Inc., Valencia, Calif.) on a Perkin-Elmer 9600 thermal cycler. The cycling conditions were 95° C. for 15 minutes to activate the Taq DNA polymerase, followed by 35 cycles of 94° C. for 30 s, 64° C. for 30 s, 72° C. for 1 min and a final extension step at 72° C. PCR products were electrophoresed on 2% agarose gels and visualized by ethidium bromide staining. All primers for RT-PCR spanned at least 2 exons to avoid contamination by genomic DNA. To verify the identity of the PCR products, they were cloned into the pCR 2.1-TOPO vector (Invitrogen, Carlsbad, Calif., USA) according to the manufacturer's instructions. The inserts were sequenced from both directions using vector-specific primers, with an automated DNA sequencer.

Tissue Expression

Total RNA isolated from 26 different human tissues was purchased from Clontech, Palo Alto, Calif. cDNA was prepared as described above for the tissue culture experiments and used for PCR reactions. Tissue cDNAs were amplified at various dilutions using two gene-specific primers (KLK15-F2—SEQ ID NO. 49 and KLK15-R1—SEQ ID NO. 48) (Table 1). Due to the high degree of homology between kallikreins, and to exclude non-specific amplification, PCR products were cloned and sequenced.

Prostate Cancer Tissues

Prostate tissue samples were obtained from 29 patients who had undergone radical retropubic prostatectomy for prostatic adenocarcinoma at the Charite University Hospital, Berlin, Germany. The patients did not receive any hormonal therapy before surgery. The use of these tissues for research purposes was approved by the Ethics Committee of the Charite Hospital. Fresh prostate tissue samples were obtained from the cancerous and non-cancerous parts of the same prostates that had been removed. Small pieces of tissue were dissected immediately after removal of the prostate and stored in liquid nitrogen until analysis. Histological analysis from all the tissue pieces was performed as previously described (31), to ensure that the tissue was either malignant or benign. The tissues were pulverized with a hammer under liquid nitrogen and RNA was extracted as described above, using Trizol reagent.

Statistical Analysis

Statistical analysis was performed with SAS software (SAS Institute, Cary, N.C.). The analysis of differences between KLK15 expression in non-cancerous versus cancerous tissues from the same patient was performed with the non-parametric McNemar test. The binomial distribution was used to compute the significance level. Prostate tumor KLK15 mRNA levels were qualitatively classified into two categories (KLK15—low and KLK15—high groups) and associations between KLK15 status and other variables were analyzed using the Fisher's exact test.

Structure Analysis

Multiple alignment was performed using the "Clustal X" software package and the multiple alignment program available from the Baylor College of Medicine, Houston, Tex., USA. Phylogenetic studies were performed using the "Phylip" software package. Distance matrix analysis was performed using the "Neighbor-Joining/UPGMA" program and parsimony analysis was done using the "Protpars" program. Hydrophobicity study was performed using the Baylor College of Medicine search launcher. Signal peptide was predicted using the "SignalP" server. Protein structure analysis was performed by "SAPS" (structural analysis of protein sequence) program.

Results

Cloning of the KLK15 Gene

A contiguous map for the human kallikrein gene locus extending from the KLK1 gene (centromere) to the KLK14 gene (telomere) was previously established (7,8,11,12,27). In order to investigate the presence of other kallikrein-like genes centromeric to KLK1, a BAC clone (BC 781134) was obtained as described in materials and methods. According to the published genomic sequence of prostate specific antigen (PSA), and human renal kallikrein (KLK1) genes, gene-specific primers were designed for each of these genes (Table 1, SEQ ID NOs. 47-50) and polymerase chain reaction (PCR)-based amplification protocols were developed which allowed generation of specific PCR products with genomic DNA as a template. PCR screening of the BAC clone by these gene-specific primers indicated that this clone is positive for KLK1 but negative for PSA, thus, confirming its location to be centromeric to PSA.

A putative new serine protease was predicted from the sequence of this clone by computer programs as previously described (12). This clone was digested, blotted on a membrane and hybridized with gene-specific primers for the putative KLK15 gene (according to the predicted sequence), and positive fragments were subcloned and sequenced to verify the structure of the putative gene. This putative gene sequence was then blasted against the human EST database and two EST clones were identified (GenBank accession #AW274270 and #AW205420). These two clones were 99% identical to the last exon and the 3' untranslated region of the gene and the second EST ends with a stretch of 17 adenine (A) nucleotides that were not found in the genomic sequence, thus verifying the 3' end of the gene and the position of the poly A tail.

To identify the full mRNA structure of the gene and to determine the exon/intron boundaries, PCR reactions were performed using primers located in different computer-predicted exons, using a panel of 26 human tissue cDNAs as templates. PCR products were sequenced. Two of these primers (KLK15-F1—SEQ ID NO. 47, and KLK15-R1—SEQ ID NO. 48)) (Table 1) were able to amplify the full coding region of the gene from different tissues. Comparing the mRNA with the genomic structure indicated the presence of a gene formed of five coding exons with 4 intervening introns. Translation of the mRNA sequence in all possible reading frames revealed the presence of only one frame that gives an uninterrupted polypeptide chain, that also contains the highly conserved structural motifs of the kallikreins, as discussed below.

Structural Characterization of the KLK15 Gene

As shown in FIG. 1, the KLK15 gene is formed of 5 coding exons and 4 intervening introns, although, as with other kallikrein genes, the presence of further upstream untranslated exon(s) could not be ruled out (17,32,33). All of the exon/intron splice sites conform to the consensus sequence for eukaryotic splice sites (34). The gene further follows strictly the common structural features of other members of the human kallikrein multigene family, as described below. The predicted protein-coding region of the gene is formed of 771 bp, encoding a deduced 256 amino acid polypeptide with a predicted molecular weight of 28.1 kDa. The potential translation initiation codon matches the consensus Kozak sequence (35), moreover, there is a purine at position (−3) which occurs in 97% of vertebrate mRNAs (36). It should also be noted, that like most other kallikrein-like genes, KLK15 does not have the consensus G nucleotide at position (+4).

Figure 2:
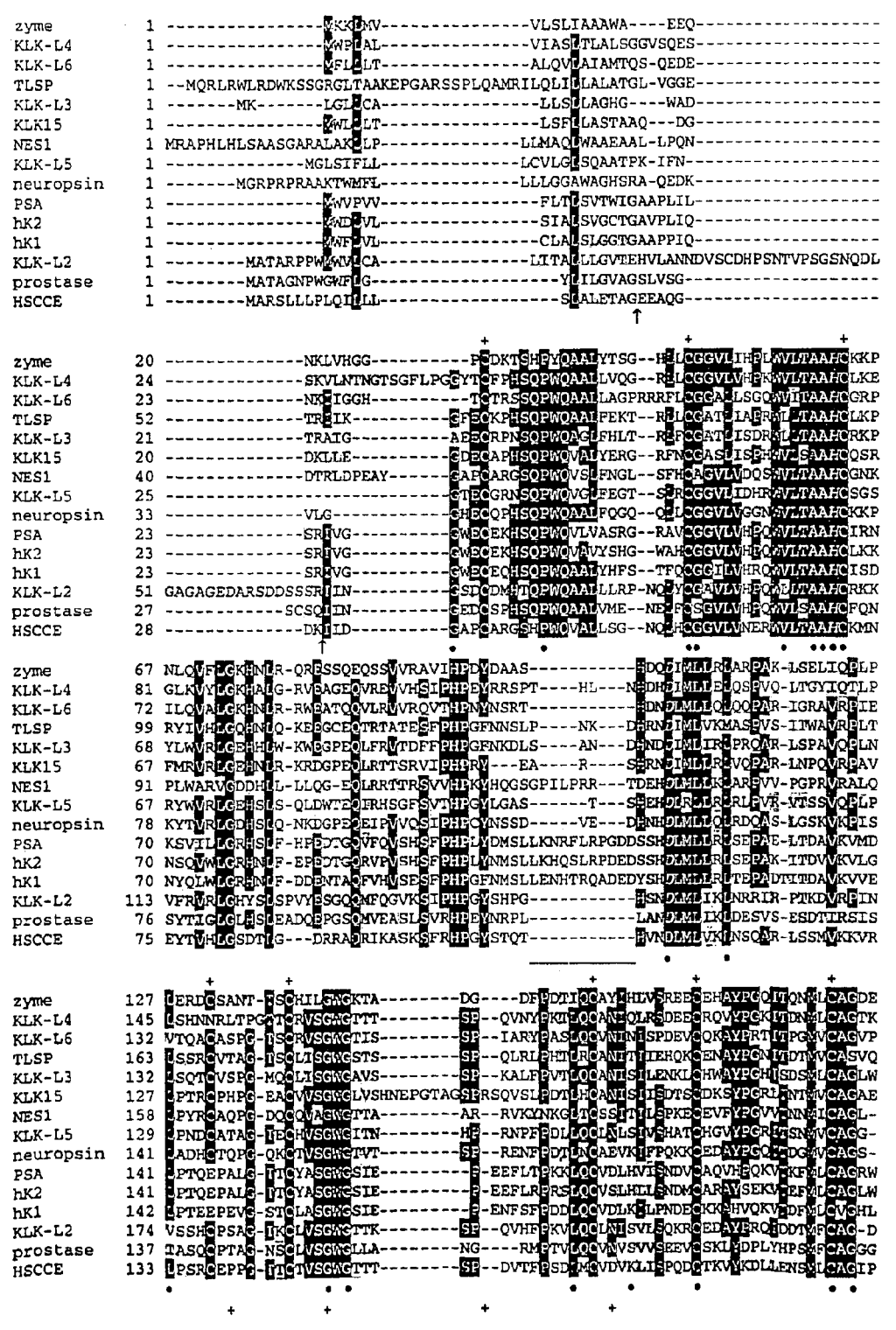

Nucleotides 7764-7769 (ATTAAA) (SEQ ID NO. 40) closely resemble a consensus polyadenylation signal (37) and are followed, after 17 nucleotides, by the poly A tail. No other potential polyadenylation signals were discernable in the 3' untranslated region, suggesting that the above sequence is the actual polyadenylation signal. Although AATAAA (SEQ ID NO. 40) is highly conserved, natural variants do occur, and the ATTAAA (SEQ ID NO. 40) sequence is reported to occur as a natural polyadenylation variant in 12% of vertebrate mRNA sequences (38). The presence of glutamic acid (E) at position 203 suggests that KLK15 will likely possess an unique substrate specificity. PSA has a serine (S) residue in the corresponding position and has chymotryptic-like activity. Many other kallikreins usually have aspartate (D) in this position indicating a trypsin-like activity (FIG. 2) (6).

Although the KLK15 protein sequence is unique, comparative analysis revealed that it has a considerable degree of homology with other members of the kallikrein multigene family. KLK15 shows 51% protein identity and 66% similarity with the trypsin like serine protease (TLSP) and 49%, 48% identity with the neuropsin and KLK-L3 proteins, respectively. Hydrophobicity analysis revealed that the amino-terminal region is quite hydrophobic (FIG. 3), consistent with the possibility that this region may harbor a signal sequence, analogous to other serine proteases. Computer analysis of the KLK15 protein sequence predicted a cleavage site between amino acids 16 and 17 (TAA-QD). Sequence alignment (FIG. 2) also revealed another potential cleavage site ($Lys^{21}$), at a site homologous to the activation site of other serine proteases [lysine (K) or arginine (R) is present in most cases] (39). Several evenly distributed hydrophobic regions throughout the KLK15 polypeptide are consistent with a globular protein, similar to other kallikreins and serine proteases. Thus, as is the case with other kallikreins, KLK15 is presumably translated as an inactive 256 amino acid preproenzyme precursor. Prepro-KLK15 has 21 additional residues which constitute the pre-region (the signal peptide formed of 16 residues), and the propeptide (5 residues).

The dotted region in FIG. 2 indicates an 11-amino acid loop characteristic of the classical kallikreins (PSA, KLK1, and KLK2) but not found in KLK15 or other members of the kallikrein multi-gene family (10,11,13,14). However, KLK15 has a unique 8 amino acid loop (HNEPGTAG) (SEQ ID NO. 10) at positions 148-155, not found in any other kallikrein (FIG. 2). Twenty nine "invariant" amino acids surrounding the active site of serine proteases have been described (40). Of these, twenty eight are conserved in KLK15. One of the unconserved amino acids ($Ser^{173}$ instead of Pro) is also found in prostase, KLK-L2 and KLK-L5 proteins, and represents a conserved evolutionary change to a protein of the same group, according to protein evolution studies (41). Twelve cysteine residues are present in the putative mature KLK15 protein; ten of them are conserved in all kallikreins, and would be expected to form disulphide bridges. The other two (C131 and C243) are not found in PSA, KLK1, KLK2 or KLK-L4, however, they are found in similar positions in all other kallikrein genes and are expected to form an additional disulphide bond.

Figure 4:
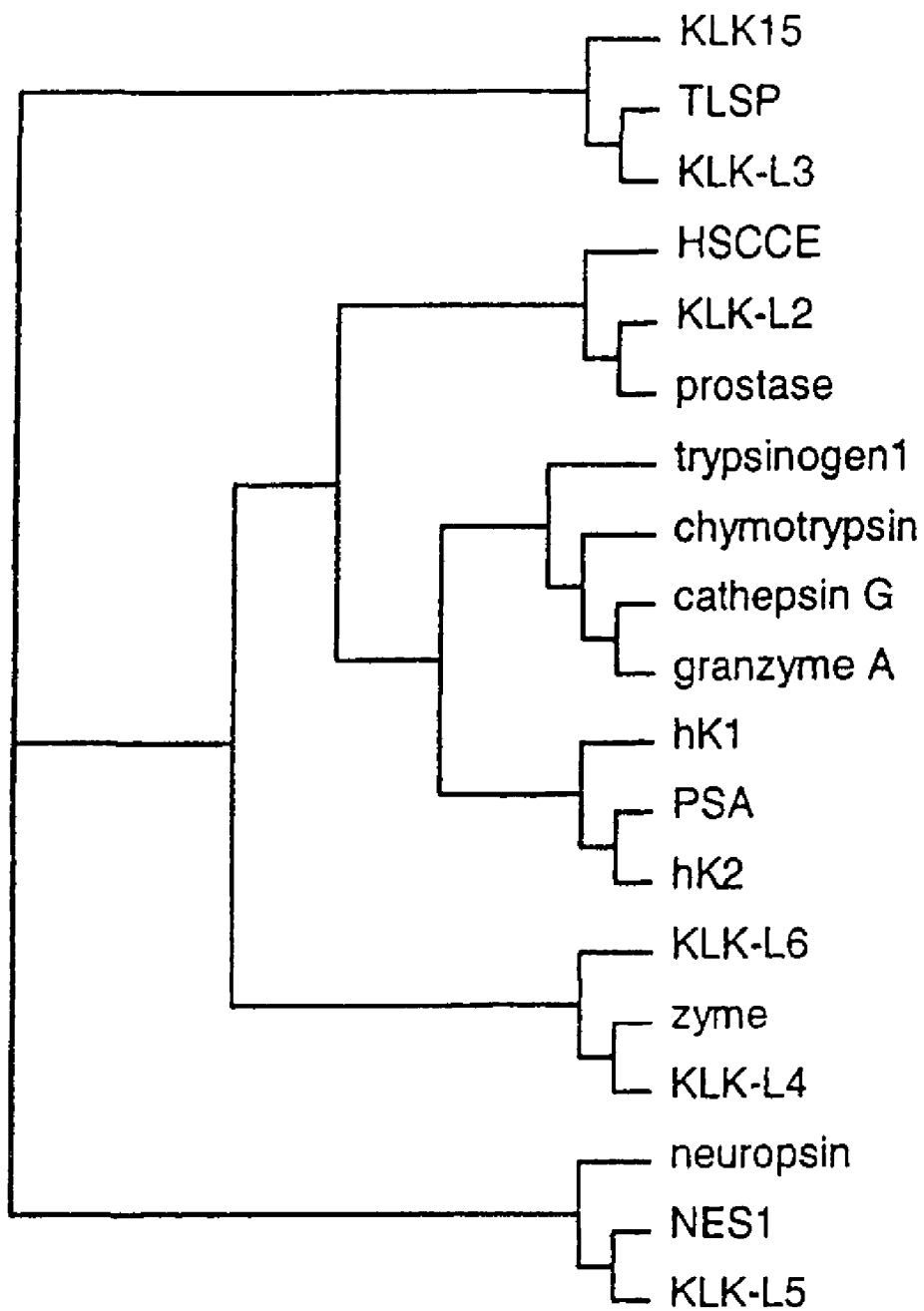
FIG. 4 is a dendrogram of the predicted phylogenetic tree for 15 kallikreins and a few other serine proteases. The neighbor-joining method was used to align KLK15 with other serine proteases and members of the kallikrein gene family. The tree grouped the classical kallikreins (hK1, hK2, and PSA) together and aligned KLK15 in one group with TLSP and KLK-L3 genes. Other serine proteases were aligned in different groups, as shown. KLK represents kallikrein; KLK-L represents kallikrein-like; TLSP represents trypsin-like serine protease; NES1 represents normal epithelial cell-specific gene; PSA represents prostate specific antigen; hK1 and hK2 represents human glandular kallikrein 1 and 2, respectively; and HSCCE represents human stratum corneum chymotryptic enzyme.

To predict the phylogenetic relatedness of the KLK15 protein with other serine proteases, the amino acid sequences were aligned together using the Unweighted Pair Group Method with Arithmetic mean (UPGMA) and the Neighbor-Joining distance matrix methods, and the "Protpars" parsimony method. All phylogenetic trees obtained agreed that other serine proteases (non-kallikreins) can be grouped together as a separate group, indicating that kallikreins represent a separate step in the evolution of serine proteases. KLK15 was grouped with the KLK-L3 and TLSP (FIG. 4) and the classical kallikreins (hK1, hK2, and PSA) are grouped together in all trees, suggesting that the separation between classical kallikreins and the kallikrein-like genes occurred early during evolution, consistent with suggestions of previous studies (13).

Splice Variants of the KLK15 Gene

Figure 5:
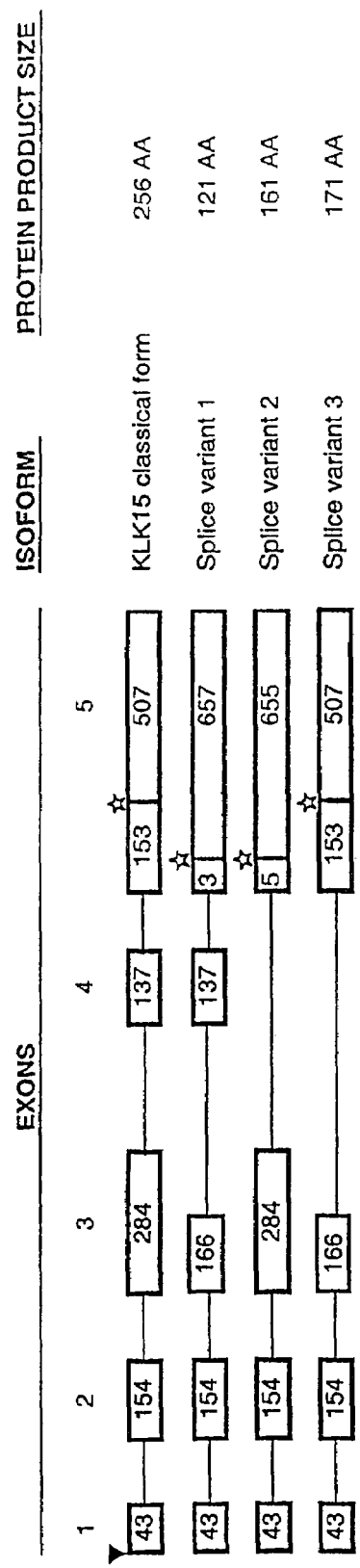
FIG. 5 is a schematic presentation of the different splice variants of the KLK15 gene. Exons are shown by boxes and introns by the connecting lines. Numbers inside boxes represent the exon lengths in base pairs. The arrowhead points to the common start codon and stars to the stop codon positions. The length of the predicted polypeptide product is indicated beside each variant in amino acids (AA). The alternative splicing and/or exon skips create a frame shift, which leads to a premature termination.
Figure 6:
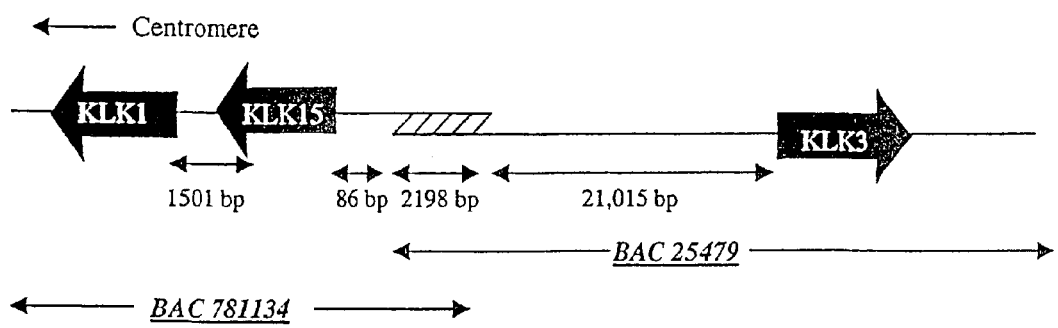
FIG. 6 shows the relative locations of KLK1, KLK15, and KLK3 genes on chromosome 19q13.3-q13.4. The two overlapping BAC clones are identified, and the overlap region is hatched. Genes are represented by horizontal arrows denoting the direction of the coding sequence. Distances between genes are mentioned in base pairs. Figure is not drawn to scale.
Figure 7:
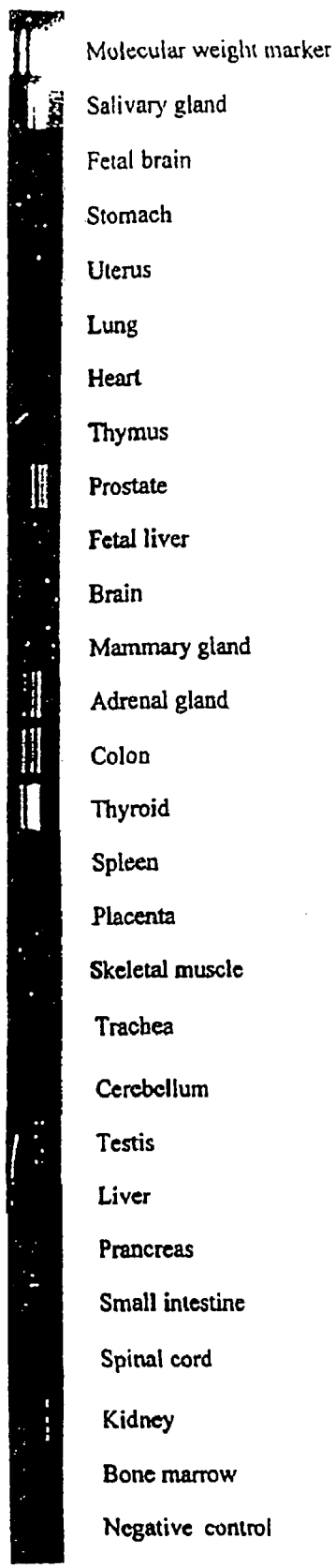
FIG. 7 shows tissue expression of the KLK15 gene, as determined by RT-PCR. KLK15 is primarily expressed in the thyroid gland, and to a lower extent in the prostate, salivary and adrenal glands, colon, testis and kidney. M=Molecular weight marker. For explanation of the multiple PCR bands (alternatively spliced forms) see the Example. PCR was performed with primers KLK15-F2 and KLK15-R1.

PCR screening for KLK15 transcripts using gene-specific primers (KLK15-F2—SEQ ID NO. 49 and KLK15-R2—SEQ ID NO. 50) (Table 1) revealed the presence of 3 bands in most of the tissue cDNAs examined (FIG. 6). These bands were gel purified, cloned and sequenced. The upper band represents the classical form of the gene, and the lower band is splice variant 3 (FIG. 7). The middle band represents two other splice variants. Restriction digestion of the PCR product of the middle band with Stu 1, followed by gel separation, purification, and sequencing revealed that it is composed of splice variants 1 and 2 which have approximately the same length (splice variant 1 has exon 4 (137 bp) but is missing 118 bp from exon 3, while splice variant 2 has an additional 118 bp of exon 3 but missing exon 4. All splice variants are expected to encode for truncated protein products (FIG. 5).

Chromosomal Localization of the KLK15 Gene

Restriction analysis study of a number of overlapping BAC clones spanning the human kallikrein locus followed by comparison with the EcoR1 restriction map of the area (available from the LLNL web site) enabled identification of a BAC clone (BC 25479) that is telomerically adjacent to BC 781134 (which harbors the KLK15 gene). Blasting the sequences of the two clones showed that the ends of these clones are overlapping. By identifying the position of the KLK1, KLK3 and KLK15 genes along these clones, the relative location and the direction of transcription of these three genes were precisely defined. KLK1 is the most centromeric and its direction of transcription is from telomere to centromere, followed by KLK15, which is more telomeric and transcribes in the same direction. The distance between the two genes is 1501 bp in length. The KLK3 gene is more telomeric, located at a distance of 23,335 from the KLK15, and is transcribed in the opposite direction (FIG. 6). These results are consistent with previous reports where the distance between KLK3 and KLK1 was roughly estimated to be ~31 Kb (6,27).

Tissue Expression and Hormonal Regulation of the KLK15 Gene

Figure 8:
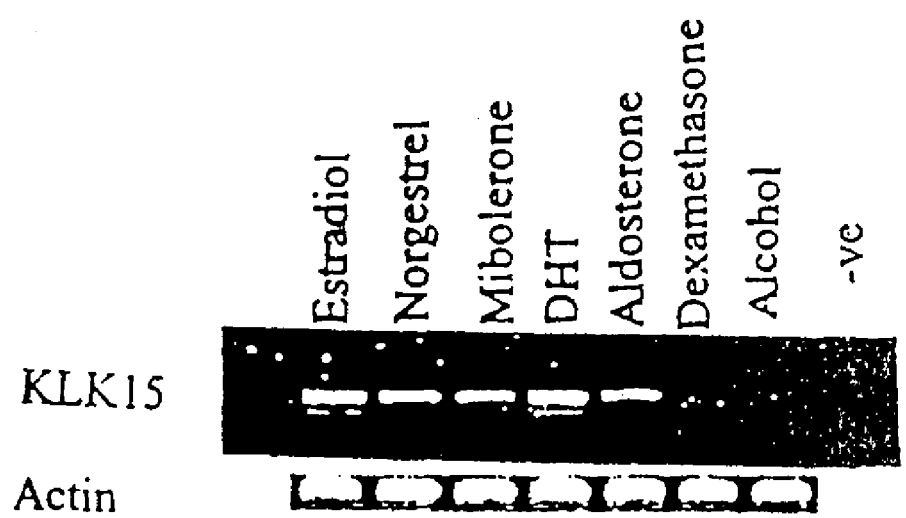
FIG. 8 shows hormonal regulation of the KLK15 gene in the LNCaP prostate cancer cell line. DHT=dihydrotestosterone. Steroids were added at $10^{-8}$ M final concentrations. (−ve)=negative control. Actin was used as a control gene.
Figure 9:
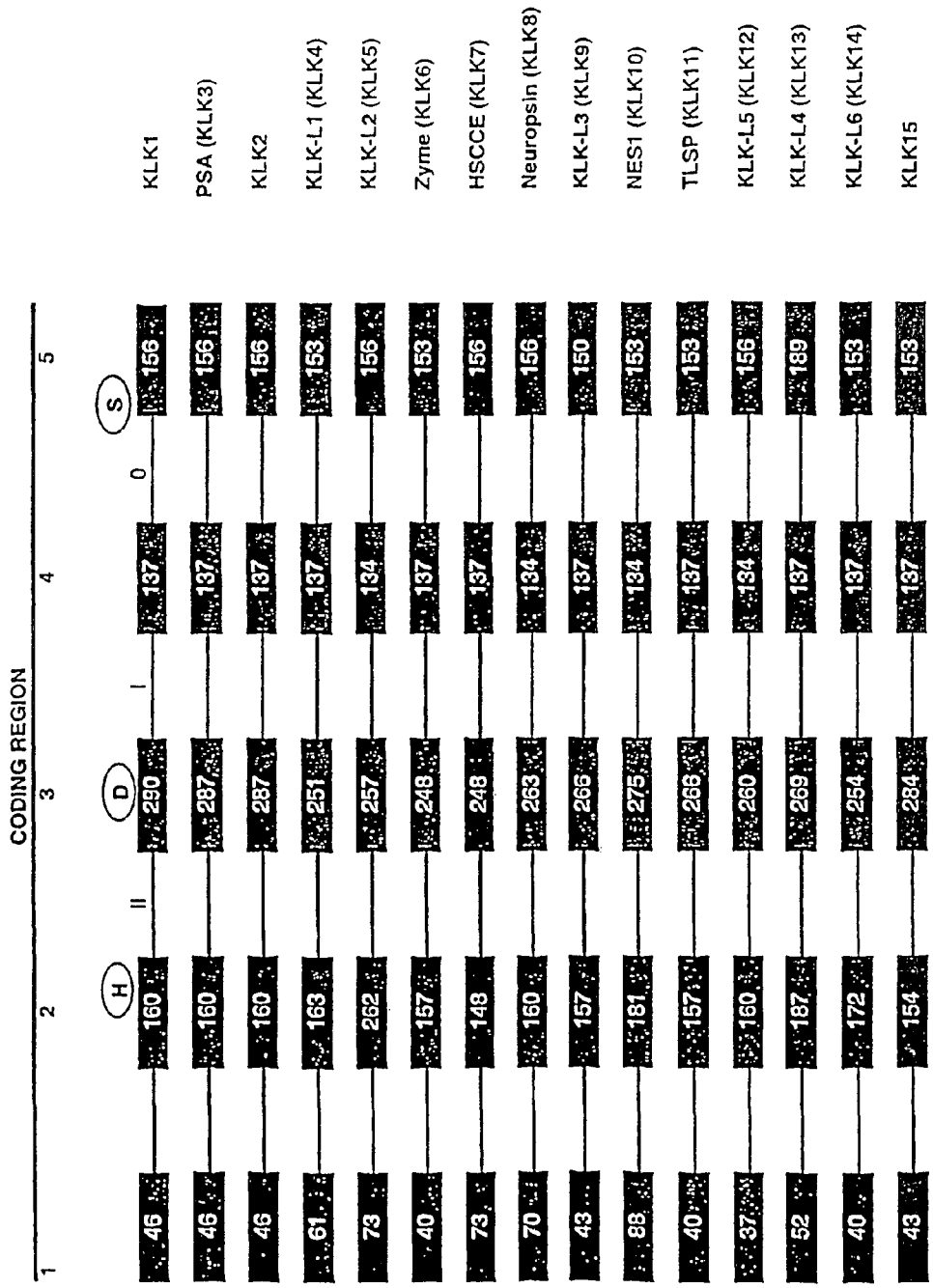
FIG. 9 is a schematic diagram showing the comparison of the coding regions of the 15 kallikrein genes. Exons are shown by solid bars and introns by the connecting lines. Letters above boxes indicate relative positions of the catalytic triad that was found to be conserved in all genes; H denotes histidine, D aspartic acid and S serine. Roman numbers indicate intron phases. The intron phase refers to the location of the intron within the codon; I denotes that the intron occurs after the first nucleotide of the codon, II the intron occurs after the second nucleotide, 0 the intron occurs between codons. The intron phases are conserved in all genes. Numbers inside boxes indicate exon lengths in base pairs. Names inside brackets represent the official nomenclature approved by the human gene nomenclature committee. Untranslated 3' and 5' regions and 5' untranslated exons are not shown.

As shown in FIG. 7, the KLK15 gene is expressed at highest levels in the thyroid gland. Lower levels of expression are also seen in the prostate, salivary and adrenal glands, colon, testis and kidney. In order to verify the RT-PCR specificity, representative PCR products were cloned and sequenced. FIG. 8 shows that the KLK15 gene is up-regulated by steroid hormones in the human LNCaP prostate cancer cell line.

KLK15 Expression in Prostate Cancer

The expression of the KLK15 gene in normal and cancerous prostatic tissues was examined by RT-PCR. Actin was included as a control gene to ensure the quality and amount of the cDNA used. In order to examine the relative expression of the KLK15 gene in normal compared with malignant tissues, 29 pairs of prostatic tissues were examined. Each pair represented normal and cancerous tissue obtained from the same patient. The results are summarized in Table 2. Thirteen out of 29 patients had significantly higher KLK15 expression in the cancer tissue and only three had the expression of KLK15 higher in non-cancer than to cancer tissues. Analysis by the McNemar test indicated that the differences between normal and cancerous tissues are statistically significant (P=0.021). Because of the small number of cases, the binomial distribution was used to compute the significance level. The prostate cancer patients were further classified into two groups: (a) KLK15 expression-positive (N=21) and (b) KLK15 expression-negative (or very low) (N=8). When the association of KLK15 expression was compared with clinicopathological prognostic variables higher KLK15 expression was found to be more frequent in patients with late stage disease and tumours of higher grade (Table 3).

Discussion

Kallikreins are a subgroup of serine proteases. The term 'kallikrein' is usually utilized to describe an enzyme that acts upon a precursor molecule (kininogen) for release of a bioactive peptide (kinin)(3,42). However, the generic term 'tissue kallikrein' is not restricted to the functional definition of the enzyme. This term is now used to describe a group of enzymes with highly conserved gene and protein structure which also co-localize in the same chromosomal locus. Among the three classical human kallikrein genes, only KLK1 encodes for a protein with potent kininogenase activity. The enzymes encoded by KLK2 and KLK3 genes have very weak kininogenase activity. The already cloned 14 members of the human kallikrein gene family have a number of similarities (7,11) as show below:

All genes localize to the same chromosomal region (19q13.3-q13.4)

All genes encode for putative serine proteases with a conserved catalytic triad in the appropriate positions, i.e., histidine near the end of the second coding exon, aspartic acid in the middle of the third exon, and serine at the beginning of the fifth (last) exon.

All genes have five coding exons (some members contain one or more 5/-untranslated exons).

Coding exon sizes are similar or identical.

Intron phases are fully conserved.

All genes have significant sequence homologies at the DNA and amino acid levels (30-80%).

Many of these genes are regulated by steroid hormones.

FIGS. 2 and 8 show that the newly identified KLK15 gene shares all the above similarities and is thus a new member of the human kallikrein multigene family. This gene was named KLK15.

Many kallikrein genes are related to the pathogenesis of human diseases, depending on the tissue of their primary expression. The KLK1 gene is involved in many disease processes, including inflammation (3), hypertension (44), renal nephritis and diabetic renal disease (45,46), The connections of HSCCE (KLK7) with skin diseases, including pathological keratinization and psoriasis, have already been reported (47,48). Little et al. suggested that zyme (KLK6) may be amyloidogenic and may play a role in the development of Alzheimer's disease (14). There are other reports describing connection of neuropsin (KLK8) expression with diseases of the central nervous system, including epilepsy (49,50). Being primarily expressed in the thyroid, KLK15 may play an important role in the normal physiology and pathophysiology of this gland. Among all other discovered kallikreins, many are expressed in the thyroid but none at highest levels in this tissue (7,11)

The KLK15 gene is up-regulated, at the mRNA level, in a subset of prostate cancers. The distributions of KLK15 qualitative expression status (high or low) between subgroups of patients differing by disease stage, tumor grade and Gleason score indicated that high KLK15 expression was found more frequently in Grade 3 tumors as well as in stage III and Gleason score >6 patients. These findings indicate that overexpression of KLK15 is associated with more aggressive forms of the disease and may be an indicator of poor prognosis (Table 3).

There is now growing evidence that many kallikreins and kallikrein-like genes are related to malignancy. PSA is the best marker for prostate cancer so far (20). Recent reports suggest that hK2 (encoded by the KLK2 gene) could be another useful diagnostic marker for prostate cancer (21,51). NES1 (KLK10) appears to be a novel tumor suppressor gene (23). The zyme (KLK6) gene was shown to be differentially expressed in primary breast and ovarian tumors (24), and the human stratum corneum chymotryptic enzyme (HSCCE, KLK7) has been shown to be expressed at abnormally high levels in ovarian cancer (25). Another recently identified kallikrein-like gene, tentatively named the tumor-associated differentially expressed gene-14 (TADG-14)/neuropsin) (KLK8) was found to be overexpressed in about 60% of ovarian cancer tissues (26). Pprostase/KLK-L1/(KLK4), another newly discovered kallikrein-like gene, is speculated to be linked to prostate cancer (13). Two newly discovered kallikreins, KLK-L4 (KLK13) and KLK-L5 (KLK12), were also found to be downregulated in breast cancer (10). Thus, extensive new literature suggests multiple connections of various kallikrein genes to many forms of human cancer.

The existence of multiple alternatively spliced mRNA forms is frequent among the kallikreins. Distinct RNA species are transcribed from the PSA gene, in addition to the major 1.6 kb transcript (19,52,53). Also, Reigman et al reported the identification of two alternatively spliced forms of the human glandular kallikrein 2 (KLK2) gene (54). A novel transcript of the tissue kallikrein gene (KLK1) was also isolated from the colon (55). Neuropsin, a recently identified kallikrein-like gene, was found to have two alternatively spliced forms, in addition to the major form (26,56). KLK-L4 was also found to have different alternatively spliced forms (10). Because the splice variants of KLK15 have an identical 5' sequence required for translation, secretion and activation, it is possible to assume that they encode for a secreted protein (53).

In conclusion, a new member of the human kallikrein gene family, KLK15, has been characterized which maps to the human kallikrein locus (chromosome 19q13.3-q13.4). This gene has three related splice forms in addition to the classical form. KLK15 is expressed in a variety of tissues but predominantly in the thyroid, it appears to be up-regulated in more aggressive forms of prostate cancer and its expression is influenced by steroid hormones. Since a few other kallikreins are already used as valuable tumor markers, KLK15 may also find similar clinical applications.

Having illustrated and described the principles of the invention in a preferred embodiment, it should be appreciated to those skilled in the art that the invention can be modified in arrangement and detail without departure from such principles. All modifications coming within the scope of the following claims are claimed.

All publications, patents and patent applications referred to herein are incorporated by reference in their entirety to the same extent as if each individual publication, patent or patent application was specifically and individually indicated to be incorporated by reference in its entirety.

TABLE 1

Primers used for genomic PCR amplification.

| Gene | Primer name and sequence | GenBank accession # | SEQ ID NO: |
|------|--------------------------|---------------------|------------|
| KLK1 | KLK1-A: ATC CCT CCA TTC CCA TCT TT | L10038 | 41 |
|      | KLK1-B CAC ATA CAA TTC TCT GGT TC |  | 42 |
| KLK2 | KLK2-A: AGT GAC ACT GTC TCA GAA TT | M18157 | 43 |
|      | KLK2-B: CCC CAA TCT CAC GAG TGC AC |  | 44 |
| PSA  | E5-A: GTC GGC TCT GGA GAC ATT TC | M27274 | 45 |
|      | E5-B: AAC TGG GGA GGC TTG AGT C |  | 46 |

TABLE 1-continued

Primers used for genomic PCR amplification.

| Gene | Primer name and sequence | GenBank accession # | SEQ ID NO: |
|---|---|---|---|
| KLK15 | KLK15-F1<br>CTC CTT CCT GCT GGC ATC CA | AF242195 | 47 |
| | KLK15-R1<br>ATC ACA CGG GTG GTC ATG TG | | 48 |
| | KLK15-F2<br>CAA GTG GCT CTC TAC GAG CG | | 49 |
| | KLK15-R2<br>GAC ACC AGG CTT GGT GGT GT | | 50 |

* all primers are presented in 5'→3' direction.

TABLE 2

KLK15 expression in 29 pairs of cancerous and non-cancerous prostatic tissues.

| KLK15 Expression | Number of patients | P value * |
|---|---|---|
| Higher in cancer vs. normal | 13 | |
| Lower in cancer vs. normal | 3 | |
| High expression but approx. equal in both tissues | 8 | |
| Low (or no) expression but approx. equal in both tissues | 5 | 0.021 |

* P value was calculated by the McNemar test using the binomial distribution.

TABLE 3

Relationship between KLK15 expression and other clinicopathological variables in 29 patients with primary prostate cancer

| | | No. of patients (%) | | P value* |
|---|---|---|---|---|
| Variable | Patients | KLK15 negative | KLK15 positive | |
| Stage | | | | |
| I/II | 20 | 8 (40) | 12 (60) | 0.033 |
| III | 9 | 0 (0) | 9 (100) | |
| Grade | | | | |
| G1/2 | 23 | 8 (34.8) | 15 (65.2) | 0.15 |
| G3 | 6 | 0 (0) | 6 (100) | |
| Gleason score | | | | |
| ≦6 | 22 | 7 (31.8) | 15 (62.2) | 0.14 |
| >6 | 6 | 0 (0) | 6 (100) | |
| Unknown | 1 | | | |

*Fisher's Exact Test.

FULL CITATIONS FOR REFERENCES REFERRED TO IN THE SPECIFICATION

1. Kraut, H., K., F. E., and Werle, E. (1930) *Physiol. Chem.* 189, 97-106
2. Werle, E. (1934) *Biochem. Z* 269, 415-434
3. Clements, J. (1997) in *The Kinin System* (Farmer, S., ed), pp. 71-97, Academic Press, New York
4. Evans, B. A., Drinkwater, C. C., and Richards, R. I. (1987) *J. Biol. Chem.* 262, 8027-34
5. Ashley, P. L., and MacDonald, R. J. (1985) *Biochemistry* 24, 4520-7
6. Riegman, P. H., Vlietstra, R. J., Suurmeijer, L., Cleutjens, C. B., and Trapman, J. (1992) *Genomics* 14, 6-11
7. Diamandis, E. P., Yousef, G. M., Luo, L. Y., Magklara, A., and Obiezu, C. V. (2000) *Trends Endocrinol. Metab.* 11, 54-60
8. Yousef, G. M., Obiezu, C. V., Luo, L. Y., Black, M. H., and Diamandis, E. P. (1999) *Cancer Res.* 59, 4252-6
9. Yousef, G. M., and Diamandis, E. P. (1999) *J. Biol. Chem.* 274, 37511-6
10. Yousef, G. M., Chang, A., and Diamandis, E. P. (2000) *J Biol Chem* 275, 11891-8.
11. Yousef, G. M., and Diamandis, E. P. (2000) *Genomics* 65, 184-194
12. Yousef, G. M., Luo, L. Y., and Diamandis, E. P. (1999) *Anticancer Res.* 19, 2843-52
13. Nelson, P. S., Gan, L., Ferguson, C., Moss, P., Gelinas, R., Hood, L., and Wang, K. (1999) *Proc. Natl. Acad Sci. U.S.A.* 96, 3114-9
14. Little, S. P., Dixon, E. P., Norris, F., Buckley, W., Becker, G. W., Johnson, M., Dobbins, J. R., Wyrick, T., Miller, J. R., MacKellar, W., Hepburn, D., Corvalan, J., McClure, D., Liu, X., Stephenson, D., Clemens, J., and Johnstone, E. M. (1997) *J. Biol. Chem.* 272, 25135-42
15. Liu, X. L., Wazer, D. E., Watanabe, K., and Band, V. (1996) *Cancer Res.* 56, 3371-9
16. Hansson, L., Stromqvist, M., Backman, A., Wallbrandt, P., Carlstein, A., and Egelrud, T. (1994) *J. Biol. Chem.* 269, 19420-6
17. Yoshida, S., Taniguchi, M., Hirata, A., and Shiosaka, S. (1998) *Gene* 213(1-2), 9-16
18. Stephenson, S. A., Verity, K., Ashworth, L. K., and Clements, J. A. (1999) *J. Biol. Chem.* 274, 23210-4
19. Riegman, P. H., Vlietstra, R. J., van der Korput, J. A., Romijn, J. C., and Trapman, J. (1989) *Biochem. Biophys. Res. Commun.* 159, 95-102
20. Diamandis, E. P. (1998) *Trends Endocrinol. Metab.* 9, 310-316
21. Stenman, U. H. (1999) *Clin. Chem.* 45, 753-4
22. Partin, A. W., Catalona, W. J., Finlay, J. A., Darte, C., Tindall, D. J., Young, C. Y., Klee, G. G., Chan, D. W., Rittenhouse, H. G., Wolfert, R. L., and Woodrum, D. L. (1999) *Urology* 54, 839-45
23. Goyal, J., Smith, K. M., Cowan, J. M., Wazer, D. E., Lee, S. W., and Band, V. (1998) *Cancer Res.* 58, 4782-6
24. Anisowicz, A., Sotiropoulou, G., Stenman, G., Mok, S. C., and Sager, R. (1996) *Mol. Med* 2, 624-36
25. Tanimoto, H., Underwood, L. J., Shigemasa, K., Yan Yan, M. S., Clarke, J., Parmley, T. H., and O'Brien, T. J. (1999) *Cancer* 86, 2074-82
26. Underwood, L. J., Tanimoto, H., Wang, Y., Shigemasa, K., Parmley, T. H., and O'Brien, T. J. (1999) *Cancer Res.* 59(17), 4435-9
27. Yousef, G. M., Chang, A., and Diamandis, E. P. (2000) submitted
28. Altschul, S. F., Madden, T. L., Schaffer, A. A., Zhang, J., Zhang, Z., Miller, W., and Lipman, D. J. (1997) *Nucleic Acids Res.* 25(17), 3389-402
29. Lennon, G., Auffray, C., Polymeropoulos, M., and Soares, M. B. (1996) *Genomics* 33, 151-2
30. Sambrook, J., Fritsch, E. F., and Maniatis, T. (1989) *Molecular Cloning: A Laboratory Manual,* Second Edition Ed., Cold Spring Harbor Laboratory, NY
31. Meyer, A., Jung, K., Lein, M., Rudolph, B., Schnorr, D., and Loening, S. A. (1997) *Int. J. Cancer* 74, 630-6
32. Luo, L., Herbrick, J. A., Scherer, S. W., Beatty, B., Squire, J., and Diamandis, E. P. (1998) *Biochem. Biophys. Res. Commun.* 247(3), 580-6
33. Yousef, G. M., Luo, L. Y., Scherer, S. W., Sotiropoulou, G., and Diamandis, E. P. (1999) *Genomics* 62(2), 251-9

34. Iida, Y. (1990) *J. Theor. Biol.* 145(4), 523-33
35. Kozak, M. (1991) *J. Cell Biol.* 115(4), 887-903
36. Kozak, M. (1987) *Nucleic Acids Res.* 15(20), 8125-48
37. Proudfoot, N. J., and Brownlee, G. G. (1976) *Nature* 263, 211-4
38. Sheets, M. D., Ogg, S. C., and Wickens, M. P. (1990) *Nucleic Acids Res.* 18(19), 5799-805
39. Keil, B. (1971) in *The enzymes* (P. D. Boyer, E., ed) Vol. 3, 3rd Ed., pp. 249-275, Academic Press, New York
40. Dayhoff, M. O. (1978) *Natl. Biomed Res. Found.* 5, 79-81
41. Miyata, T., Miyazawa, S., and Yasunaga, T. (1979) *J. Mol. Evol.* 12(3), 219-36
42. Bhoola, K. D., Figueroa, C. D., and Worthy, K. (1992) *Pharmacol. Rev.* 44(1), 1-80
43. Diamandis, E. P., Yousef, G., Clements, J. et al., (2000) *Clin. Chem.* In press
44. Margolius, H. S., Horwitz, D., Pisano, J. J., and Keiser, H. R. (1974) *Circ. Res.* 35(6), 820-5
45. Jaffa, A. A., Chai, K. X., Chao, J., Chao, L., and Mayfield, R. K. (1992) *Kidney Int.* 41(4), 789-95
46. Cumming, A. D., Walsh, T., Wojtacha, D., Fleming, S., Thomson, D., and Jenkins, D. A. (1994) *Clin. Sci.* 87(1), 5-11
47. Sondell, B., Dyberg, P., Annerroth, G. K., Ostman, P. O., and Egelrud, T. (1996) *Acta Derm. Venereol.* 76(3), 177-81
48. Ekholm, E., and Egelrud, T. (1999) *Arch. Dermatol. Res.* 291(4), 195-200
49. Momota, Y., Yoshida, S., Ito, J., Shibata, M., Kato, K., Sakurai, K., Matsumoto, K., and Shiosaka, S. (1998) *Eur. J. Neurosci.* 10(2), 760-4
50. Kishi, T., Kato, M., Shimizu, T., Kato, K., Matsumoto, K., Yoshida, S., Shiosaka, S., and Hakoshima, T. (1999) *J. Biol. Chem.* 274, 4220-4
51. Black, M. H., Magklara, A., Obiezu, C. V., Melegos, D. N., and Diamandis, E. P. (1999) *Clin. Chem.* 45(6 Pt 1), 790-9
52. Riegman, P. H., Klaassen, P., van der Korput, J. A., Romijn, J. C., and Trapman, J. (1988) *Biochem. Biophys. Res. Commun.* 155(1), 181-8
53. Heuze, N., Olayat, S., Gutman, N., Zani, M. L., and Courty, Y. (1999) *Cancer Res.* 59, 2820-4
54. Riegman, P. H., Vlietstra, R. J., van der Korput, H. A., Romijn, J. C., and Trapman, J. (1991) *Mol. Cell Endocrinol.* 76(1-3), 181-90
55. Chen, L. M., Murray, S. R., Chai, K. X., Chao, L., and Chao, J. (1994) *Braz. J. Med. Biol. Res.* 27(8), 1829-38
56. Mitsui, S., Tsuruoka, N., Yamashiro, K., Nakazato, H., and Yamaguchi, N. (1999) *Eur. J. Biochem.* 260(3), 627-34

We claim:

1. An isolated protein consisting of the amino acid sequence of SEQ ID NO:6.

2. An isolated and substantially pure protein having the amino acid sequence of SEQ ID NO:6 produced by the expression of a purified nucleic acid encoding the amino acid sequence of SEQ ID NO:6.

3. A pharmaceutical composition comprising the isolated protein of claim 1 and a pharmaceutically acceptable carrier, excipient or diluent.

4. An immunogenic composition for stimulating or enhancing production of antibodies directed against the isolated protein as claimed in claim 1 in a subject, the immunogenic composition comprising the isolated protein.

* * * * *

SEQUENCE LISTING

```
<160> NUMBER OF SEQ ID NOS: 50

<210> SEQ ID NO 1
<211> LENGTH: 8735
<212> TYPE: DNA
<213> ORGANISM: Homo sapiens

<400> SEQUENCE: 1
agaatgggtg ctgtgggatt caggggagac acctgttagg tgttggggcc tcccagaaga      60
ggtgggggca gagtgtcaga ggacaaagat gaatttggaa gatatgggga agaaggatatt    120 caattcaccc tcaaagcttc ctgaggcctc ccgtgggtcg ggccctgcag tactggagac     180
ccagagtgga gtcagaccag ctcctcgggg agctgccagt ctcgtagggg aggcagacac     240
cactgagggt caggggaggt cagagaaggc ctcaaggagg aagcggggct ggaagggaat     300
ggcgttggat atgcggtggg aggaatagcc taagcatgaa atggcaggag ggaaaatggc     360
agcactggct gcgtctagga caaggtcatg ggagacccag ggagaggggc tggaagggaa     420
gaagccactt ttgtccttga aagtgaggct ggagccaggc aactcatgcc tgtaatccca     480
gcactttggg aggctgaggc gggtggatca ctagaggtca ggagttcaag accagcctgg     540
ccaacatggt gaaactccgt ctctactaaa attacaaaaa ttagctgggc gtggtggcac     600
acacctgtaa tcccaattgc ttgggaggct gaggcaggag aatctcttga acccagaagg    660
cagaggttac agtgagcgga gatcacgcca ctccactcca acctgggcta cagagccaga    720
ctccgtctca aaaaaaaaa aaaaaagaa aaaaaagaa agaaagtgaa tttgaagagc       780
tggactttat cctggtggtg ccaaggatcc atggagggtg gtgagcaggg gaggggcaca    840
gccagctcca gatgtagaaa gacccttttgg ggtcatggct ggagggcaag ctggtggagg   900
ggactggact ggagggggac ccaaaaggcc agataagagg gttgagatag accaggcgcg    960
gtggctcatg cctgtaatcc cagcactttg ggaggccgag gtggtggat catgaagtca   1020 agagattgag gccatcctgg ctaacacggt gaaaccctgt ctctacttaa aaaaaaaaa    1080
```

-continued

```
tttccaaaaa attagccggg cacggtggtg ggcgcctgta gtcccagcta ctcgggaggc   1140
tgaggcggga gaatggtgtg aacctgggag gtggagcttg cagtgagccg acattgtgcc   1200
actgcactcc agcctgggtg acagagtgag actccgtctc aaaaaaataa aaaaagttgg   1260
gacagggggt ccttgcgtga tgatggagag agatccaccc gctggtagca tggtgctgga   1320
ggctgacagg tggaggaggt ggggcagggt ctgtccgagt gcctagagga agagtaaacc   1380
ttccagagat gggggaccca gaaggaagcg cagagtgggg ttgggggaag gggataccgg   1440
tggtcagaag aaatttatta acagtggatg ggataagtct gtgtctggag gatcctggt    1500
ggaggcagaa gggtcctgcc tcacctggat tctctcactc cctccccaga ctgcagccga   1560
accctggtcc ctcctccaca atgtggcttc tcctcactct tccttcctg ctggcatcca    1620
caggtgaggt ggccccagga gggggccagg tctgtgggag caggtgcccc cttcccaagc   1680
atgtctgggc ccagtgatct gccagcccct acctcaccca gagaccacta aagatccttc   1740
cttcaccctc cacctgtgcc aatgtcccta agcccttacc gtcaggtgct ggtgctgctg   1800
ctctggagtc gctatgttgc ctggggcctc tcgctgccca cgacaaggaa cacggtcctg   1860
gggttacaca aacctgagct gagtcctggg gcaaccgctt ccttgctgtg tgtccttgag   1920
ggaactgctt cacctctctg ggcttcgaat gccttctcta taagacagca cccacttgag   1980
acaataacag tgaggtctca atagcataac agaggtaata tacatagcaa gcattagaca   2040
agtgctgaga ggccaacagc acagacagac tccagcttga gtcccacacc tgccactccc   2100
tgtctcttac agggtctttg aggggattaa atgtggttgt gtgtgaggca gaagcataag   2160
cctggcccag gtagtgcccc ttcaggtgtg caagccaggc acggtgctta gagcttacat   2220
acaacgtcta tgtgtggtgg gcaccaccga cctcatttga caagggaagg ggctgtggct   2280
cagagggacg gccacaacat caaggtcacc ttgggtgtca ggcaaactcc agattgaact   2340
cagctgccac acaccaagaa attaattgta acctgatgcc tctcttctgg agaaattggg   2400
gggtggactt tcattaacgt tctgccacaa atgaccctca ctcctggggg ccctgagac    2460
ccccacgcct ccagcctccc ctccggctct ctctgtgcac tcacctacct gcctcgcgcc   2520
tgcctgctgc gcccagctgg ggcctccacc ttcctctggc ttggactggc caggtgcagc   2580
ctcggtgccc agctgttcag cccgtaccct ccgcccttcg gaggacgacc tcacccttcc   2640
tttgttaagc cccttgtcca ccacatccgc attcccctgg tctcacgggg gcctttggcc   2700
cagttcctga ctgtgatggg gagagtgtgg gcatttggtc tggctgtgca atcctgccc    2760
ctgtgtgggt gggagtgtgc atggcttcaa ccttcagggg atgcatccac attgcccagt   2820
ggagaggggt cctggtcctg tgaccttgaa tgtctctaat catgtcctta agcataatgc   2880
cattctgtgt gtgtgtgtgt gtgtgtgtgt gtacatgcac gtgtgcagtg ggtatacaag   2940
gccctgtatg ttcacatcct ctccacatgc atgagccaga tccccatatg tgaaacccaa   3000
tcagtgactc cacagatctg gcttggggc tgatctagag atggataaat atgtcctgcc     3060
ctggctgcct ctggcttcag ctgcatgtct ttgaccttga atgccagcc ccgtgtctgg    3120
gtgctgcccc agacagcaag tccacatctg agtgttggcc ttctggttg gtgtctgcag    3180
ctctaactct acaaaatgtc ttgtgggtga atcacggttt taaccttgac ttttttttgt   3240
ttgtttggtt ttttttgaga cggagtctcg ctctgccgcc caagctggag ttcagtggtg   3300
caacctcagc tcactgcaac ctccgcctcc caggttcaag caattctgtc tctgcctccc   3360
gagtagctag aattacaggc acgcaccacc acgcccagct gatttttgta tttttatta    3420
```

```
tttatttatt tatttttag tagagacggg atttcacgat gttggccagg ctggtctcaa    3480
actcctgacc tcaggtgatc cacccacctc ggccttggcc tcccaaagtg ctgggattac    3540
aggcgtgagc caccacacct ggccaacctt gactatttat tataggtaat tctgtgcaga    3600
tgtctgactt atgttggcca tctccaggat ggacctgaac tttcacacgt atgtccctgt    3660
gactaaatcc aggtgtcatt tgcaaaaaac aactaatatt attaagtagc taccagggct    3720
aggtatcact caccatacat acacacatgc acacacacac atacacattc ctacctcatc    3780
cttacaacaa tcttcatttt acagatgagg aaacagaggc acagacaggt cgaataactt    3840
actcaaagtt tcacagctag tacattcgaa cccaggctta aggaccatc tttgtccaga    3900
ccctgtatgc aagtgtctgt gacactggat gccaagactc acactagaga tgttgaattt    3960
aggtctgaac aatatccaat tctgtgtgtg tgtttgtgtg tgcatgtgtg tgtgtgtatg    4020
tattcatgtc ttaaccatcc atattcatat acacatatga acatctgtgc tgtgattctt    4080
tttttttttt tttttttttt tttgagatgg agtttcactc ttgtcaccca ggctggagtg    4140
caatggagca acctccgctc actgcaatct ccgcctcccg ggttcaagcg attttcctgc    4200
ctcagcctcc agagtagctg gattacagg cacccgccac catgcccagc taatttttg     4260
tattttgtt agagacaggg tttccccata ttggccaggc tggtctcgaa ctcctgacct    4320
caggtgatcc acccgcctcg gcctcccaaa gtgctgggat tacaggcatg agccaccgtg    4380
cccagcctgt gctgtgattc ttgaagctgc aacccatgtg catgcaagtg aatttcagct    4440
tccagtcctg tccatagctg tacctaagtg tggaagctgg atgtgcatgt atgcatgtcc    4500
atgaccttgt atagccacat ctgggactca tactgcacac tgaatttggc tgacatgtcc    4560
agactctggg gccaaggctg ggtcacacat actgagtggc cacatgcgtt tgacgtctgt    4620
gacaatttgg tgaccgtgaa tgactggttt caagtgacca cctgtctgaa cctgtatcca    4680
gtgcccctgt ctccaccccc aaccacagag gacttcttgc cctctggtct gttcccttc     4740
ctctctctcc cagagtctta tagcaaatgg ggtgggggct agagttctgg agaaaacagg    4800
cagcggttgt aaataaacaa cagggcaggc ggagcatggt ggctcacacc tgtaatccca    4860
gcactttggg aggctgaggc gggcagagca tttgaagtca gaagtttgag actacctggc    4920
taacatggtg agacctcgtc tctactaaaa atacaaaaat tagccaggtg tggtggcggg    4980
cacctcagct actcgggagg ctgaggcagg aggatcactt gaacccagga ggcggaagtt    5040
gcagtgagct gagatcatgc cactgcactc cagcctgggc aaaagagtga gactccgtct    5100
caaaaacaac aacaacaaca aaacaaaaaa cagggcaggt tgtcttgaga agttagggga    5160
aaggcatagg catatagtag ttagggcagg gtgcaaggaa ggtgtaggag gcaatgtaaa    5220
cgtccctgtc ctcaggcatc ctctacccct tctcttagca gcccaggatg gtgacaagtt    5280
gctggaaggt gacgagtgtg caccccactc ccagccatgg caagtggctc tctacgagcg    5340
tggacgcttt aactgtggcg cttccctcat ctccccacac tgggtgctgt ctgcggccca    5400
ctgccaaagc cggtatgaag gcaggggctc agggtcctga gggagcctgg ttcgggggga    5460
agagctccta gatttggggg aagacggagg cagacgccag aactcctggg ttctgaaaga    5520
cgaggaggcc ggatgtcaag cccctgggtt aggaaggagt gtgtgtttca aagccttcga    5580
tctctgaagg aggaaggaga agactagttc cagcttttga gcctcagttc tagggatgtg    5640
agaatcctgg attcggggac agaccaggag ggggctggga gtagttggag gggatcgagt    5700
tctaggagtg tgcctgactt cagactcgtt ggtccttgag gagcagggc tggaaccatt     5760
ggcttcaggg tcttgggaaa aggtaatggg atgtcgagat ttctaaaggg tcgggagacc    5820
```

```
tcgggttgcc cactctttga tctttctgtc ctctacttgc gggtaaccac tggcccgcac    5880
tccactggcg ggaaaaccac tcgcccgcac agcttcatga gagtgcgcct gggagagcac    5940
aacctgcgca agcgcgatgg cccagagcaa ctacggacca cgtctcgggt cattccacac    6000
ccgcgctacg aagcgcgcag ccaccgcaac gacatcatgt tgctgcgcct agtccagccc    6060
gcacgcctga accccaggt gcgccccgcg gtgctaccca cgcgttgccc ccacccgggg    6120
gaggcctgtg tggtgtctgg ctggggcctg gtgtcccaca acgagcctgg gaccgctggg    6180
agccccggt cacaaggtgc gtgaaaggat ggagctggat gcgaggcctc aaggaatcct    6240
atgctccagg gctcttgggc ggaggggaca agggccggaa tttatggatc tgctccaagt    6300
ccactgtctt ccccagtgag tctcccagat acgttgcatt gtgccaacat cagcattatc    6360
tcggacacat cttgtgacaa gagctaccca gggcgcctga caaacaccat ggtgtgtgca    6420
ggcgcgagg gcagaggcgc agaatcctgt gaggtcagag cctagagggg ccatcaggcg    6480
gaagaagagg gatgggaca ggtgtgggag tccggatggg gttggatttt ctttgctttg    6540
ggccagagaa gatgctaggg ttaggcttgg agatggagta ggaagagaag ttagaatagg    6600
ggtgaggttg gagttggggt tataggtggg gattgcgttg tttgaggtgg ataactgtga    6660
tagttagttt gagatggcat gggttggggt tgagaatggg aatggtttgg tttgattctg    6720
ggtgggaaat acgtcagggt tgaattggga tgaggtagat tttgtttgga atgcagaaga    6780
catgaagatt gagattggat tttgagatgg gcatgggttt gatttgattt tgaatggtga    6840
ggatgtgggc tgagttggat ttaacttagt acagttgcac tggagttgca tgggggtgag    6900
attggatata ggttgggtga gttgtattga gctgtgttga attggggttg gggttggggt    6960
tgggttggct ctgtttggga taaactgggc tgtattgagt tgagttgggt tgggggttccc    7020
tgggatgggg atggattggg tttggggtga gattgcaaat ggtgattagg atgaggatga    7080
atccaggagg tttcactcaa cctgagaccc cctcttttcc ccacagggtg actctggggg    7140
acccctggtc tgtgggggca tcctgcaggg cattgtgtcc tggggtgacg tcccttgtga    7200
caacaccacc aagcctggtg tctataccaa agtctgccac tacttggagt ggatcaggga    7260
aaccatgaag aggaactgac tattctagcc tatctcctgt gcccctgact gagcagaagc    7320
ccccacagct ggccagcagc cccgcctgac atggaacaga acggagccat cccccaagac    7380
cctgtccaag gcccagatgt tagccaagga cttgtcccac ctgaggacaa agctggcgct    7440
caaggtcacc tgtttaatgc caagataaca aagcgctgat ccaagttgct ctgtaggaat    7500
ttctgtgact tttttctggg gtcaaagaga aaccccgaga cactgtacac tgttcctttt    7560
cacccaccac cccgatccct aggtgaggag aagcggcttg aagcagggct ccattcattc    7620
aacacacatg accacccgtg tgatcttgaa caagaggccc aatctcactt cgccttggtt    7680
tccttatctg taaaatgaga ccatcttatt gctgacttca aagggctgtt gtgaggatta    7740
aatgagatga ttcgtctgaa ctgattaaaa tcgtgtctgg cactgagtaa ataccctcta    7800
tctctggatc ccagttaaag gacctaacag acactagatt accaagaatg cttttctt    7860
taaggtttag ttctgggccg gcatggtgg ctcacacctg taatcccagc actttgggag    7920
gccaaggcgg gcggctcact tgaggtcagg agtgcaagac cagcctggcc aacatggtga    7980
aaccccatct ctactaaaaa tactaaaaaa atttagccgg gcgtggtggc acgcgactgt    8040
aatcctagct acttgggagg gtgatgtggg aggatcgctt gaacttagga ggcaggagtt    8100
gcagtgagcc gagatcgcgc cactgcactc cagcctggtg acagagcaag actccatctc    8160
```

-continued

| | |
|---|---|
| agaaaaaaaa aaaaaaaaaa aaagatttag ttctgggctt cctggtagcc atggcaaaaa | 8220 |
| ggcaaatact gtcctttcct tagccaggtc cctgatatac agcagaggct ggaactctga | 8280 |
| gctgctttga ttttaccaaa aagccaagac aacctgttgg aagccatatgg gtttaccatt | 8340 |
| gaggctgcag gaatctagtt cctaattatc ttcagagacc acaaaatgtg atgttcaagg | 8400 |
| tcgctgaatg ttgaagtaca tgaacctggc tcgtgagacc taaatattgt actggtggtg | 8460 |
| gggggaagg gtcattggaa tctgtggtta gcctgatctt gacctgcgag ggaaggttgt | 8520 |
| ccagatctct ggactttgga ggaccgacgt tgagcaccat aatgggagca gaagtgcgag | 8580 |
| gtctttgaga ccccgcttgt tggggcggcg ccggatttgg atgctaaaaa ttacctggga | 8640 |
| accctgaata catctgggtt gggcgcacaa tgtgtggctc cccacacatc tttaggaaca | 8700 |
| catttgggca acccggtggg agtgaacggc ctggc | 8735 |

<210> SEQ ID NO 2
<211> LENGTH: 1278
<212> TYPE: DNA
<213> ORGANISM: Homo sapiens

<400> SEQUENCE: 2

| | |
|---|---|
| atgtggcttc tcctcactct ctccttcctg ctggcatcca cagcagccca ggatggtgac | 60 |
| aagttgctgg aaggtgacga gtgtgcaccc cactcccagc catggcaagt ggctctctac | 120 |
| gagcgtggac gctttaactg tggcgcttcc ctcatctccc cacactgggt gctgtctgcg | 180 |
| gcccactgcc aaagccgctt catgagagtg cgcctgggag agcacaacct gcgcaagcgc | 240 |
| gatggcccag agcaactacg gaccacgtct cgggtcattc cacacccgcg ctacgaagcg | 300 |
| cgcagccacc gcaacgacat catgttgctg cgcctagtcc agcccgcacg cctgaacccc | 360 |
| caggtgcgcc ccgcggtgct acccacgcgt tgcccccacc cggggaggc ctgtgtggtg | 420 |
| tctggctggg gcctggtgtc ccacaacgag cctgggaccg ctgggagccc ccggtcacaa | 480 |
| gtgagtctcc cagatacgtt gcattgtgcc aacatcagca ttatctcgga cacatcttgt | 540 |
| gacaagagct acccagggcg cctgacaaac accatggtgt gtgcaggcgc ggagggcaga | 600 |
| ggcgcagaat cctgtgaggg tgactctggg ggaccctgg tctgtggggg catcctgcag | 660 |
| ggcattgtgt cctggggtga cgtcccttgt gacaacacca ccaagcctgg tgtctatacc | 720 |
| aaagtctgcc actacttgga gtggatcagg gaaaccatga gaggaactg actattctag | 780 |
| cctatctcct gtgcccctga ctgagcagaa gcccccacag ctggccagca gccccgcctg | 840 |
| acatggaaca gaacggagcc atcccccaag accctgtcca aggcccagat gttagccaag | 900 |
| gacttgtccc acctgaggac aaagctggcg ctcaaggtca cctgtttaat gccaagataa | 960 |
| caaagcgctg atccaagttg ctctgtagga atttctgtga cttttttctg gggtcaaaga | 1020 |
| gaaaccccga gacactgtac actgttcctt ttcacccacc accccgatcc ctaggtgagg | 1080 |
| agaagcggct tgaagcaggg ctccattcat tcaacacaca tgaccacccg tgtgatcttg | 1140 |
| aacaagaggc ccaatctcac ttcgccttgg tttccttatc tgtaaaatga gaccatctta | 1200 |
| ttgctgactt caaagggctg ttgtgaggat taaatgagat gattcgtctg aactgattaa | 1260 |
| aatcgtgtct ggcactga | 1278 |

<210> SEQ ID NO 3
<211> LENGTH: 1124
<212> TYPE: DNA
<213> ORGANISM: Homo sapiens

<400> SEQUENCE: 3

```
atgtggcttc tcctcactct ctccttcctg ctggcatcca cagcagccca ggatggtgac      60
aagttgctgg aaggtgacga gtgtgcaccc cactcccagc catggcaagt ggctctctac     120
gagcgtggac gctttaactg tggcgcttcc ctcatctccc cacactgggt gctgtctgcg     180
gcccactgcc aaagccgctt catgagagtg cgcctgggag agcacaacct gcgcaagcgc     240
gatggcccag agcaactacg gaccacgtct cgggtcattc cacacccgcg ctacgaagcg     300
cgcagccacc gcaacgacat catgttgctg cgcctagtcc agcccgcacg cctgaacccc     360
cagtgagtct cccagatacg ttgcattgtg ccaacatcag cattatctcg dacacatctt     420
gtgacaagag ctacccaggg cgcctgacaa acaccatggt gtgtgcaggc gcggagggca     480
gaggcgcaga atcctgtgag ggtgactctg ggggacccct ggtctgtggg ggcatcctgc     540
agggcattgt gtcctggggt gacgtccctt gtgacaacac caccaagcct ggtgtctata     600
ccaaagtctg ccactacttg gagtggatca gggaaaccat gaagaggaac tgactattct     660
agcctatctc ctgtgcccct gactgagcag aagcccccac agctggccag cagccccgcc     720
tgacatggaa cagaacggag ccatcccccca gaccctgtc caaggcccag atgttagcca     780
aggacttgtc ccacctgagg acaaagctgg cgctcaaggt cacctgttta atgccaagat     840
aacaaagcgc tgatccaagt tgctctgtag gaatttctgt gacttttttc tggggtcaaa     900
gagaaacccc gagacactgt acactgttcc ttttcaccca ccaccccgat ccctaggtga     960
ggagaagcgg cttgaagcag ggctccattc attcaacaca catgaccacc cgtgtgatct    1020
tgaacaagag gcccaatctc acttcgcctt ggtttcctta tctgtaaaat gagaccatct    1080
tattgctgac ttcaaagggc tgttgtgagg attaaatgag atga                     1124

<210> SEQ ID NO 4
<211> LENGTH: 1105
<212> TYPE: DNA
<213> ORGANISM: Homo sapiens

<400> SEQUENCE: 4
atgtggcttc tcctcactct ctccttcctg ctggcatcca cagcagccca ggatggtgac      60
aagttgctgg aaggtgacga gtgtgcaccc cactcccagc catggcaagt ggctctctac     120
gagcgtggac gctttaactg tggcgcttcc ctcatctccc cacactgggt gctgtctgcg     180
gcccactgcc aaagccgctt catgagagtg cgcctgggag agcacaacct gcgcaagcgc     240
gatggcccag agcaactacg gaccacgtct cgggtcattc cacacccgcg ctacgaagcg     300
cgcagccacc gcaacgacat catgttgctg cgcctagtcc agcccgcacg cctgaacccc     360
caggtgcgcc ccgcggtgct acccacgcgt tgccccacc cggggaggc ctgtgtggtg     420 tctggctggg gcctggtgtc ccacaacgag cctgggaccg ctgggagccc ccggtcacaa     480
gggtgactct gggggacccc tggtctgtgg ggcatcctg cagggcattg tgtcctgggg     540
tgacgtccct tgtgacaaca ccaccaagcc tggtgtctat accaaagtct gccactactt     600
ggagtggatc agggaaacca tgaagaggaa ctgactattc tagcctatct cctgtgcccc     660
tgactgagca gaagccccca gctggccag gcagcccgc ctgacatgga acagaacgga     720
gccatccccc aagaccctgt ccaaggccca gatgttagcc aaggacttgt cccacctgag     780
gacaaagctg gcgctcaagg tcacctgttt aatgccaaga taacaaagcg ctgatccaag    840
ttgctctgta ggaatttctg tgactttttt ctggggtcaa agagaaaccc cgagacactg    900
tacactgttc cttttcaccc accaccccga tccctaggtg aggagaagcg gcttgaagca    960
```

```
gggctccatt cattcaacac acatgaccac ccgtgtgatc ttgaacaaga ggcccaatct   1020
cacttcgcct tggtttcctt atctgtaaaa tgagaccatc ttattgctga cttcaaaggg   1080
ctgttgtgag gattaaatga gatga                                         1105
```

<210> SEQ ID NO 5
<211> LENGTH: 987
<212> TYPE: DNA
<213> ORGANISM: Homo sapiens

<400> SEQUENCE: 5

```
atgtggcttc tcctcactct ctccttcctg ctggcatcca cagcagccca ggatggtgac     60
aagttgctgg aaggtgacga gtgtgcaccc cactcccagc catggcaagt ggctctctac    120
gagcgtggac gctttaactg tggcgcttcc ctcatctccc cacactgggt gctgtctgcg    180
gcccactgcc aaagccgctt catgagagtg cgcctgggag agcacaacct gcgcaagcgc    240
gatgggccag agcaactacg gaccacgtct cgggtcattc cacacccgcg ctacgaagcg    300
cgcagccacc gcaacgacat catgttgctg cgcctagtcc agcccgcacg cctgaacccc    360
cagggtgact ctgggggacc cctggtctgt ggggcatcc tgcagggcat tgtgtcctgg    420
ggtgacgtcc cttgtgacaa caccaccaag cctggtgtct ataccaaagt ctgccactac    480
ttggagtgga tcagggaaac catgaagagg aactgactat ctagcctat ctcctgtgcc    540 cctgactgag cagaagcccc cacagctggc cagcagcccc gcctgacatg aacagaacg    600 gagccatccc ccaagaccct gtccaaggcc cagatgttag ccaaggactt gtcccacctg    660
aggacaaagc tggcgctcaa ggtcacctgt ttaatgccaa gataacaaag cgctgatcca    720
agttgctctg taggaatttc tgtgactttt ttctggggtc aaagagaaac cccgagacac    780
tgtacactgt tcctttcac ccaccacccc gatccctagg tgaggagaag cggcttgaag    840
cagggctcca ttcattcaac acacatgacc accgtgtga tcttgaacaa gaggcccaat    900
ctcacttcgc cttggtttcc ttatctgtaa aatgagacca tcttattgct gacttcaaag    960
ggctgttgtg aggattaaat gagatga                                        987
```

<210> SEQ ID NO 6
<211> LENGTH: 256
<212> TYPE: PRT
<213> ORGANISM: Homo sapiens

<400> SEQUENCE: 6

```
Met Trp Leu Leu Leu Thr Leu Ser Phe Leu Leu Ala Ser Thr Ala Ala
1               5                   10                  15

Gln Asp Gly Asp Lys Leu Leu Glu Gly Asp Glu Cys Ala Pro His Ser
            20                  25                  30

Gln Pro Trp Gln Val Ala Leu Tyr Glu Arg Gly Arg Phe Asn Cys Gly
        35                  40                  45

Ala Ser Leu Ile Ser Pro His Trp Val Leu Ser Ala Ala His Cys Gln
    50                  55                  60

Ser Arg Phe Met Arg Val Arg Leu Gly Glu His Asn Leu Arg Lys Arg
65                  70                  75                  80

Asp Gly Pro Glu Gln Leu Arg Thr Thr Ser Arg Val Ile Pro His Pro
                85                  90                  95

Arg Tyr Glu Ala Arg Ser His Arg Asn Asp Ile Met Leu Leu Arg Leu
            100                 105                 110

Val Gln Pro Ala Arg Leu Asn Pro Gln Val Arg Pro Ala Val Leu Pro
        115                 120                 125
```

```
Thr Arg Cys Pro His Pro Gly Glu Ala Cys Val Val Ser Gly Trp Gly
        130                 135                 140

Leu Val Ser His Asn Glu Pro Gly Thr Ala Gly Ser Pro Arg Ser Gln
145                 150                 155                 160

Val Ser Leu Pro Asp Thr Leu His Cys Ala Asn Ile Ser Ile Ile Ser
                165                 170                 175

Asp Thr Ser Cys Asp Lys Ser Tyr Pro Gly Arg Leu Thr Asn Thr Met
            180                 185                 190

Val Cys Ala Gly Ala Glu Gly Arg Gly Ala Glu Ser Cys Glu Gly Asp
        195                 200                 205

Ser Gly Gly Pro Leu Val Cys Gly Gly Ile Leu Gln Gly Ile Val Ser
    210                 215                 220

Trp Gly Asp Val Pro Cys Asp Asn Thr Thr Lys Pro Gly Val Tyr Thr
225                 230                 235                 240

Lys Val Cys His Tyr Leu Glu Trp Ile Arg Glu Thr Met Lys Arg Asn
                245                 250                 255

<210> SEQ ID NO 7
<211> LENGTH: 121
<212> TYPE: PRT
<213> ORGANISM: Homo sapiens

<400> SEQUENCE: 7

Met Trp Leu Leu Leu Thr Leu Ser Phe Leu Leu Ala Ser Thr Ala Ala
1               5                   10                  15

Gln Asp Gly Asp Lys Leu Leu Glu Gly Asp Glu Cys Ala Pro His Ser
            20                  25                  30

Gln Pro Trp Gln Val Ala Leu Tyr Glu Arg Gly Arg Phe Asn Cys Gly
        35                  40                  45

Ala Ser Leu Ile Ser Pro His Trp Val Leu Ser Ala Ala His Cys Gln
    50                  55                  60

Ser Arg Phe Met Arg Val Arg Leu Gly Glu His Asn Leu Arg Lys Arg
65                  70                  75                  80

Asp Gly Pro Glu Gln Leu Arg Thr Thr Ser Arg Val Ile Pro His Pro
                85                  90                  95

Arg Tyr Glu Ala Arg Ser His Arg Asn Asp Ile Met Leu Leu Arg Leu
            100                 105                 110

Val Gln Pro Ala Arg Leu Asn Pro Gln
        115                 120

<210> SEQ ID NO 8
<211> LENGTH: 161
<212> TYPE: PRT
<213> ORGANISM: Homo sapiens

<400> SEQUENCE: 8

Met Trp Leu Leu Leu Thr Leu Ser Phe Leu Leu Ala Ser Thr Ala Ala
1               5                   10                  15

Gln Asp Gly Asp Lys Leu Leu Glu Gly Asp Glu Cys Ala Pro His Ser
            20                  25                  30

Gln Pro Trp Gln Val Ala Leu Tyr Glu Arg Gly Arg Phe Asn Cys Gly
        35                  40                  45

Ala Ser Leu Ile Ser Pro His Trp Val Leu Ser Ala Ala His Cys Gln
    50                  55                  60

Ser Arg Phe Met Arg Val Arg Leu Gly Glu His Asn Leu Arg Lys Arg
65                  70                  75                  80
```

```
Asp Gly Pro Glu Gln Leu Arg Thr Thr Ser Arg Val Ile Pro His Pro
                 85                  90                  95

Arg Tyr Glu Ala Arg Ser His Arg Asn Asp Ile Met Leu Leu Arg Leu
            100                 105                 110

Val Gln Pro Ala Arg Leu Asn Pro Gln Val Arg Pro Ala Val Leu Pro
        115                 120                 125

Thr Arg Cys Pro His Pro Gly Glu Ala Cys Val Val Ser Gly Trp Gly
    130                 135                 140

Leu Val Ser His Asn Glu Pro Gly Thr Ala Gly Ser Pro Arg Ser Gln
145                 150                 155                 160

Gly

<210> SEQ ID NO 9
<211> LENGTH: 171
<212> TYPE: PRT
<213> ORGANISM: Homo sapiens

<400> SEQUENCE: 9

Met Trp Leu Leu Leu Thr Leu Ser Phe Leu Leu Ala Ser Thr Ala Ala
1               5                   10                  15

Gln Asp Gly Asp Lys Leu Leu Glu Gly Asp Glu Cys Ala Pro His Ser
            20                  25                  30

Gln Pro Trp Gln Val Ala Leu Tyr Glu Arg Gly Arg Phe Asn Cys Gly
        35                  40                  45

Ala Ser Leu Ile Ser Pro His Trp Val Leu Ser Ala Ala His Cys Gln
    50                  55                  60

Ser Arg Phe Met Arg Val Arg Leu Gly Glu His Asn Leu Arg Lys Arg
65                  70                  75                  80

Asp Gly Pro Glu Gln Leu Arg Thr Thr Ser Arg Val Ile Pro His Pro
                85                  90                  95

Arg Tyr Glu Ala Arg Ser His Arg Asn Asp Ile Met Leu Leu Arg Leu
            100                 105                 110

Val Gln Pro Ala Arg Leu Asn Pro Gln Gly Asp Ser Gly Gly Pro Leu
        115                 120                 125

Val Cys Gly Gly Ile Leu Gln Gly Ile Val Ser Trp Gly Asp Val Pro
    130                 135                 140

Cys Asp Asn Thr Thr Lys Pro Gly Val Tyr Thr Lys Val Cys His Tyr
145                 150                 155                 160

Leu Glu Trp Ile Arg Glu Thr Met Lys Arg Asn
                165                 170

<210> SEQ ID NO 10
<211> LENGTH: 8
<212> TYPE: PRT
<213> ORGANISM: Artificial Sequence
<220> FEATURE:
<223> OTHER INFORMATION: peptide/amino acid segment derived from human
      sequence

<400> SEQUENCE: 10

His Asn Glu Pro Gly Thr Ala Gly
1               5

<210> SEQ ID NO 11
<211> LENGTH: 1580
<212> TYPE: DNA
<213> ORGANISM: Homo sapiens
```

<400> SEQUENCE: 11

```
agaatgggtg ctgtgggatt caggggagac acctgttagg tgttgggggcc tcccagaaga    60
ggtgggggca gagtgtcaga ggacaaagat gaatttggaa gatatgggga agaaggattt   120
caattcaccc tcaaagcttc ctgaggcctc ccgtgggtcg ggccctgcag tactggagac   180
ccagagtgga gtcagaccag ctcctcgggg agctgccagt ctcgtagggg aggcagacac   240
cactgagggt caggggaggt cagagaaggc ctcaaggagg aagcggggct ggaagggaat   300
ggcgttggat atgcggtggg aggaatagcc taagcatgaa atggcaggag ggaaaatggc   360
agcactggct gcgtctagga caaggtcatg ggagacccag ggagaggggc tggaagggaa   420
gaagccactt ttgtccttga aagtgaggct ggagccaggc aactcatgcc tgtaatccca   480
gcactttggg aggctgaggc gggtggatca ctagaggtca ggagttcaag accagcctgg   540
ccaacatggt gaaactccgt ctctactaaa attacaaaaa ttagctgggc gtggtggcac   600
acacctgtaa tcccaattgc ttgggaggct gaggcaggaa atctcttga cccagaagg   660
cagaggttac agtgagcgga gatcacgcca ctccactcca acctgggcta cagagccaga   720
ctccgtctca aaaaaaaaa aaaaaagaa aaaaaagaa agaaagtgaa tttgaagagc   780
tggactttat cctggtggtg ccaaggatcc atggagggtg gtgagcaggg gagggcaca   840
gccagctcca gatgtagaaa gacccttttgg ggtcatggct ggagggcaag ctggtggagg   900
ggactggact ggaggggac ccaaaaggcc agataagagg gttgagatag accaggcgcg   960
gtggctcatg cctgtaatcc cagcactttg ggaggccgag gtgggtggat catgaagtca  1020
agagattgag gccatcctgg ctaacacggt gaaaccctgt ctctacttaa aaaaaaaaaa  1080
tttccaaaaa attagccggg cacggtggtg ggcgcctgta gtcccagcta ctcgggaggc  1140
tgaggcggga gaatggtgtg aacctgggag gtggagcttg cagtgagccg acattgtgcc  1200
actgcactcc agcctgggtg acagagtgag actccgtctc aaaaaaataa aaaaagttgg  1260
gacaggggt ccttgcgtga tgatggagag agatccaccc gctggtagca tggtgctgga  1320
ggctgacagg tggaggaggt ggggcagggt ctgtccgagt gcctagagga agagtaaacc  1380
ttccagagat gggggaccca gaaggaagcg cagagtgggg ttgggggaag gggataccgg  1440
tggtcagaag aaatttatta acagtggatg ggataagtct gtgtctggag ggatcctggt  1500
ggaggcagaa gggtcctgcc tcacctggat tctctcactc cctccccaga ctgcagccga  1560
accctggtcc ctcctccaca                                               1580
```

<210> SEQ ID NO 12
<211> LENGTH: 43
<212> TYPE: DNA
<213> ORGANISM: Homo sapiens

<400> SEQUENCE: 12

```
atgtggcttc tcctcactct ctccttcctg ctggcatcca cag                      43
```

<210> SEQ ID NO 13
<211> LENGTH: 3635
<212> TYPE: DNA
<213> ORGANISM: Homo sapiens

<400> SEQUENCE: 13

```
gtgaggtggc cccaggaggg ggccaggtct gtgggagcag gtgcccccctt cccaagcatg    60
tctgggccca gtgatctgcc agcccctacc tcacccagag accactaaag atccttcctt   120
caccctccac ctgtgccaat gtccctaagc ccttaccgtc aggtgctggt gctgctgctc   180
```

```
tggagtcgct atgttgcctg gggcctctcg ctgcccacga caaggaacac ggtcctgggg    240
ttacacaaac ctgagctgag tcctggggca accgcttcct tgctgtgtgt ccttgaggga    300
actgcttcac ctctctgggc ttcgaatgcc ttctctataa gacagcaccc acttgagaca    360
ataacagtga ggtctcaata gcataacaga ggtaatatac atagcaagca ttagacaagt    420
gctgagaggc aacagcaca gacagactcc agcttgagtc ccacacctgc cactccctgt     480
ctcttacagg gtcttttgagg ggattaaatg tggttgtgtg tgaggcagaa gcataagcct   540
ggcccaggta gtgccccttc aggtgtgcaa gccaggcacg gtgcttagag cttacataca    600
acgtctatgt gtggtgggca ccaccgacct catttgacaa gggaaggggc tgtggctcag    660
agggacggcc acaacatcaa ggtcaccttg ggtgtcaggc aaactccaga ttgaactcag    720
ctgccacaca ccaagaaatt aattgtaacc tgatgcctct cttctggaga aattgggggg    780
tggactttca ttaacgttct gccacaaatg accctcactc ctgggggccc ctgagacccc    840
cacgcctcca gcctcccctc cggctctctc tgtgcactca cctacctgcc tcgcgcctgc    900
ctgctgcgcc cagctggggc ctccaccttc tctggcttg gactggccag gtgcagcctc     960
ggtgcccagc tgttcagccc gtaccctccg cccttcggag gacgacctca cccttccttt   1020
gttaagcccc ttgtccacca catccgcatt cccctggtct cacggggggcc tttggcccag  1080 ttcctgactg tgatggggag agtgtgggca tttggtctgg ctgtgcaaat cctgcccctg   1140
tgtgggtggg agtgtgcatg gcttcaacct tcagggggatg catccacatt gcccagtgga   1200
gaggggtcct ggtcctgtga ccttgaatgt ctctaatcat gtccttaagc ataatgccat   1260
tctgtgtgtg tgtgtgtgtg tgtgtgtgta catgcacgtg tgcagtgggt atacaaggcc   1320
ctgtatgttc acatcctctc cacatgcatg agccagatcc ccatatgtga aacccaatca   1380
gtgactccac agatctggct tggggggctga tctagagatg gataaatatg tcctgccctg   1440
gctgcctctg gcttcagctg catgtctttg accttgaatg cccagccccg tgtctgggtg   1500
ctgccccaga cagcaagtcc acatctgagt gttggccttc tgggttggtg tctgcagctc   1560
taactctaca aaatgtcttg tgggtgaatc acggttttaa ccttgacttt ttttttgtttg   1620 tttggttttt tttgagacgg agtctcgctc tgccgcccaa gctggagttc agtggtgcaa   1680
cctcagctca ctgcaacctc cgcctcccag gttcaagcaa ttctgtctct gcctcccgag   1740
tagctagaat tacaggcacg caccaccacg cccagctgat ttttgtattt ttatttattt   1800
atttatttat tttttagtag agacgggatt tcacgatgtt ggccaggctg gtctcaaact   1860
cctgacctca ggtgatccac ccacctcggc cttggcctcc caaagtgctg ggattacagg   1920
cgtgagccac cacacctggc caaccttgac tatttattat aggtaattct gtgcagatgt   1980
ctgacttatg ttggccatct ccaggatgga cctgaacttt cacacgtatg tccctgtgac   2040
taaatccagg tgtcatttgc aaaaaacaac taatatattt aagtagctac cagggctagg   2100
tatcactcac catacataca cacatgcaca cacacacata cacattccta cctcatcctt   2160
acaacaatct tcatttttaca gatgaggaaa cagaggcaca gacaggtcga ataacttact   2220
caaagtttca cagctagtac attcgaaccc aggcttaagg acccatcttt gtccagaccc   2280
tgtatgcaag tgtctgtgac actggatgcc aagactcaca ctagagatgt tgaatttagg   2340
tctgaacaat atccaattct gtgtgtgtgt ttgtgtgtgc atgtgtgtgt gtgtatgtat   2400
tcatgtctta accatccata ttcatatata catatgaaca tctgtgctgt gattcttttt   2460
tttttttttt tttttttttt gagatggagt ttcactcttg tcacccaggc tggagtgcaa   2520
```

```
tggagcaacc tccgctcact gcaatctccg cctcccgggt tcaagcgatt ttcctgcctc   2580
agcctccaga gtagctggga ttacaggcac ccgccaccat gcccagctaa ttttttgtat   2640
ttttgttaga cagggtttt ccccatattg gccaggctgg tctcgaactc ctgacctcag    2700
gtgatccacc cgcctcggcc tcccaaagtg ctgggattac aggcatgagc caccgtgccc   2760
agcctgtgct gtgattcttg aagctgcaac ccatgtgcat gcaagtgaat tcagcttcc    2820 agtcctgtcc atagctgtac ctaagtgtgg aagctggatg tgcatgtatg catgtccatg   2880
accttgtata gccacatctg ggactcatac tgcacactga atttggctga catgtccaga   2940
ctctggggcc aagctgggt cacacatact gagtggccac atgcgtttga cgtctgtgac    3000
aatttggtga ccgtgaatga ctggtttcaa gtgaccacct gtctgaacct gtatccagtg   3060
cccctgtctc cacccccaac cacagaggac ttcttgccct ctggtctgtt ccccttcctc   3120
tctctcccag agtcttatag caaatggggt gggggctaga gttctggaga aaacaggcag   3180
cggttgtaaa taacaacag gcaggcgga gcatggtggc tcacacctgt aatcccagca     3240
ctttgggagg ctgaggcggg cagagcattt gaagtcagaa gtttgagact acctggctaa   3300
catggtgaga cctcgtctct actaaaaata caaaaattag ccaggtgtgg tggcgggcac   3360
ctcagctact cgggaggctg aggcaggagg atcacttgaa cccaggaggc ggaagttgca   3420
gtgagctgag atcatgccac tgcactccag cctgggcaaa agagtgagac tccgtctcaa   3480
aaacaacaac aacaacaaaa caaaaaacag gcagggtgt cttgagaagt taggggaaag    3540
gcataggcat atagtagtta gggcagggtg caaggaaggt gtaggaggca atgtaaacgt   3600
ccctgtcctc aggcatcctc taccccttct cttag                             3635

<210> SEQ ID NO 14
<211> LENGTH: 154
<212> TYPE: DNA
<213> ORGANISM: Homo sapiens

<400> SEQUENCE: 14
cagcccagga tggtgacaag ttgctggaag gtgacgagtg tgcacccac tcccagccat     60 ggcaagtggc tctctacgag cgtggacgct ttaactgtgg cgcttccctc atctccccac   120
actgggtgct gtctgcggcc cactgccaaa gccg                               154

<210> SEQ ID NO 15
<211> LENGTH: 500
<212> TYPE: DNA
<213> ORGANISM: Homo sapiens

<400> SEQUENCE: 15
gtatgaaggc aggggctcag ggtcctgagg gagcctggtt cgggggaag agctcctaga     60 tttgggggaa gacggaggca gacgccagaa ctcctgggtt ctgaaagacg aggaggccgg   120
atgtcaagcc cctgggttag gaaggagtgt gtgtttcaaa gccttcgatc tctgaaggag   180
gaaggagaag actagttcca gcttttgagc ctcagttcta gggatgtgag aatcctggat   240
tcggggacag accaggaggg ggctgggagt agttggaggg gatcgagttc taggagtgtg   300
cctgacttca gactcgttgg tccttgagga gcaggggctg gaaccattgg cttcagggtc   360
ttgggaaaag gtaatgggat gtcgagattt ctaaagggtc gggagacctc gggttgccca   420
ctctttgatc tttctgtcct ctacttgcgg gtaaccactg gcccgcactc cactggcggg   480
aaaaccactc gcccgcacag                                               500
```

<210> SEQ ID NO 16
<211> LENGTH: 284
<212> TYPE: DNA
<213> ORGANISM: Homo sapiens

<400> SEQUENCE: 16
cttcatgaga gtgcgcctgg gagagcacaa cctgcgcaag cgcgatggcc cagagcaact      60
acggaccacg tctcgggtca ttccacaccc gcgctacgaa gcgcgcagcc accgcaacga     120
catcatgttg ctgcgcctag tccagcccgc acgcctgaac ccccaggtgc gccccgcggt     180
gctacccacg cgttgccccc acccggggga ggcctgtgtg gtgtctggct ggggcctggt     240
gtcccacaac gagcctggga ccgctgggag cccccggtca caag                      284

<210> SEQ ID NO 17
<211> LENGTH: 119
<212> TYPE: DNA
<213> ORGANISM: Homo sapiens

<400> SEQUENCE: 17
tgcgtgaaag gatggagctg gatgcgaggc ctcaaggaat cctatgctcc agggctcttg      60
ggcggagggg acaagggccg gaatttatgg atctgctcca gtccactgt cttccccag      119

<210> SEQ ID NO 18
<211> LENGTH: 284
<212> TYPE: DNA
<213> ORGANISM: Homo sapiens

<400> SEQUENCE: 18
cttcatgaga gtgcgcctgg gagagcacaa cctgcgcaag cgcgatggcc cagagcaact      60
acggaccacg tctcgggtca ttccacaccc gcgctacgaa gcgcgcagcc accgcaacga     120
catcatgttg ctgcgcctag tccagcccgc acgcctgaac ccccaggtgc gccccgcggt     180
gctacccacg cgttgccccc acccggggga ggcctgtgtg gtgtctggct ggggcctggt     240
gtcccacaac gagcctggga ccgctgggag cccccggtca caag                      284

<210> SEQ ID NO 19
<211> LENGTH: 120
<212> TYPE: DNA
<213> ORGANISM: Homo sapiens

<400> SEQUENCE: 19
gtgcgtgaaa ggatggagct ggatgcgagg cctcaaggaa tcctatgctc cagggctctt      60
gggcggaggg gacaagggcc ggaatttatg gatctgctcc aagtccactg tcttccccag     120

<210> SEQ ID NO 20
<211> LENGTH: 137
<212> TYPE: DNA
<213> ORGANISM: Homo sapiens

<400> SEQUENCE: 20
tgagtctccc agatacgttg cattgtgcca acatcagcat tatctcggac acatcttgtg      60
acaagagcta cccagggcgc ctgacaaaca ccatggtgtg tgcaggcgcg gagggcagag     120
gcgcagaatc ctgtgag                                                    137

<210> SEQ ID NO 21
<211> LENGTH: 673
<212> TYPE: DNA
<213> ORGANISM: Homo sapiens

<400> SEQUENCE: 21

```
gtcagagcct agaggggcca tcaggcggaa gaagagggat ggggacaggt gtgggagtcc      60
ggatggggtt ggattttctt tgctttgggc cagagaagat gctagggtta ggcttggaga     120
tggagtagga agagaagtta gaatagggt gaggttggag ttggggttat aggtggggat      180
tgcgttgttt gaggtggata actgtgatag ttagtttgag atggcatggg ttggggttga     240
gaatgggaat ggtttggttt gattctgggt gggaaatacg tcaggttga attgggatga      300
ggtagatttt gtttgaatg cagaagacat gaagattgag attggatttt gagatgggca      360
tgggtttgat ttgattttga atggtgagga tgtgggctga gttggattta acttagtaca     420
gttgcactgg agttgcatgg gggtgagatt ggatataggt tgggtgagtt gtattgagct     480
gtgttgaatt ggggttgggg ttggggttgg gttggctctg tttgggataa actgggctgt     540
attgagttga gttgggttgg ggttccctgg gatggggatg gattgggttt ggggtgagat     600
tgcaaatggt gattaggatg aggatgaatc caggaggttt cactcaacct gagaccccct     660
cttttcccca cag                                                        673
```

<210> SEQ ID NO 22
<211> LENGTH: 1046
<212> TYPE: DNA
<213> ORGANISM: Homo sapiens

<400> SEQUENCE: 22

```
tgcgccccgc ggtgctaccc acgcgttgcc cccacccggg ggaggcctgt gtggtgtctg      60
gctgggcct ggtgtcccac aacgagcctg ggaccgctgg gagccccgg tcacaaggtg       120
cgtgaaagga tggagctgga tgcgaggcct caaggaatcc tatgctccag ggctcttggg     180
cggaggggac aagggccgga atttatggat ctgctccaag tccactgtct tccccagtga     240
gtctcccaga tacgttgcat tgtgccaaca tcagcattat ctcggacaca tcttgtgaca     300
agagctaccc agggcgcctg acaaacacca tggtgtgtgc aggcgcggag ggcagaggcg     360
cagaatcctg tgaggtcaga gcctagaggg gccatcaggc ggaagaagag gatgggacca    420
ggtgtgggag tccggatggg gttggatttt ctttgctttg gccagagaa gatgctaggg     480
ttaggcttgg agatggagta ggaagagaag ttagaatagg ggtgaggttg gagttggggt    540
tataggtggg gattgcgttg tttgaggtgg ataactgtga tagttagttt gagatggcat     600
gggttgggg tgagaatggg aatggtttgg tttgattctg ggtgggaaat acgtcagggt     660
tgaattggga tgaggtagat tttgtttgga atgcagaaga catgaagatt gagattggat     720
tttgagatgg gcatgggttt gatttgattt tgaatggtga ggatgtgggc tgagttggat     780
ttaacttagt acagttgcac tggagttgca tgggggtgag attggatata ggttgggtga     840
gttgtattga gctgtgttga attggggttg gggttggggt tggttggct ctgtttggga      900
taaactgggc tgtattgagt tgagttggt tggggttccc tgggatgggg atggattggg      960
tttggggtga gattgcaaat ggtgattagg atgaggatga atccaggagg tttcactcaa    1020
cctgagaccc cctctttttcc ccacag                                        1046
```

<210> SEQ ID NO 23
<211> LENGTH: 660
<212> TYPE: DNA
<213> ORGANISM: Homo sapiens

<400> SEQUENCE: 23

```
ggtgactctg ggggaccccct ggtctgtggg ggcatcctgc agggcattgt gtcctggggt     60
```

```
gacgtcccctt gtgacaacac caccaagcct ggtgtctata ccaaagtctg ccactacttg    120
gagtggatca gggaaaccat gaagaggaac tgactattct agcctatctc ctgtgcccct    180
gactgagcag aagcccccac agctggccag cagccccgcc tgacatggaa cagaacggag    240
ccatccccca agaccctgtc caaggcccag atgttagcca aggacttgtc ccacctgagg    300
acaaagctgg cgctcaaggt cacctgttta atgccaagat aacaaagcgc tgatccaagt    360
tgctctgtag gaatttctgt gacttttttc tggggtcaaa gagaaacccc gagacactgt    420
acactgttcc ttttcaccca ccacccccgat ccctaggtga ggagaagcgg cttgaagcag    480
ggctccattc attcaacaca catgaccacc cgtgtgatct tgaacaagag cccaatctc     540 acttcgcctt ggtttcctta tctgtaaaat gagaccatct tattgctgac ttcaaagggc    600
tgttgtgagg attaaatgag atgattcgtc tgaactgatt aaaatcgtgt ctggcactga    660
```

<210> SEQ ID NO 24
<211> LENGTH: 153
<212> TYPE: DNA
<213> ORGANISM: Homo sapiens

<400> SEQUENCE: 24

```
ggtgactctg ggggaccct ggtctgtggg ggcatcctgc agggcattgt gtcctggggt     60 gacgtcccctt gtgacaacac caccaagcct ggtgtctata ccaaagtctg ccactacttg    120
gagtggatca gggaaaccat gaagaggaac tga                                 153
```

<210> SEQ ID NO 25
<211> LENGTH: 244
<212> TYPE: PRT
<213> ORGANISM: Homo sapiens

<400> SEQUENCE: 25

```
Met Lys Lys Leu Met Val Val Leu Ser Leu Ile Ala Ala Ala Trp Ala
1               5                   10                  15

Glu Glu Gln Asn Lys Leu Val His Gly Gly Pro Cys Asp Lys Thr Ser
            20                  25                  30

His Pro Tyr Gln Ala Ala Leu Tyr Thr Ser Gly His Leu Leu Cys Gly
        35                  40                  45

Gly Val Leu Ile His Pro Leu Trp Val Leu Thr Ala Ala His Cys Lys
    50                  55                  60

Lys Pro Asn Leu Gln Val Phe Leu Gly Lys His Asn Leu Arg Gln Arg
65                  70                  75                  80

Glu Ser Ser Gln Glu Gln Ser Ser Val Val Arg Ala Val Ile His Pro
            85                  90                  95

Asp Tyr Asp Ala Ala Ser His Asp Gln Asp Ile Met Leu Leu Arg Leu
        100                 105                 110

Ala Arg Pro Ala Lys Leu Ser Glu Leu Ile Gln Pro Leu Pro Leu Glu
    115                 120                 125

Arg Asp Cys Ser Ala Asn Thr Thr Ser Cys His Ile Leu Gly Trp Gly
130                 135                 140

Lys Thr Ala Asp Gly Asp Phe Pro Asp Thr Ile Gln Cys Ala Tyr Ile
145                 150                 155                 160

His Leu Val Ser Arg Glu Glu Cys Glu His Ala Tyr Pro Gly Gln Ile
            165                 170                 175

Thr Gln Asn Met Leu Cys Ala Gly Asp Glu Lys Tyr Gly Lys Asp Ser
        180                 185                 190
```

-continued

```
Cys Gln Gly Asp Ser Gly Gly Pro Leu Val Cys Gly Asp His Leu Arg
            195                 200                 205
Gly Leu Val Ser Trp Gly Asn Ile Pro Cys Gly Ser Lys Glu Lys Pro
210                 215                 220
Gly Val Tyr Thr Asn Val Cys Arg Tyr Thr Asn Trp Ile Gln Lys Thr
225                 230                 235                 240
Ile Gln Ala Lys

<210> SEQ ID NO 26
<211> LENGTH: 277
<212> TYPE: PRT
<213> ORGANISM: Homo sapiens

<400> SEQUENCE: 26

Met Trp Pro Leu Ala Leu Val Ile Ala Ser Leu Thr Leu Ala Leu Ser
1               5                   10                  15
Gly Gly Val Ser Gln Glu Ser Ser Lys Val Leu Asn Thr Asn Gly Thr
            20                  25                  30
Ser Gly Phe Leu Pro Gly Gly Tyr Thr Cys Phe Pro His Ser Gln Pro
        35                  40                  45
Trp Gln Ala Ala Leu Leu Val Gln Gly Arg Leu Leu Cys Gly Gly Val
    50                  55                  60
Leu Val His Pro Lys Trp Val Leu Thr Ala Ala His Cys Leu Lys Glu
65                  70                  75                  80
Gly Leu Lys Val Tyr Leu Gly Lys His Ala Leu Gly Arg Val Glu Ala
                85                  90                  95
Gly Glu Gln Val Arg Glu Val Val His Ser Ile Pro His Pro Glu Tyr
            100                 105                 110
Arg Arg Ser Pro Thr His Leu Asn His Asp His Asp Ile Met Leu Leu
        115                 120                 125
Glu Leu Gln Ser Pro Val Gln Leu Thr Gly Tyr Ile Gln Thr Leu Pro
    130                 135                 140
Leu Ser His Asn Asn Arg Leu Thr Pro Gly Thr Thr Cys Arg Val Ser
145                 150                 155                 160
Gly Trp Gly Thr Thr Thr Ser Pro Gln Val Asn Tyr Pro Lys Thr Leu
                165                 170                 175
Gln Cys Ala Asn Ile Gln Leu Arg Ser Asp Glu Glu Cys Arg Gln Val
            180                 185                 190
Tyr Pro Gly Lys Ile Thr Asp Asn Met Leu Cys Ala Gly Thr Lys Glu
        195                 200                 205
Gly Gly Lys Asp Ser Cys Glu Gly Asp Ser Gly Gly Pro Leu Val Cys
    210                 215                 220
Asn Arg Thr Leu Tyr Gly Ile Val Ser Trp Gly Asp Phe Pro Cys Gly
225                 230                 235                 240
Gln Pro Asp Arg Pro Gly Val Tyr Thr Arg Val Ser Arg Tyr Val Leu
                245                 250                 255
Trp Ile Arg Glu Thr Ile Arg Lys Tyr Glu Thr Gln Gln Gln Lys Trp
            260                 265                 270
Leu Lys Gly Pro Gln
        275

<210> SEQ ID NO 27
<211> LENGTH: 251
<212> TYPE: PRT
<213> ORGANISM: Homo sapiens
```

<400> SEQUENCE: 27

```
Met Phe Leu Leu Leu Thr Ala Leu Gln Val Leu Ala Ile Ala Met Thr
1               5                   10                  15

Gln Ser Gln Glu Asp Glu Asn Lys Ile Ile Gly Gly His Thr Cys Thr
            20                  25                  30

Arg Ser Ser Gln Pro Trp Gln Ala Ala Leu Leu Ala Gly Pro Arg Arg
        35                  40                  45

Arg Phe Leu Cys Gly Gly Ala Leu Leu Ser Gly Gln Trp Val Ile Thr
    50                  55                  60

Ala Ala His Cys Gly Arg Pro Ile Leu Gln Val Ala Leu Gly Lys His
65                  70                  75                  80

Asn Leu Arg Arg Trp Glu Ala Thr Gln Gln Val Leu Arg Val Val Arg
                85                  90                  95

Gln Val Thr His Pro Asn Tyr Asn Ser Arg Thr His Asp Asn Asp Leu
            100                 105                 110

Met Leu Leu Gln Leu Gln Gln Pro Ala Arg Ile Gly Arg Ala Val Arg
        115                 120                 125

Pro Ile Glu Val Thr Gln Ala Cys Ala Ser Pro Gly Thr Ser Cys Arg
    130                 135                 140

Val Ser Gly Trp Gly Thr Ile Ser Ser Pro Ile Ala Arg Tyr Pro Ala
145                 150                 155                 160

Ser Leu Gln Cys Val Asn Ile Asn Ile Ser Pro Asp Glu Val Cys Gln
                165                 170                 175

Lys Ala Tyr Pro Arg Thr Ile Thr Pro Gly Met Val Cys Ala Gly Val
            180                 185                 190

Pro Gln Gly Gly Lys Asp Ser Cys Gln Gly Asp Ser Gly Gly Pro Leu
        195                 200                 205

Val Cys Arg Gly Gln Leu Gln Gly Leu Val Ser Trp Gly Met Glu Arg
    210                 215                 220

Cys Ala Leu Pro Gly Tyr Pro Gly Val Tyr Thr Asn Leu Cys Lys Tyr
225                 230                 235                 240

Arg Ser Trp Ile Glu Glu Thr Met Arg Asp Lys
                245                 250
```

<210> SEQ ID NO 28
<211> LENGTH: 277
<212> TYPE: PRT
<213> ORGANISM: Homo sapiens

<400> SEQUENCE: 28

```
Met Gln Arg Leu Arg Trp Leu Arg Asp Trp Lys Ser Ser Gly Arg Gly
1               5                   10                  15

Leu Thr Ala Ala Lys Glu Pro Gly Ala Arg Ser Ser Pro Leu Gln Ala
            20                  25                  30

Met Arg Ile Leu Gln Leu Ile Leu Leu Ala Leu Ala Thr Gly Leu Val
        35                  40                  45

Gly Gly Glu Thr Arg Ile Ile Lys Gly Phe Glu Cys Lys Pro His Ser
    50                  55                  60

Gln Pro Trp Gln Ala Ala Leu Phe Glu Lys Thr Arg Leu Leu Cys Gly
65                  70                  75                  80

Ala Thr Leu Ile Ala Pro Arg Trp Leu Leu Thr Ala Ala His Cys Leu
                85                  90                  95

Lys Pro Arg Tyr Ile Val His Leu Gly Gln His Asn Leu Gln Lys Glu
            100                 105                 110
```

```
Glu Gly Cys Glu Gln Thr Arg Thr Ala Thr Glu Ser Phe Pro His Pro
        115                 120                 125

Gly Phe Asn Asn Ser Leu Pro Asn Lys Asp His Arg Asn Asp Ile Met
    130                 135                 140

Leu Val Lys Met Ala Ser Pro Val Ser Ile Thr Trp Ala Val Arg Pro
145                 150                 155                 160

Leu Thr Leu Ser Ser Arg Cys Val Thr Ala Gly Thr Ser Cys Leu Ile
                165                 170                 175

Ser Gly Trp Gly Ser Thr Ser Ser Pro Gln Leu Arg Leu Pro His Thr
            180                 185                 190

Leu Arg Cys Ala Asn Ile Thr Ile Ile Glu His Gln Lys Cys Glu Asn
        195                 200                 205

Ala Tyr Pro Gly Asn Ile Thr Asp Thr Met Val Cys Ala Ser Val Gln
    210                 215                 220

Glu Gly Gly Lys Asp Ser Cys Gln Gly Asp Ser Gly Gly Pro Leu Val
225                 230                 235                 240

Cys Asn Gln Ser Leu Gln Gly Ile Ile Ser Trp Gly Gln Asp Pro Cys
                245                 250                 255

Ala Ile Thr Arg Lys Pro Gly Val Tyr Thr Lys Val Cys Lys Tyr Val
        260                 265                 270

Asp Trp Ile Gln Glu
        275

<210> SEQ ID NO 29
<211> LENGTH: 250
<212> TYPE: PRT
<213> ORGANISM: Homo sapiens

<400> SEQUENCE: 29

Met Lys Leu Gly Leu Leu Cys Ala Leu Leu Ser Leu Leu Ala Gly His
1               5                   10                  15

Gly Trp Ala Asp Thr Arg Ala Ile Gly Ala Glu Cys Arg Pro Asn
            20                  25                  30

Ser Gln Pro Trp Gln Ala Gly Leu Phe His Leu Thr Arg Leu Phe Cys
        35                  40                  45

Gly Ala Thr Leu Ile Ser Asp Arg Trp Leu Leu Thr Ala Ala His Cys
    50                  55                  60

Arg Lys Pro Tyr Leu Trp Val Arg Leu Gly Glu His His Leu Trp Lys
65                  70                  75                  80

Trp Glu Gly Pro Glu Gln Leu Phe Arg Val Thr Asp Phe Phe Pro His
                85                  90                  95

Pro Gly Phe Asn Lys Asp Leu Ser Ala Asn Asp His Asn Asp Asp Ile
            100                 105                 110

Met Leu Ile Arg Leu Pro Arg Gln Ala Arg Leu Ser Pro Ala Val Gln
        115                 120                 125

Pro Leu Asn Leu Ser Gln Thr Cys Val Ser Pro Gly Met Gln Cys Leu
    130                 135                 140

Ile Ser Gly Trp Gly Ala Val Ser Ser Pro Lys Ala Leu Phe Pro Val
145                 150                 155                 160

Thr Leu Gln Cys Ala Asn Ile Ser Ile Leu Glu Asn Lys Leu Cys His
                165                 170                 175

Trp Ala Tyr Pro Gly His Ile Ser Asp Ser Met Leu Cys Ala Gly Leu
            180                 185                 190

Trp Glu Gly Gly Arg Gly Ser Cys Gln Gly Asp Ser Gly Gly Pro Leu
        195                 200                 205
```

Val Cys Asn Gly Thr Leu Ala Gly Val Val Ser Gly Gly Ala Glu Pro
210                 215                 220

Cys Ser Arg Pro Arg Pro Ala Val Tyr Thr Ser Val Cys His Tyr
225                 230                 235                 240

Leu Asp Trp Ile Gln Glu Ile Met Glu Asn
                245                 250

<210> SEQ ID NO 30
<211> LENGTH: 276
<212> TYPE: PRT
<213> ORGANISM: Homo sapiens

<400> SEQUENCE: 30

Met Arg Ala Pro His Leu His Leu Ser Ala Ala Ser Gly Ala Arg Ala
1               5                   10                  15

Leu Ala Lys Leu Leu Pro Leu Leu Met Ala Gln Leu Trp Ala Ala Glu
                20                  25                  30

Ala Ala Leu Leu Pro Gln Asn Asp Thr Arg Leu Asp Pro Glu Ala Tyr
                35                  40                  45

Gly Ala Pro Cys Ala Arg Gly Ser Gln Pro Trp Gln Val Ser Leu Phe
50                  55                  60

Asn Gly Leu Ser Phe His Cys Ala Gly Val Leu Val Asp Gln Ser Trp
65                  70                  75                  80

Val Leu Thr Ala Ala His Cys Gly Asn Lys Pro Leu Trp Ala Arg Val
                85                  90                  95

Gly Asp Asp His Leu Leu Leu Leu Gln Gly Glu Gln Leu Arg Arg Thr
                100                 105                 110

Thr Arg Ser Val Val His Pro Lys Tyr His Gln Gly Ser Gly Pro Ile
                115                 120                 125

Leu Pro Arg Arg Thr Asp Glu His Asp Leu Met Leu Leu Lys Leu Ala
                130                 135                 140

Arg Pro Val Val Pro Gly Pro Arg Val Arg Ala Leu Gln Leu Pro Tyr
145                 150                 155                 160

Arg Cys Ala Gln Pro Gly Asp Gln Cys Gln Val Ala Gly Trp Gly Thr
                165                 170                 175

Thr Ala Ala Arg Arg Val Lys Tyr Asn Lys Gly Leu Thr Cys Ser Ser
                180                 185                 190

Ile Thr Ile Leu Ser Pro Lys Glu Cys Glu Val Phe Tyr Pro Gly Val
                195                 200                 205

Val Thr Asn Asn Met Ile Cys Ala Gly Leu Asp Arg Gly Gln Asp Pro
210                 215                 220

Cys Gln Ser Asp Ser Gly Gly Pro Leu Val Cys Asp Glu Thr Leu Gln
225                 230                 235                 240

Gly Ile Leu Ser Trp Gly Val Tyr Pro Cys Gly Ser Ala Gln His Pro
                245                 250                 255

Ala Val Tyr Thr Gln Ile Cys Lys Tyr Met Ser Trp Ile Asn Lys Val
                260                 265                 270

Ile Arg Ser Asn
275

<210> SEQ ID NO 31
<211> LENGTH: 248
<212> TYPE: PRT
<213> ORGANISM: Homo sapiens

<400> SEQUENCE: 31

```
Met Gly Leu Ser Ile Phe Leu Leu Cys Val Leu Gly Leu Ser Gln
1               5                   10                  15

Ala Ala Thr Pro Lys Ile Phe Asn Gly Thr Glu Cys Gly Arg Asn Ser
            20                  25                  30

Gln Pro Trp Gln Val Gly Leu Phe Glu Gly Thr Ser Leu Arg Cys Gly
        35                  40                  45

Gly Val Leu Ile Asp His Arg Trp Val Leu Thr Ala Ala His Cys Ser
    50                  55                  60

Gly Ser Arg Tyr Trp Val Arg Leu Gly Glu His Ser Leu Ser Gln Leu
65                  70                  75                  80

Asp Trp Thr Glu Gln Ile Arg His Ser Gly Phe Ser Val Thr His Pro
                85                  90                  95

Gly Tyr Leu Gly Ala Ser Thr Ser His Glu His Asp Leu Arg Leu Leu
            100                 105                 110

Arg Leu Arg Leu Pro Val Arg Val Thr Ser Ser Val Gln Pro Leu Pro
        115                 120                 125

Leu Pro Asn Asp Cys Ala Thr Ala Gly Thr Glu Cys His Val Ser Gly
130                 135                 140

Trp Gly Ile Thr Asn His Pro Arg Asn Pro Phe Pro Asp Leu Leu Gln
145                 150                 155                 160

Cys Leu Asn Leu Ser Ile Val Ser His Ala Thr Cys His Gly Val Tyr
                165                 170                 175

Pro Gly Arg Ile Thr Ser Asn Met Val Cys Ala Gly Gly Val Pro Gly
            180                 185                 190

Gln Asp Ala Cys Gln Gly Asp Ser Gly Gly Pro Leu Val Cys Gly Gly
        195                 200                 205

Val Leu Gln Gly Leu Val Ser Trp Gly Ser Val Gly Pro Cys Gly Gln
    210                 215                 220

Asp Gly Ile Pro Gly Val Tyr Thr Tyr Ile Cys Lys Tyr Val Asp Trp
225                 230                 235                 240

Ile Arg Met Ile Met Arg Asn Asn
                245

<210> SEQ ID NO 32
<211> LENGTH: 260
<212> TYPE: PRT
<213> ORGANISM: Homo sapiens

<400> SEQUENCE: 32

Met Gly Arg Pro Arg Pro Arg Ala Ala Lys Thr Trp Met Phe Leu Leu
1               5                   10                  15

Leu Leu Gly Gly Ala Trp Ala Gly His Ser Arg Ala Gln Glu Asp Lys
            20                  25                  30

Val Leu Gly Gly His Glu Cys Gln Pro His Ser Gln Pro Trp Gln Ala
        35                  40                  45

Ala Leu Phe Gln Gly Gln Gln Leu Leu Cys Gly Gly Val Leu Val Gly
    50                  55                  60

Gly Asn Trp Val Leu Thr Ala Ala His Cys Lys Lys Pro Lys Tyr Thr
65                  70                  75                  80

Val Arg Leu Gly Asp His Ser Leu Gln Asn Lys Asp Gly Pro Glu Gln
                85                  90                  95

Glu Ile Pro Val Val Gln Ser Ile Pro His Pro Cys Tyr Asn Ser Ser
            100                 105                 110

Asp Val Glu Asp His Asn His Asp Leu Met Leu Leu Gln Leu Arg Asp
```

```
            115                 120                 125
Gln Ala Ser Leu Gly Ser Lys Val Lys Pro Ile Ser Leu Ala Asp His
        130                 135                 140
Cys Thr Gln Pro Gly Gln Lys Cys Thr Val Ser Gly Trp Gly Thr Val
145                 150                 155                 160
Thr Ser Pro Arg Glu Asn Phe Pro Asp Thr Leu Asn Cys Ala Glu Val
                165                 170                 175
Lys Ile Phe Pro Gln Lys Lys Cys Glu Asp Ala Tyr Pro Gly Gln Ile
            180                 185                 190
Thr Asp Gly Met Val Cys Ala Gly Ser Ser Lys Gly Ala Asp Thr Cys
        195                 200                 205
Gln Gly Asp Ser Gly Gly Pro Leu Val Cys Asp Gly Ala Leu Gln Gly
    210                 215                 220
Ile Thr Ser Trp Gly Ser Asp Pro Cys Gly Arg Ser Asp Lys Pro Gly
225                 230                 235                 240
Val Tyr Thr Asn Ile Cys Arg Tyr Leu Asp Trp Ile Lys Lys Ile Ile
                245                 250                 255
Gly Ser Lys Gly
            260

<210> SEQ ID NO 33
<211> LENGTH: 261
<212> TYPE: PRT
<213> ORGANISM: Homo sapiens

<400> SEQUENCE: 33

Met Trp Val Pro Val Phe Leu Thr Leu Ser Val Thr Trp Ile Gly
1               5                   10                  15
Ala Ala Pro Leu Ile Leu Ser Arg Ile Val Gly Gly Trp Glu Cys Glu
                20                  25                  30
Lys His Ser Gln Pro Trp Gln Val Leu Val Ala Ser Arg Gly Arg Ala
            35                  40                  45
Val Cys Gly Gly Val Leu Val His Pro Gln Trp Val Leu Thr Ala Ala
        50                  55                  60
His Cys Ile Arg Asn Lys Ser Val Ile Leu Leu Gly Arg His Ser Leu
65                  70                  75                  80
Phe His Pro Glu Asp Thr Gly Gln Val Phe Gln Val Ser His Ser Phe
                85                  90                  95
Pro His Pro Leu Tyr Asp Met Ser Leu Leu Lys Asn Arg Phe Leu Arg
            100                 105                 110
Pro Gly Asp Asp Ser Ser His Asp Leu Met Leu Leu Arg Leu Ser Glu
        115                 120                 125
Pro Ala Glu Leu Thr Asp Ala Val Lys Val Met Asp Leu Pro Thr Gln
    130                 135                 140
Glu Pro Ala Leu Gly Thr Thr Cys Tyr Ala Ser Gly Trp Gly Ser Ile
145                 150                 155                 160
Glu Pro Glu Glu Phe Leu Thr Pro Lys Lys Leu Gln Cys Val Asp Leu
                165                 170                 175
His Val Ile Ser Asn Asp Val Cys Ala Gln Val His Pro Gln Lys Val
            180                 185                 190
Thr Lys Phe Met Leu Cys Ala Gly Arg Trp Thr Gly Gly Lys Ser Thr
        195                 200                 205
Cys Ser Gly Asp Ser Gly Gly Pro Leu Val Cys Asn Gly Val Leu Gln
    210                 215                 220
```

```
Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 34
<211> LENGTH: 261
<212> TYPE: PRT
<213> ORGANISM: Homo sapiens

<400> SEQUENCE: 34

Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Gly Asp Ser Gly Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255

Ile Ala Ala Asn Pro
            260

<210> SEQ ID NO 35
<211> LENGTH: 262
<212> TYPE: PRT
<213> ORGANISM: Homo sapiens

<400> SEQUENCE: 35

Met Trp Phe Leu Val Leu Cys Leu Ala Leu Ser Leu Gly Gly Thr Gly
1               5                   10                  15
```

```
Ala Ala Pro Pro Ile Gln Ser Arg Ile Val Gly Gly Trp Glu Cys Glu
         20                  25                  30

Gln His Ser Gln Pro Trp Gln Ala Ala Leu Tyr His Phe Ser Thr Phe
             35                  40                  45

Gln Cys Gly Gly Ile Leu Val His Arg Gln Trp Val Leu Thr Ala Ala
 50                  55                  60

His Cys Ile Ser Asp Asn Tyr Gln Leu Trp Leu Gly Arg His Asn Leu
 65                  70                  75                  80

Phe Asp Asp Glu Asn Thr Ala Gln Phe Val His Val Ser Glu Ser Phe
                 85                  90                  95

Pro His Pro Gly Phe Asn Met Ser Leu Leu Glu Asn His Thr Arg Gln
             100                 105                 110

Ala Asp Glu Asp Tyr Ser His Asp Leu Met Leu Leu Arg Leu Thr Glu
         115                 120                 125

Pro Ala Asp Thr Ile Thr Asp Ala Val Lys Val Val Glu Leu Pro Thr
130                 135                 140

Glu Glu Pro Glu Val Gly Ser Thr Cys Leu Ala Ser Gly Trp Gly Ser
145                 150                 155                 160

Ile Glu Pro Glu Asn Phe Ser Phe Pro Asp Asp Leu Gln Cys Val Asp
                 165                 170                 175

Leu Lys Ile Leu Pro Asn Asp Glu Cys Lys Lys Ala His Val Gln Lys
             180                 185                 190

Val Thr Asp Phe Met Leu Cys Val Gly His Leu Glu Gly Gly Lys Asp
         195                 200                 205

Thr Cys Val Gly Asp Ser Gly Gly Pro Leu Met Cys Asp Gly Val Leu
210                 215                 220

Gln Gly Val Thr Ser Trp Gly Tyr Val Pro Cys Gly Thr Pro Asn Lys
225                 230                 235                 240

Pro Ser Val Ala Val Arg Val Leu Ser Tyr Val Lys Trp Ile Glu Asp
                 245                 250                 255

Thr Ile Ala Glu Asn Ser
            260

<210> SEQ ID NO 36
<211> LENGTH: 293
<212> TYPE: PRT
<213> ORGANISM: Homo sapiens

<400> SEQUENCE: 36

Met Ala Thr Ala Arg Pro Pro Trp Met Trp Val Leu Cys Ala Leu Ile
1               5                   10                  15

Thr Ala Leu Leu Leu Gly Val Thr Glu His Val Leu Ala Asn Asn Asp
             20                  25                  30

Val Ser Cys Asp His Pro Ser Asn Thr Val Pro Ser Gly Ser Asn Gln
         35                  40                  45

Asp Leu Gly Ala Gly Ala Gly Glu Asp Ala Arg Ser Asp Asp Ser Ser
     50                  55                  60

Ser Arg Ile Ile Asn Gly Ser Asp Cys Asp Met His Thr Gln Pro Trp
 65                  70                  75                  80

Gln Ala Ala Leu Leu Leu Arg Pro Asn Gln Leu Tyr Cys Gly Ala Val
                 85                  90                  95

Leu Val His Pro Gln Trp Leu Leu Thr Ala Ala His Cys Arg Lys Lys
             100                 105                 110

Val Phe Arg Val Arg Leu Gly His Tyr Ser Leu Ser Pro Val Tyr Glu
         115                 120                 125
```

```
Ser Gly Gln Gln Met Phe Gln Gly Val Lys Ser Ile Pro His Pro Gly
        130                 135                 140

Tyr Ser His Pro Gly His Ser Asn Asp Leu Met Leu Ile Lys Leu Asn
145                 150                 155                 160

Arg Arg Ile Arg Pro Thr Lys Asp Val Arg Pro Ile Asn Val Ser Ser
                165                 170                 175

His Cys Pro Ser Ala Gly Thr Lys Cys Leu Val Ser Gly Trp Gly Thr
            180                 185                 190

Thr Lys Ser Pro Gln Val His Phe Pro Lys Val Leu Gln Cys Leu Asn
        195                 200                 205

Ile Ser Val Leu Ser Gln Lys Arg Cys Glu Asp Ala Tyr Pro Arg Gln
    210                 215                 220

Ile Asp Asp Thr Met Phe Cys Ala Gly Asp Lys Ala Gly Arg Asp Ser
225                 230                 235                 240

Cys Gln Gly Asp Ser Gly Gly Pro Val Val Cys Asn Gly Ser Leu Gln
                245                 250                 255

Gly Leu Val Ser Trp Gly Asp Tyr Pro Cys Ala Arg Pro Asn Arg Pro
            260                 265                 270

Gly Val Tyr Thr Asn Leu Cys Lys Phe Thr Lys Trp Ile Gln Glu Thr
        275                 280                 285

Ile Gln Ala Asn Ser
    290

<210> SEQ ID NO 37
<211> LENGTH: 253
<212> TYPE: PRT
<213> ORGANISM: Homo sapiens

<400> SEQUENCE: 37

Met Ala Thr Ala Gly Asn Pro Trp Gly Trp Phe Leu Gly Tyr Leu Ile
1               5                   10                  15

Leu Gly Val Ala Gly Ser Leu Val Ser Gly Ser Cys Ser Gln Ile Ile
                20                  25                  30

Asn Gly Glu Asp Cys Ser Pro His Ser Gln Pro Trp Gln Ala Ala Leu
            35                  40                  45

Val Met Glu Asn Glu Leu Phe Cys Ser Gly Val Leu Val His Pro Gln
        50                  55                  60

Trp Val Leu Ser Ala Ala His Cys Phe Gln Asn Ser Tyr Thr Ile Gly
65                  70                  75                  80

Leu Gly Leu His Ser Leu Glu Ala Asp Gln Glu Pro Gly Ser Gln Met
                85                  90                  95

Val Glu Ala Ser Leu Ser Val Arg His Pro Glu Tyr Asn Arg Pro Leu
            100                 105                 110

Leu Ala Asn Asp Leu Met Leu Ile Lys Leu Asp Glu Ser Val Ser Ser
        115                 120                 125

Asp Thr Ile Arg Ser Ile Ser Ile Ala Ser Gln Cys Pro Thr Ala Gly
    130                 135                 140

Asn Ser Cys Leu Val Ser Gly Trp Gly Leu Leu Ala Asn Gly Arg Met
145                 150                 155                 160

Pro Thr Val Leu Gln Cys Val Asn Val Ser Val Val Ser Glu Glu Val
                165                 170                 175

Cys Ser Lys Leu Tyr Asp Pro Leu Tyr His Pro Ser Met Phe Cys Ala
            180                 185                 190

Gly Gly Gly His Asp Gln Lys Asp Ser Cys Asn Gly Asp Ser Gly Gly
```

```
                195                 200                 205
Pro Leu Ile Cys Asn Gly Tyr Leu Gln Gly Leu Val Ser Phe Gly Lys
    210                 215                 220

Ala Pro Cys Gly Gln Val Gly Val Pro Gly Val Tyr Thr Asn Leu Cys
225                 230                 235                 240

Lys Phe Thr Glu Trp Ile Glu Lys Thr Val Gln Ala Ser
                245                 250
```

<210> SEQ ID NO 38
<211> LENGTH: 257
<212> TYPE: PRT
<213> ORGANISM: Homo sapiens

<400> SEQUENCE: 38

```
Met Ala Arg Ser Leu Leu Pro Leu Gln Ile Leu Leu Leu Ser Leu
1               5                   10                  15

Ala Leu Glu Thr Ala Gly Glu Glu Ala Gln Gly Asp Lys Ile Ile Asp
                20                  25                  30

Gly Ala Pro Cys Ala Arg Gly Ser His Pro Trp Gln Val Ala Leu Leu
            35                  40                  45

Ser Gly Asn Gln Leu His Cys His Ser Cys Cys Glu Gly Gly Val Leu
    50                  55                  60

Val Asn Glu Arg Trp Val Leu Thr Ala Ala His Cys Lys Met Asn Glu
65                  70                  75                  80

Tyr Thr Val His Leu Gly Ser Asp Thr Leu Gly Asp Arg Arg Ala Gln
                85                  90                  95

Arg Ile Lys Ala Ser Lys Ser Phe Arg His Pro Gly Tyr Ser Thr Gln
            100                 105                 110

Thr His Val Asn Asp Leu Met Leu Val Lys Leu Asn Ser Gln Ala Arg
        115                 120                 125

Leu Ser Ser Met Val Lys Lys Val Arg Leu Pro Ser Arg Cys Glu Pro
    130                 135                 140

Pro Gly Thr Thr Cys Thr Val Ser Gly Trp Gly Thr Thr Thr Ser Pro
145                 150                 155                 160

Asp Val Thr Phe Pro Asp Leu Met Cys Val Asp Val Lys Leu Ile Ser
                165                 170                 175

Pro Gln Asp Cys Thr Lys Val Tyr Lys Asp Leu Leu Glu Asn Ser Met
            180                 185                 190

Leu Cys Ala Gly Ile Pro Asp Ser Lys Lys Asn Ala Cys Asn Gly Asp
        195                 200                 205

Ser Gly Gly Pro Leu Val Cys Arg Gly Thr Leu Gln Gly Leu Val Ser
    210                 215                 220

Trp Gly Thr Phe Pro Cys Gly Gln Pro Asn Asp Pro Gly Val Tyr Thr
225                 230                 235                 240

Gln Val Cys Lys Phe Thr Lys Trp Ile Asn Asp Thr Met Lys Lys His
                245                 250                 255

Arg
```

<210> SEQ ID NO 39
<211> LENGTH: 24
<212> TYPE: DNA
<213> ORGANISM: Artificial Sequence
<220> FEATURE:
<223> OTHER INFORMATION: segments/peptides derived from human sequence

<400> SEQUENCE: 39

```
cacaacgagc ctgggaccgc tggg                                          24

<210> SEQ ID NO 40
<211> LENGTH: 6
<212> TYPE: DNA
<213> ORGANISM: Artificial Sequence
<220> FEATURE:
<223> OTHER INFORMATION: segments/peptides derived from human sequence

<400> SEQUENCE: 40 attaaa                                                               6

<210> SEQ ID NO 41
<211> LENGTH: 20
<212> TYPE: DNA
<213> ORGANISM: Artificial Sequence
<220> FEATURE:
<223> OTHER INFORMATION: segments/peptides derived from human sequence

<400> SEQUENCE: 41
atccctccat tcccatcttt                                               20

<210> SEQ ID NO 42
<211> LENGTH: 20
<212> TYPE: DNA
<213> ORGANISM: Artificial Sequence
<220> FEATURE:
<223> OTHER INFORMATION: segments/peptides derived from human sequence

<400> SEQUENCE: 42
cacatacaat tctctggttc                                               20

<210> SEQ ID NO 43
<211> LENGTH: 20
<212> TYPE: DNA
<213> ORGANISM: Artificial Sequence
<220> FEATURE:
<223> OTHER INFORMATION: segments/peptides derived from human sequence

<400> SEQUENCE: 43
agtgacactg tctcagaatt                                               20

<210> SEQ ID NO 44
<211> LENGTH: 20
<212> TYPE: DNA
<213> ORGANISM: Artificial Sequence
<220> FEATURE:
<223> OTHER INFORMATION: segments/peptides derived from human sequence

<400> SEQUENCE: 44
ccccaatctc acgagtgcac                                               20

<210> SEQ ID NO 45
<211> LENGTH: 20
<212> TYPE: DNA
<213> ORGANISM: Artificial Sequence
<220> FEATURE:
<223> OTHER INFORMATION: segments/peptides derived from human sequence

<400> SEQUENCE: 45
gtcggctctg gagacatttc                                               20

<210> SEQ ID NO 46
<211> LENGTH: 19
<212> TYPE: DNA
<213> ORGANISM: Artificial Sequence
```

```
<220> FEATURE:
<223> OTHER INFORMATION: segments/peptides derived from human sequence

<400> SEQUENCE: 46
aactggggag gcttgagtc                                                    19

<210> SEQ ID NO 47
<211> LENGTH: 20
<212> TYPE: DNA
<213> ORGANISM: Artificial Sequence
<220> FEATURE:
<223> OTHER INFORMATION: segments/peptides derived from human sequence

<400> SEQUENCE: 47
ctccttcctg ctggcatcca                                                   20

<210> SEQ ID NO 48
<211> LENGTH: 20
<212> TYPE: DNA
<213> ORGANISM: Artificial Sequence
<220> FEATURE:
<223> OTHER INFORMATION: segments/peptides derived from human sequence

<400> SEQUENCE: 48
atcacacggg tggtcatgtg                                                   20

<210> SEQ ID NO 49
<211> LENGTH: 20
<212> TYPE: DNA
<213> ORGANISM: Artificial Sequence
<220> FEATURE:
<223> OTHER INFORMATION: segments/peptides derived from human sequence

<400> SEQUENCE: 49
caagtggctc tctacgagcg                                                   20

<210> SEQ ID NO 50
<211> LENGTH: 20
<212> TYPE: DNA
<213> ORGANISM: Artificial Sequence
<220> FEATURE:
<223> OTHER INFORMATION: segments/peptides derived from human sequence

<400> SEQUENCE: 50
gacaccaggc ttggtggtgt                                                   20
```